United States Patent
Sun

(10) Patent No.: US 12,214,030 B2
(45) Date of Patent: Feb. 4, 2025

(54) **SELF-ADJUVANTING *YERSINIA* OUTER MEMBRANE VESICLE AS A VACCINE AGAINST PLAGUE, ANTHRAX AND PSEUDOMONAS INFECTION**

(71) Applicant: Albany Medical College, Albany, NY (US)

(72) Inventor: Wei Sun, Glenmont, NY (US)

(73) Assignee: Albany Medical College, Albany, NY (US)

( * ) Notice: Subject to any disclaimer, the term of this patent is extended or adjusted under 35 U.S.C. 154(b) by 671 days.

(21) Appl. No.: 17/482,527

(22) Filed: Sep. 23, 2021

(65) Prior Publication Data

US 2022/0280628 A1    Sep. 8, 2022

Related U.S. Application Data

(63) Continuation of application No. 17/117,417, filed on Dec. 10, 2020, now Pat. No. 11,167,019.

(60) Provisional application No. 62/947,585, filed on Dec. 13, 2019.

(51) Int. Cl.
| | | |
|---|---|---|
| *A61K 39/02* | (2006.01) | |
| *A61K 39/104* | (2006.01) | |
| *A61P 31/04* | (2006.01) | |
| *A61K 39/00* | (2006.01) | |

(52) U.S. Cl.
CPC ........ *A61K 39/0291* (2013.01); *A61K 39/104* (2013.01); *A61P 31/04* (2018.01); *A61K 2039/55594* (2013.01)

(58) Field of Classification Search
None
See application file for complete search history.

(56) References Cited

U.S. PATENT DOCUMENTS

2019/0091319 A1*  3/2019  Feron .................. C12N 9/1081

* cited by examiner

*Primary Examiner* — Jennifer E Graser

(74) *Attorney, Agent, or Firm* — David L. Nocilly; Bond Schoeneck & King PLLC

(57) ABSTRACT

A vaccine platform using a *Yersinia pestis* mutant synthesizing an adjuvant form lipid A (monophosphoryl lipid A, MPLA) for the increased biogenesis of bacterial outer membrane vesicles (OMVs). To enhance the immunogenicity of the OMVs, an Asd-based balanced-lethal host-vector system was constructed to oversynthesize the LcrV antigen of *Y. pestis*, raise the amounts of LcrV enclosed in OMVs by Type II secretion system, and eliminate harmful factors like plasminogen activator (Pla) and murine toxin from the OMVs. Vaccination with OMVs containing MPLA and increased amounts of LcrV with diminished toxicity afforded complete protection in mice against subcutaneous challenge and intranasal challenge and was significantly superior to that resulting from vaccination with LcrV/alhydrogel. Additionally, the *Yersinia* OMV can be used as a platform to deliver the heterologous antigens of *Bacillus anthraces*. Vaccination with multiantigenic self-adjuvanting bionanoparticles from *Pseudomonas* was also successfully tested in connection with *Pseudomonas aeruginosa*.

14 Claims, 79 Drawing Sheets

Figure 1B:
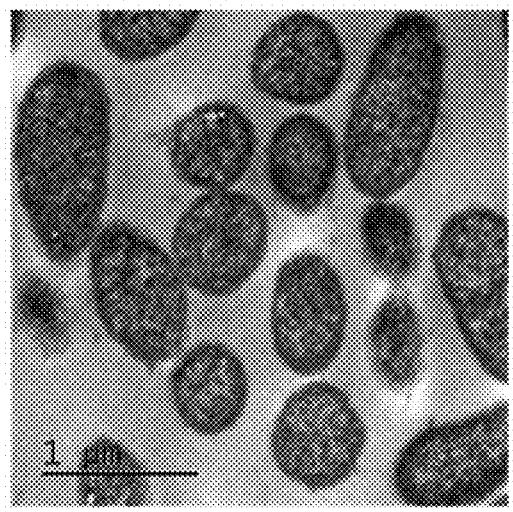
Figure 1B:
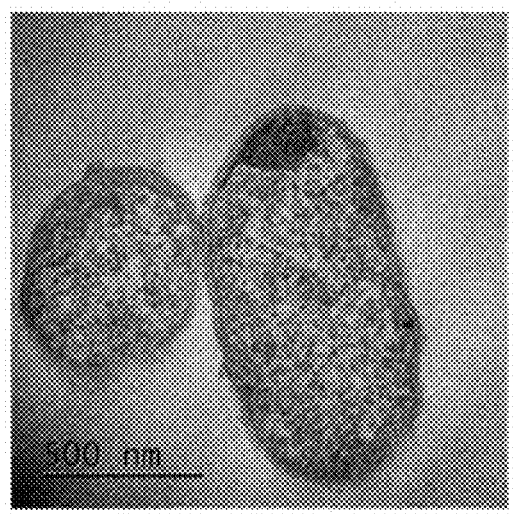

Specification includes a Sequence Listing.

*Y. pestis* KIM6+

FIG. 1A

B

χ10015 (*lpxL*)

C

χ10027 (*lpxL* + *lpxE*)

χ10015 (*lpxL*)

χ10027 (*lpxL + lpxE*)

A

Constructed Strains

| Strain | Genotype | Parent strain |
|---|---|---|
| YPs1 | Δasd pCD1⁻ | KIM6+ |
| YPs2 | Δasd ΔlpxP::P$_{lpxL}$ lpxL pCD1⁻ | lpxL |
| YPs3 | Δasd ΔlpxP::P$_{lpxL}$ lpxL ΔlacI::P$_{lpp}$ lpxE pCD1⁻ | lpxL +lpxE |

| Strain | Genotype |
|---|---|
| YPs7 | Δasd pCD1⁻ pPCP1⁻ Δymt |
| YPs8 | Δasd ΔlpxP::P$_{lpxL}$ lpxL pCD1⁻ pPCP1⁻ Δymt |
| YPs9 | Δasd ΔlpxP::P$_{lpxL}$ lpxL ΔlacI::P$_{lpp}$ lpxE pCD1⁻ pPCP1⁻ Δymt |

SEQUENCE LISTING

```
<160> NUMBER OF SEQ ID NOS: 65

<210> SEQ ID NO 1
<211> LENGTH: 29
```

-continued

```
<212> TYPE: DNA
<213> ORGANISM: Artificial Sequence
<220> FEATURE:
<223> OTHER INFORMATION: primer

<400> SEQUENCE: 1
cgggaattca tgattagagc ctacgaaca                                    29

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
atgattagag cctacgaaca                                              20

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
cggaagcttt catttaccag acgtgtcatc tag                               33

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
cggggtaccg gaaatgggcg atgccgtagt cgcg                              34

<210> SEQ ID NO 5
<211> LENGTH: 48
<212> TYPE: DNA
<213> ORGANISM: Artificial Sequence
<220> FEATURE:
<223> OTHER INFORMATION: primer

<400> SEQUENCE: 5
acgctatgcg ccgctaaaaa atagtgttta ctgccctgcc ttggaagg               48

<210> SEQ ID NO 6
<211> LENGTH: 48
<212> TYPE: DNA
<213> ORGANISM: Artificial Sequence
<220> FEATURE:
<223> OTHER INFORMATION: primer

<400> SEQUENCE: 6
cagggcagta aacactattt tttagcggcg catagcgtgt catatcgt               48

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
```

```
cggcccgggt cgaggagacc gaccagagcc tcg                               33

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
attaggatcc atcactgacg gagcacaacg g                                 31

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
gccgaagctt tgttaccgca gcaataccca t                                 31

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
cgggagctct atccatcggg ttctccgccc cgg                               33

<210> SEQ ID NO 11
<211> LENGTH: 48
<212> TYPE: DNA
<213> ORGANISM: Artificial Sequence
<220> FEATURE:
<223> OTHER INFORMATION: primer

<400> SEQUENCE: 11
tggcaacgcc ggggtcccgg gaggggcagg cggcgcgtcc tgacggga              48

<210> SEQ ID NO 12
<211> LENGTH: 48
<212> TYPE: DNA
<213> ORGANISM: Artificial Sequence
<220> FEATURE:
<223> OTHER INFORMATION: primer

<400> SEQUENCE: 12
tcccgtcagg acgcgccgcc tgcccctccc gggaccccgg cgttgcca              48

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
cggtctagat gactgcgtct cgttcg                                      26

<210> SEQ ID NO 14
<211> LENGTH: 30
<212> TYPE: DNA
<213> ORGANISM: Artificial Sequence
```

```
<220> FEATURE:
<223> OTHER INFORMATION: primer

<400> SEQUENCE: 14
cgggagctcg acagctcggc gtagaccagc                                         30

<210> SEQ ID NO 15
<211> LENGTH: 43
<212> TYPE: DNA
<213> ORGANISM: Artificial Sequence
<220> FEATURE:
<223> OTHER INFORMATION: primer

<400> SEQUENCE: 15
acccatcaca ggagccatcg cggtggtgat tccctcggcg atc                          43

<210> SEQ ID NO 16
<211> LENGTH: 43
<212> TYPE: DNA
<213> ORGANISM: Artificial Sequence
<220> FEATURE:
<223> OTHER INFORMATION: primer

<400> SEQUENCE: 16
gatcgccgag ggaatcacca ccgcgatggc tcctgtgatg ggt                          43

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
cggtctagag cgacgctcga caatgctct                                          29

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
cgggagctcg tcggcggctt cttcgggccg c                                       31

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
ttcgatgacc aggagctacc cgtcggcgcg gggcccggct cca                          43

<210> SEQ ID NO 20
<211> LENGTH: 43
<212> TYPE: DNA
<213> ORGANISM: Artificial Sequence
<220> FEATURE:
<223> OTHER INFORMATION: primer

<400> SEQUENCE: 20
tggagccggg ccccgcgccg acgggtagct cctggtcatc gaa                          43
```

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
cggtctagaa gccggacgag gacgacggtt a         31

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
cgggagctcg atgttccacg gggtgttcca          30

<210> SEQ ID NO 23
<211> LENGTH: 49
<212> TYPE: DNA
<213> ORGANISM: Artificial Sequence
<220> FEATURE:
<223> OTHER INFORMATION: primer

<400> SEQUENCE: 23
tgctggccgg ggccaccgag cttacttgtt cagttctcct ggttttttc          49

<210> SEQ ID NO 24
<211> LENGTH: 49
<212> TYPE: DNA
<213> ORGANISM: Artificial Sequence
<220> FEATURE:
<223> OTHER INFORMATION: primer

<400> SEQUENCE: 24
gaaaaaacca ggagaactga acaagtaagc tcggtggccc cggccagca          49

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
cggtctagag gtcgtgtgct ggggatcgaa          30

<210> SEQ ID NO 26
<211> LENGTH: 34
<212> TYPE: DNA
<213> ORGANISM: Artificial Sequence
<220> FEATURE:
<223> OTHER INFORMATION: primer

<400> SEQUENCE: 26
cgggagctcg ctgctacttc acccatagct agcg          34

<210> SEQ ID NO 27
<211> LENGTH: 49
<212> TYPE: DNA
<213> ORGANISM: Artificial Sequence
<220> FEATURE:
<223> OTHER INFORMATION: primer

```
<400> SEQUENCE: 27
ctttctatcg agaaccccct tccagactgc gctacaaggc cggccagga                49

<210> SEQ ID NO 28
<211> LENGTH: 49
<212> TYPE: DNA
<213> ORGANISM: Artificial Sequence
<220> FEATURE:
<223> OTHER INFORMATION: primer

<400> SEQUENCE: 28
tcctggccgg ccttgtagcg cagtctggaa gggggttctc gatagaaag                49

<210> SEQ ID NO 29
<211> LENGTH: 34
<212> TYPE: DNA
<213> ORGANISM: Artificial Sequence
<220> FEATURE:
<223> OTHER INFORMATION: primer

<400> SEQUENCE: 29
cggtctagac ccaccataac accatatgcg gtca                                34

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30
cgggagctcc acctgttcgt ctccgcccat c                                   31

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31
ggccgcaggg ggtcttcgtt tgcggcaccc cgtgtctggc gc                       42

<210> SEQ ID NO 32
<211> LENGTH: 42
<212> TYPE: DNA
<213> ORGANISM: Artificial Sequence
<220> FEATURE:
<223> OTHER INFORMATION: primer

<400> SEQUENCE: 32
gcgccagaca cggggtgccg caaacgaaga ccccctgcgg cc                       42

<210> SEQ ID NO 33
<211> LENGTH: 31
<212> TYPE: DNA
<213> ORGANISM: Artificial Sequence
<220> FEATURE:
<223> OTHER INFORMATION: primer

<400> SEQUENCE: 33
cggtctagaa actaatcgcc atgaatgaaa a                                   31

<210> SEQ ID NO 34
```

```
<211> LENGTH: 31
<212> TYPE: DNA
<213> ORGANISM: Artificial Sequence
<220> FEATURE:
<223> OTHER INFORMATION: primer

<400> SEQUENCE: 34
cgggagctcg ctgccggagg acgtggagaa c                              31

<210> SEQ ID NO 35
<211> LENGTH: 44
<212> TYPE: DNA
<213> ORGANISM: Artificial Sequence
<220> FEATURE:
<223> OTHER INFORMATION: primer

<400> SEQUENCE: 35
tggccttcga gatctttcag ggatcggaac tctcaacggt tggc                44

<210> SEQ ID NO 36
<211> LENGTH: 44
<212> TYPE: DNA
<213> ORGANISM: Artificial Sequence
<220> FEATURE:
<223> OTHER INFORMATION: primer

<400> SEQUENCE: 36
gccaaccgtt gagagttccg atccctgaaa gatctcgaag gcca                44

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
cggtctagaa aggcaatagg agtttcatcc ag                             32

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
cgggagctcg acgtgctgct caacctggct tcc                            33

<210> SEQ ID NO 39
<211> LENGTH: 44
<212> TYPE: DNA
<213> ORGANISM: Artificial Sequence
<220> FEATURE:
<223> OTHER INFORMATION: primer

<400> SEQUENCE: 39
catcttcatg gtcgggtacc ggtaggatgt tttctctgcg aggg                44

<210> SEQ ID NO 40
<211> LENGTH: 44
<212> TYPE: DNA
<213> ORGANISM: Artificial Sequence
<220> FEATURE:
<223> OTHER INFORMATION: primer

<400> SEQUENCE: 40
```

-continued

```
ccctcgcaga gaaaacatcc taccggtacc cgaccatgaa gatg          44
```

<210> SEQ ID NO 41
<211> LENGTH: 31
<212> TYPE: DNA
<213> ORGANISM: Artificial Sequence
<220> FEATURE:
<223> OTHER INFORMATION: primer

<400> SEQUENCE: 41

```
cggtctagac gccctggtcg ggatagtcgt a          31
```

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42

```
cgggagctcc tgcctgggca agagcaccta c          31
```

<210> SEQ ID NO 43
<211> LENGTH: 42
<212> TYPE: DNA
<213> ORGANISM: Artificial Sequence
<220> FEATURE:
<223> OTHER INFORMATION: primer

<400> SEQUENCE: 43

```
tatctgttat gccagcaccg tttcacacct cccaaaaatt tt          42
```

<210> SEQ ID NO 44
<211> LENGTH: 42
<212> TYPE: DNA
<213> ORGANISM: Artificial Sequence
<220> FEATURE:
<223> OTHER INFORMATION: primer

<400> SEQUENCE: 44

```
aaaatttttg ggaggtgtga aacggtgctg gcataacaga ta          42
```

<210> SEQ ID NO 45
<211> LENGTH: 31
<212> TYPE: DNA
<213> ORGANISM: Artificial Sequence
<220> FEATURE:
<223> OTHER INFORMATION: primer

<400> SEQUENCE: 45

```
cggtctagag gcgatttccc cggaactctt g          31
```

<210> SEQ ID NO 46
<211> LENGTH: 31
<212> TYPE: DNA
<213> ORGANISM: Artificial Sequence
<220> FEATURE:
<223> OTHER INFORMATION: primer

<400> SEQUENCE: 46

```
cgggagctct ggaacgcctg ctcgccgctc a          31
```

<210> SEQ ID NO 47
<211> LENGTH: 41
<212> TYPE: DNA

```
<213> ORGANISM: Artificial Sequence
<220> FEATURE:
<223> OTHER INFORMATION: primer

<400> SEQUENCE: 47
gccaatccag aggaactgga atcggcgcca cgccgccacg c                    41

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
gcgtggcggc gtggcgccga ttccagttcc tctggattgg c                    41

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
cggtctagat gtcttcatcg agggttccag tta                             33

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
cgggagctct tgacttccgg tgggtaggtt tcg                             33

<210> SEQ ID NO 51
<211> LENGTH: 41
<212> TYPE: DNA
<213> ORGANISM: Artificial Sequence
<220> FEATURE:
<223> OTHER INFORMATION: primer

<400> SEQUENCE: 51
accacccggg aaataaaacg agcgaggagt ccatcgcatg a                    41

<210> SEQ ID NO 52
<211> LENGTH: 41
<212> TYPE: DNA
<213> ORGANISM: Artificial Sequence
<220> FEATURE:
<223> OTHER INFORMATION: primer

<400> SEQUENCE: 52
tcatgcgatg gactcctcgc tcgttttatt tcccgggtgg t                    41

<210> SEQ ID NO 53
<211> LENGTH: 31
<212> TYPE: DNA
<213> ORGANISM: Artificial Sequence
<220> FEATURE:
<223> OTHER INFORMATION: primer

<400> SEQUENCE: 53
cggtctagag gagtagtggc cgatgatccc t                               31
```

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
cgggagctcg cgcaccggag tcttcaccac ctt                33

<210> SEQ ID NO 55
<211> LENGTH: 41
<212> TYPE: DNA
<213> ORGANISM: Artificial Sequence
<220> FEATURE:
<223> OTHER INFORMATION: primer

<400> SEQUENCE: 55
cgcgtccgga atgcccgtcc ggacggttcc gacgacgatc a        41

<210> SEQ ID NO 56
<211> LENGTH: 41
<212> TYPE: DNA
<213> ORGANISM: Artificial Sequence
<220> FEATURE:
<223> OTHER INFORMATION: primer

<400> SEQUENCE: 56
tgatcgtcgt cggaaccgtc cggacgggca ttccggacgc g        41

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57
cggtctagat cgccgaagta ctcgcggttg a                  31

<210> SEQ ID NO 58
<211> LENGTH: 31
<212> TYPE: DNA
<213> ORGANISM: Artificial Sequence
<220> FEATURE:
<223> OTHER INFORMATION: primer

<400> SEQUENCE: 58
cgggagctcc tgtgcaaatt gttgcgcaca t                  31

<210> SEQ ID NO 59
<211> LENGTH: 41
<212> TYPE: DNA
<213> ORGANISM: Artificial Sequence
<220> FEATURE:
<223> OTHER INFORMATION: primer

<400> SEQUENCE: 59 ccttttttcgt tctggtccga gacgcatttc cctatgttga g       41

<210> SEQ ID NO 60
<211> LENGTH: 41
<212> TYPE: DNA
<213> ORGANISM: Artificial Sequence
<220> FEATURE:

```
<223> OTHER INFORMATION: primer

<400> SEQUENCE: 60
ctcaacatag ggaaatgcgt ctcggaccag aacgaaaaag g                            41

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
cggtctagag cgccctgcaa cgactgctgt t                                      31

<210> SEQ ID NO 62
<211> LENGTH: 24
<212> TYPE: DNA
<213> ORGANISM: Artificial Sequence
<220> FEATURE:
<223> OTHER INFORMATION: primer

<400> SEQUENCE: 62
gaattcgaac aggaagaact gctg                                              24

<210> SEQ ID NO 63
<211> LENGTH: 34
<212> TYPE: DNA
<213> ORGANISM: Artificial Sequence
<220> FEATURE:
<223> OTHER INFORMATION: primer

<400> SEQUENCE: 63
cggaagcttg gatccaatgg cactcagaat atca                                   34

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
ggatccggtg gcggcggtag cg                                                22

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
aagcttttaa tggtgatgat gatg                                              24
```

SELF-ADJUVANTING *YERSINIA* OUTER MEMBRANE VESICLE AS A VACCINE AGAINST PLAGUE, ANTHRAX AND PSEUDOMONAS INFECTION

CROSS-REFERENCE TO RELATED APPLICATIONS

This application is a continuation of U.S. Non-Provisional application Ser. No. 17/117,417, filed on Dec. 10, 2020, and which claimed priority to U.S. Provisional App. No. 62/947,585 filed on Dec. 13, 2019.

STATEMENT REGARDING FEDERAL SPONSORED RSEARCH

This invention was made with government support under R21 AI139703 awarded by the National Institutes of Health. The government has certain rights in the invention.

BACKGROUND OF THE INVENTION

1. Field of the Invention

The present invention relates to genetically engineered bacteria that are used to generate self-adjuvanting outer membrane vesicles (OMVs) encasing protective antigens from *Y. pestis, Bacillus anthracis*, and *Pseudomonas aeruginosa* for use as vaccines.

2. Description of the Related Art

Recent reports concerning the taxonomy of the genus *Yersinia* show it consists of 17 species, among which only three of 11 currently recognized species are human pathogens: *Yersinia enterocolitica, Yersinia pseudotuberculosis,* and *Yersinia pestis*.

*Yersinia pestis* is the etiological agent of plague, which is one of the most feared infectious disease in human history and responsible for more than 200 million deaths. Plague remains a public health concern in contemporary era, and is responsible for several thousand annual human cases worldwide. In 2015, 15 human cases of plague were reported in the US, resulting in 4 deaths and, in 2017, the island of Madagascar experienced a large outbreak of plague, where a total of 2348 cases of plague (~70% are pneumonic form), including 202 deaths (case fatality rate: 8%), which incited regional panics. Pneumonic plague, the most dangerous form, rapidly progresses to death in 48 to 72 hours if antibiotic treatment is delayed beyond 24 hours, and also can be transmitted person-to-person via aerosol. Treatment of plague is dependent upon antibiotics which are currently effective for post-exposure mitigation of disease; however, *Y. pestis* strains resistant to eight antibiotics have been isolated from plague patients in Madagascar. Moreover, recent isolates from Mongolia corroborated the existence of naturally occurring, multi-drug resistant variants of *Y. pestis*. For longer-term protection and to counter drug-resistance *Y. pestis* occurring, vaccination is believed to be an efficient way (14, 15).

Recently, the main focus of plague vaccine research has been to develop subunit vaccines, in particular targeting LcrV and F1 antigens, which were found to efficiently protect rodent and cynomolgus macaque against bubonic and pneumonic plague and are well tolerated in humans. However, the subunit vaccine had insufficient and highly variable protection against pneumonic plague in African Green monkeys.

In order to improve efficacy of subunit vaccines, nanotechnology platforms have been employed to overcome the weak immunogenicity and intrinsic in vivo instability. A novel biodegradable polyanhydride nanoparticle-encapsulated with F1-LcrV vaccine could induce long-lasting mature antibody responses and protective immunity against pneumonic plague. Immunization with the bacteriophage T4 DNA nanoparticles carrying F1-LcrV elicited robust antibody and cellular immune responses and provided complete protection to mice and rats against intranasal challenge with high doses of *Y. pestis* CO92. Thus, Nano-antigen delivery platforms may provide a novel strategy to generate efficacious plague vaccines. However, isolation of virulent F1-negative *Y. pestis* strains from natural sources and the existence of LcrV polymorphisms in *Yersinia* may result in *Y. pestis* variants that escape protective immunity induced by LcrV and F1 antigens. Therefore, vaccines solely based upon LcrV and F1 antigens may be insufficient to guarantee long-term defense against plague in humans.

One critical strategy used by *Y. pestis* to evade host immune responses is to produce a tetra-acylated form of lipid A at 37° C. that is not recognized by Toll-like receptor 4 (TLR4) due to absence of LpxL (lauroyltransferase). Although *Y. pestis* is capable of synthesizing stimulatory hexa-acylated lipid A due to presence of LpxP (palmitoleoyltransferase), its activity is dependent on low temperature (26° C.). In human PBMCs, activation induced by LPS from *Y. pestis* grown at 26° C. and LPS from *Escherichia coli* was significantly inhibited by LPS from *Y. pestis* grown at 37° C. synthesizing tetra-acylated lipid A. The ΔlpxP32::$P_{lpxL}$ lpxL mutation was introduced, which deletes the lpxP gene and inserts *E. coli* lpxL into the chromosome of *Y. pestis* KIM6+ to create strain χ10015, which produces hexa-acylated lipid A at both 26° C. and 37° C. Strain χ10015(pCD1Ap), into which the pCD1Ap virulence plasmid was introduced, was highly attenuated by subcutaneous (s.c.) administration. However, mice s.c. immunized with χ10015(pCD1Ap) had significant reactogenicity due to the toxic hexa-acylated lipid A. Subsequently, strain χ10027 (ΔlpxP32::$P_{lpxL}$ lpxL ΔlacI23::$P_{lpp}$ lpxE) was constructed that heterologously expresses the lpxE gene encoding the lipid A 1-phosphatase from *Francisella novicida* in *Y. pestis*, predominantly yielding 1-dephosphorylated hexa-acylated lipid A (Monophosphoryl Lipid A, MPLA), when χ10027 was grown at both 26° C. and 37° C. MPLA isolated from strain χ10027 (ΔlpxP32::$P_{lpxL}$ lpxL ΔlacI23::$P_{lpp}$ lpxE) exhibited a significant reduced capacity to activate HEK293 cells/TLR4-MD2 and other mammalian cells in vitro, in comparison with lipid A from χ10015. MPLA is an endotoxin derivative that has been approved by US and European authorities as a vaccine adjuvant in humans and exhibits potent adjuvant activity but is 100- to 10,000-fold less toxic than native lipid A (biphosphoryl lipid A). The attenuated toxicity of MPLA is associated with reduced induction of proinflammatory cytokines such as tumor necrosis factor alpha (TNF-α), interleukin-1β (IL-1β), and gamma interferon (IFN-γ) during initial exposure. Thus, OMVs isolated from the genetically modified χ10027 strain would retain high immunostimulatory activity whilst diminishing toxicity.

*Y. pseudotuberculosis* is thought to be the direct evolutionary ancestor of *Y. pestis*. The two species diverged from one another 2,600-28,000 years ago. With the exception of two additional plasmids carried by *Y. pestis* (pPCP1 and pMT1), the two species share >95% genetic identity and a common virulence plasmid with a conserved colinear backbone. Blast analysis of several major *Y. pestis* antigens shows that LcrV shares 96% amino acid identity between the two species, additional antigens, Psn, Ail (OmpX) and YadC shown to be protective against *Y. pestis* challenge share 100% and >97%, respectively. Although *Y. enterocolitica* is a distant species to *Y. pestis/Y. pseudotuberculosis* in phylogenetical tree, they still share many homologous genes by entire genomic analysis. Currently, there are no effective vaccines to prevent *Y. pestis* infection in humans.

*Bacillus anthracis*, the causative agent of anthrax, is a Gram-positive, spore-forming bacilli that causes bacteremia and toxemia in its systemic form through an array of virulence factors. Human anthrax results from contact with infected animals, contaminated animal products, or after exposure to accidentally or intentionally released spores of *B. anthracis*. Anthrax have three types of clinical forms: cutaneous, gastrointestinal and pulmonary. Each type can progress to fatal systemic anthrax, but untreated pulmonary anthrax acquired by inhalation is the most severe form. Pulmonary anthrax has a mortality as high as 100% if no interventions in time and 45% with treatment. The development of anthrax as a biological weapon by several foreign countries has been documented. In North America, human cases of anthrax are infrequent. However, *B. anthracis* sent through the United States Postal Service (USPS) caused 22 cases of anthrax, including 5 deaths In 200, which poses huge public panics in US. Because spores of *B. anthracis* are so resistant to destruction and can be easily spread by release in the air coupled with high rates of mortality, *B. anthracis* is considered as an agent with potential biological terrorism threat by the United States military and also classified as a Tier-1 biothreat agent by CDC.

The current anthrax vaccines are approved for pre-exposure and post-exposure prophylaxis of disease in person at high-risk of exposure and for persons with suspected or confirmed exposure in conjunction with antibiotics, respectively. Both vaccines prepared from crude cultures of different *B. anthracis* strains contained protective antigen (PA) and residual amounts of anthrax toxins lethal factor (LF) and edema factor (EF) that causes certain adverse reactions and use limitations. Moreover, vaccination regimen requiring many priming and booster doses and shelf-life limitation due to the instability of the PA, are challenging widespread use of these vaccines. Alternative means have been studied to address the limitations of current anthrax vaccines via various particulate systems including polymeric nano/microparticles, nanoemulsions, and liposomes to deliver protective antigens of *B. anthracis*. The valuation for anthrax vaccines market was $465.5 million in 2018, and it is expected to reach $863.7 million by 2026.

*Y. pestis* and *B. anthracis* are both etiological agents for worldwide zoonotic diseases and are considered among the most feared potential bioterror agents. Their natural outbreak or malicious dissemination can cause widespread panics as recent Ebola outbreaks in West Africa, resulting in huge economic and social collapse on a global scale. Therefore, it is imperative to develop a vaccine that can elicit concerted protective immunity against both pathogens with spared doses and short-term immunization regimens. Also, stockpiling a such vaccine would be extremely valuable in protecting the general public against potential biological threats. Recently the brand name of the 6-in-1 vaccine, Infanrix Hexa, which stands for 'Diphtheria, Tetanus, acellular Pertussis, Hib, Hepatitis B and Inactivated Polio Vaccine, was used in the UK to reduce the number of injections a child needs (http://vk.ovg.ox.ac.uk/6-in-1-vaccine), which provides a proof of concept fora two-in-one vaccine for plague and anthrax.

*P. aeruginosa* (PA) is a Gram-negative bacterium that is widely found in the environment e.g. soil, water and other moist locations and is an opportunistic pathogen that takes advantage of an individual's compromised immune system to establish an infection. In the hospital setting, PA is one of the leading pathogens responsible for pneumonia, surgical infection, bacteremia and other life-threatening infections worldwide. This bug is most problematic to those long-term hospitalized patients in intensive care units and burn victims. U.S. CDC reports showed that PA was the most commonly isolated gram-negative pathogen in ventilator-associated pneumonia (VAP) in 2009-2010 and was the second most common pathogen overall, accounting for 11% of total cases. The VAP caused by PA contributes to a mortality rate as high as 13.5%. PA infection in burn patients can quickly develop a systemic infection with a mortality rate ranging from 38% to 70%. PA is also a leading cause of life-threatening infections in immunocompromised hosts with underlying diseases such as cancer or AIDS. In addition, cystic fibrosis (CF) patients highlighting mucus accumulation, are frequent and persistent bacterial infection causing chronic inflammation of the lungs. This abundance of microbes colonizing the respiratory tract, and particularly the lower airways, is facilitated by thick airway mucus and deficient mucociliary clearance in CF patients. Among these microbes, PA, a dominant airway pathogen, chronically infects up to 60-75% of adult CF patients, causes decline of lung function and is strongly associated with mortality increase. PA has a complex gene regulation network including hundreds of genes that can facilitate bacterium rapidly adapted to different environments, resulting in its intrinsic resistance to treatment of antibiotics. Recent studies report that the resistance rates of PA are increasing in many parts of the world. Multi-drug-resistant (MDR) and extreme drug-resistant (XDR) high-risk strains are widespread in healthcare settings, causing extreme challenges for PA treatment. To combat the spread of PA infection, vaccination against PA would be an effective means to eliminate or reduce the need of antibiotic agents that result in problems of antibiotic resistance.

Nanocarrier-based delivery systems facilitate uptake by phagocytic cells, the gut-associated lymphoid tissue, or the mucosa-associated lymphoid tissue, leading to efficient antigen recognition and presentation, thereby offering an opportunity to enhance the humoral and cellular immune responses. Outer membrane vesicles (OMVs) are nanosized lipid vesicles released by a diverse range of Gram-negative bacteria that are enriched in protein, polysaccharide, DNA/RNA and lipid microbial components, including plentiful potent immunogens. OMVs typically range between 20-200 nm, readily enabling entry into lymph vessels and uptake by antigen presenting cells. By retaining composition of the pathogen antigenic surface, OMVs elicit innate immunity as well as prime humoral and cell-mediated immune responses. A licensed OMV vaccine against *Neisseria meningitides* has been proven safe and protective in humans. OMVs provide an economically favorable vaccine platform as a result of inexpensive preparation and high stability. Furthermore, OMVs encase a broad spectrum of immunogens, providing the theoretical advantages of simultaneously priming immunity against many antigens and thereby reducing the likelihood of antigen circumvention. *Yersinia* could produce and release native OMVs under physiological conditions. Therefore, the genetically modified *Yersinia* strain producing an adjuvant formed lipid A (MPLA) and synthesizing multiple protective antigens from *Y. pestis* and *B. anthracis* is used to generate self-adjuvanting nanoparticles (OMVs). Immunization with the self-adjuvanting OMVs would offer premium protection against two deadly agents simultaneously.

SUMMARY OF THE INVENTION

The invention comprises certain *Y. pestis* mutant constructions that can produce highly immunogenic self-adjuvanting OMVs. Intramuscular immunization with OMVs from these constructions affords significant protection against three pathogenic *Yersinia* species, *Y. pestis, Y. enterocolitica*, and *Y. pseudotuberculosis* in mice.

Some embodiments of the invention include: (1) heterologously expresses the lpxE gene encoding the lipid A 1-phosphatase from *Francisella novicida* in the lpxL inserted the *Y. pestis* construction, predominantly yielding 1-dephosphorylated hexa-acylated lipid A (Monophosphoryl Lipid A, MLPA) to generate self-adjuvanted OMVs which deliver innate signals through TLR ligands to induce *Yersinia*-specific T-cell and B-cell immunity. (2) highly secret prominent protective antigens LcrV into periplasm of bacteria by Type Two Secretion System (T2SS); (3) Remove virulence factors [Yops, Pla and Ymt (murine toxin)] that are immunosuppressive or otherwise interfere with protective immune responses; and (4) disrupt tolR, yrbE, lpp or nlpI (y0695) genes in a *Y. pestis* construction to highly increase OMV production.

The invention provides OMVs from a genetically modified *Y. pestis* strain that can be used to express heterologous antigens (such as *B. anthracis* protective antigens), wherein the OMVs are able to encase heterologous antigens from heterologous pathogens.

The invention comprises a *Y. pseudotuberculosis* PB1+ strain, a progenitor of *Y. pestis*, that can be incorporated different mutations, such as, lpxE, tolR, yrbE, lpp, nlpI (YPTS_0515), asd or the caf operon to synthesize *Y. pestis* F1 antigen in a *Y. pseudotuberculosis* strain. The genetically modified *Y. pseudotuberculosis* strain (YptbS44, Table 4) can produce high amounts of immunogenic OMVs containing homologous and heterologous protective antigens of *Y. pestis, B. anthracis* or other pathogens.

OMVs produced by genetically modified *Y. pestis* or *Y. pseudotuberculosis* constructions provide the advantage of simultaneously priming humoral and cellular immune responses against many *Yersinia* homologous surface antigens, thereby greatly enhancing the likelihood of broad-based protection against plague caused by *Y. pestis* and Yersiniosis caused by *Y. pseudotuberculosis* and *Y. enterocolitica*.

The invention comprises the genetically modified *Y. pseudotuberculosis* strain that can produce high amounts of immunogenic OMVs containing heterologous protective antigens of *P. aeruginosa* (PcrV and HitA).

The invention comprises the genetically modified *P. aeruginosa* strain (can produce high amounts of immunogenic OMVs containing heterologous protective antigens of *P. aeruginosa* (PcrV and HitA).

The invention comprises a *Y. enterocolitic* strain, a close relative of *Y. pestis*, that can incorporate different mutations, such as, lpxE, tolR, yrbE, lpp, nlpI, asd or the caf operon to synthesize *Y. pestis* F1 antigen in a *Y. enterocolitic* strain. The genetically modified *Y. enterocolitic* strain can produce high amounts of immunogenic OMVs containing homologous and heterologous protective antigens of *Y. pestis, B. anthracis* or other pathogens.

Immunization with OMVs trapped homologous or heterologous antigens from genetically modified *Y. pestis, Y. pseudotuberculosis, Y. enterocolitic* or *Pseudomonas aeruginosa*. strains can induce significant protective immunity against pathogenic *Yersinia* spp., *B. anthracis, Salmonella* spp., *P. aeruginosa, Klebsiella pneumoniae*, or other pathogens. Also, OMVs can be administrated by intradermal, intranasal or oral route to induce mucosal immunity.

BRIEF DESCRIPTION OF THE SEVERAL VIEWS OF THE DRAWING(S)

Figure 1C:
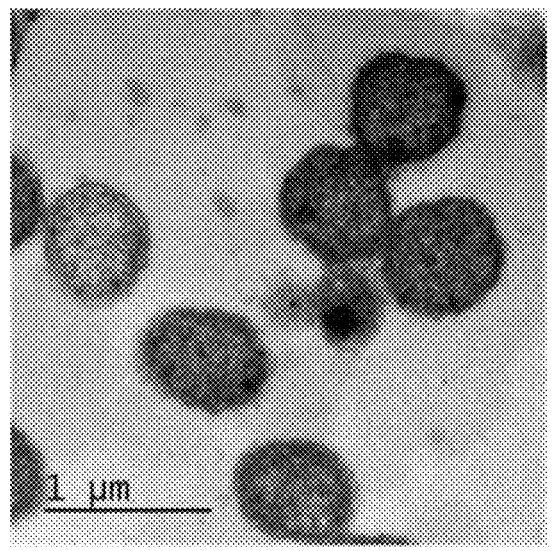
Figure 1C:
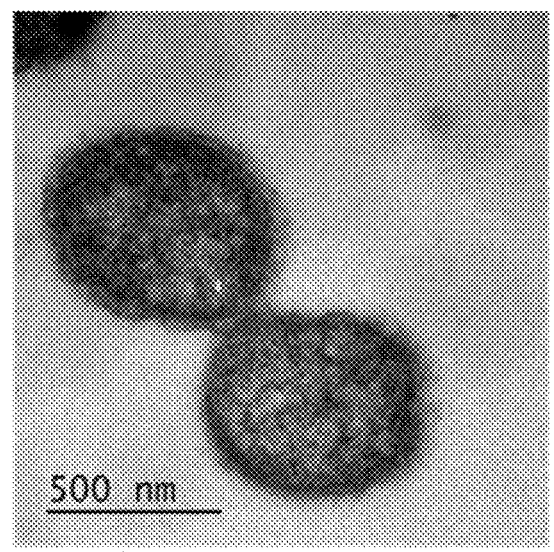

The present invention will be more fully understood and appreciated by reading the following Detailed Description in conjunction with the accompanying drawings, in which:

Figure 1A:
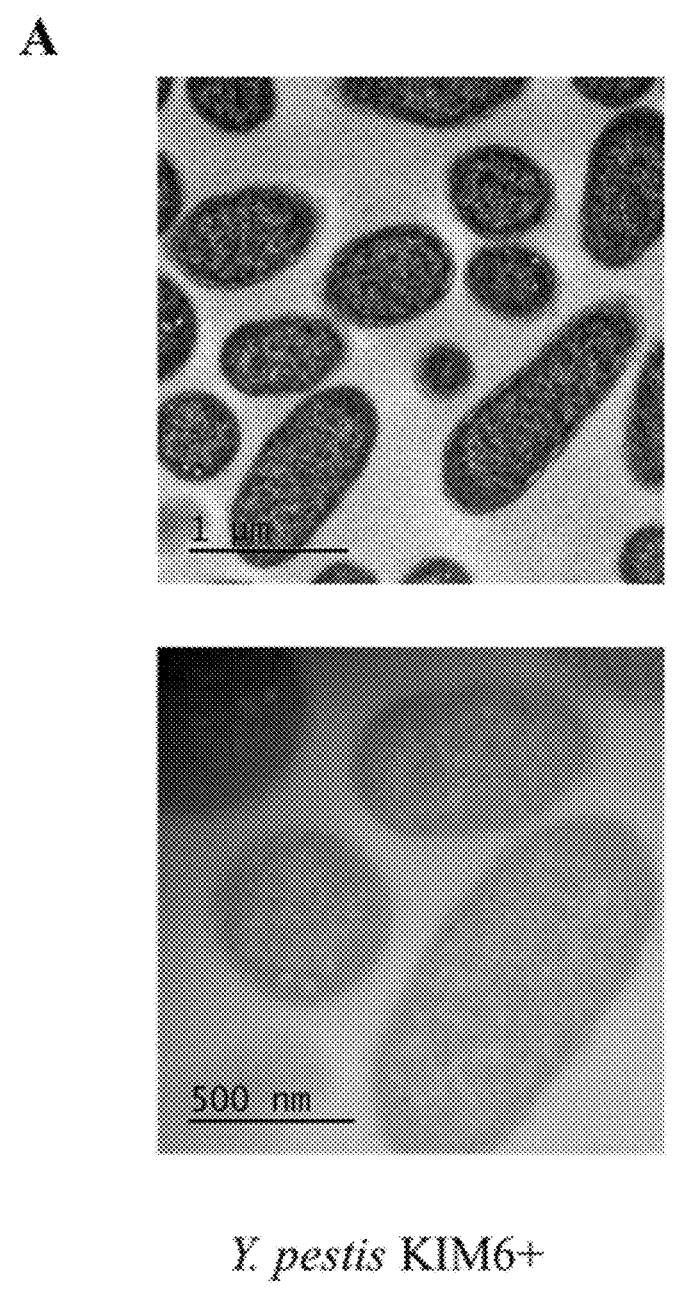

FIG. 1A through FIG. 1C are comparisons of morphological alterations in *Y. pestis* strains by TEM imaging, where: FIG. 1A is *Y. pestis* KIM6+. FIG. 1B is χ10015 (ΔlpxP:: $P_{lpxL}$lpxL). FIG. 1C is χ10027 (ΔlpxP:: $P_{lpxL}$lpxL ΔlacZ:: $P_{lpp}$lpxE). The samples were prepared by conventional staining with 1% aqueous uranyl acetate as described in the Materials and Methods. Bars, 1 μm and 500 nm. The results are representative of three repeated experiments.

Figure 2A:
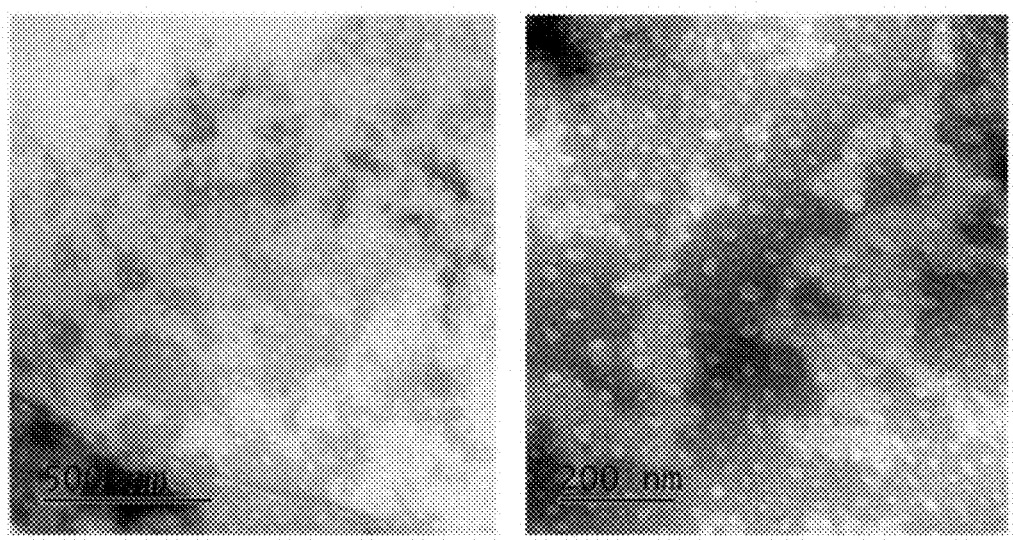
Figure 2B:
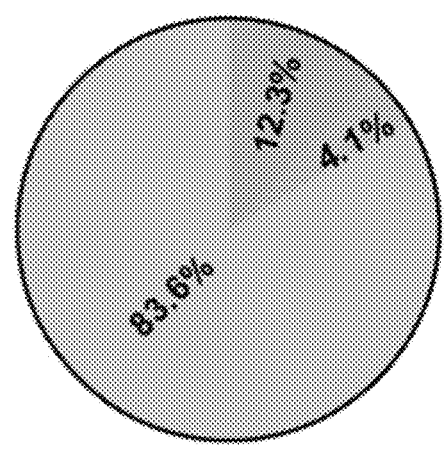
Figure 2C:
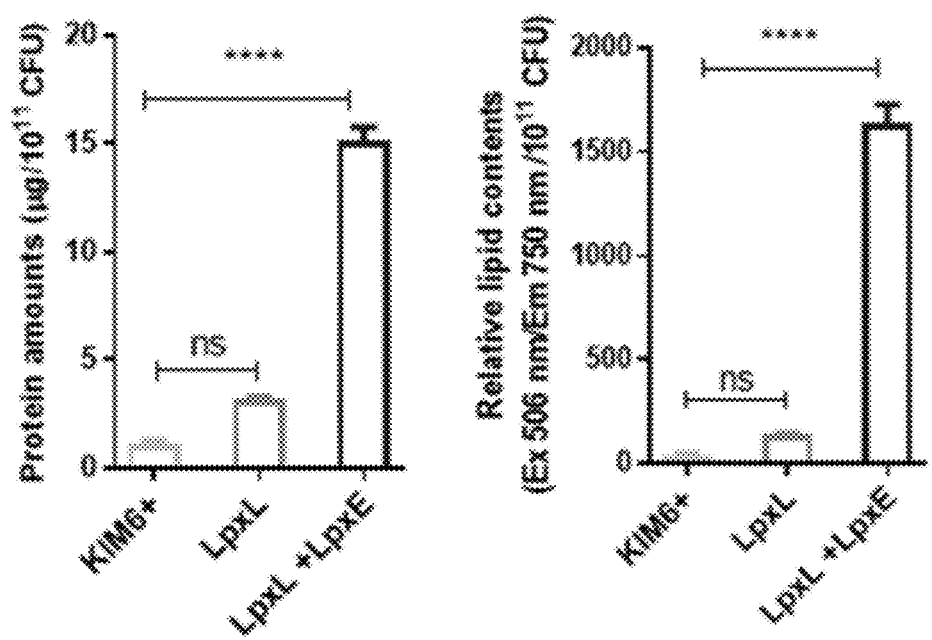
Figure 2D:
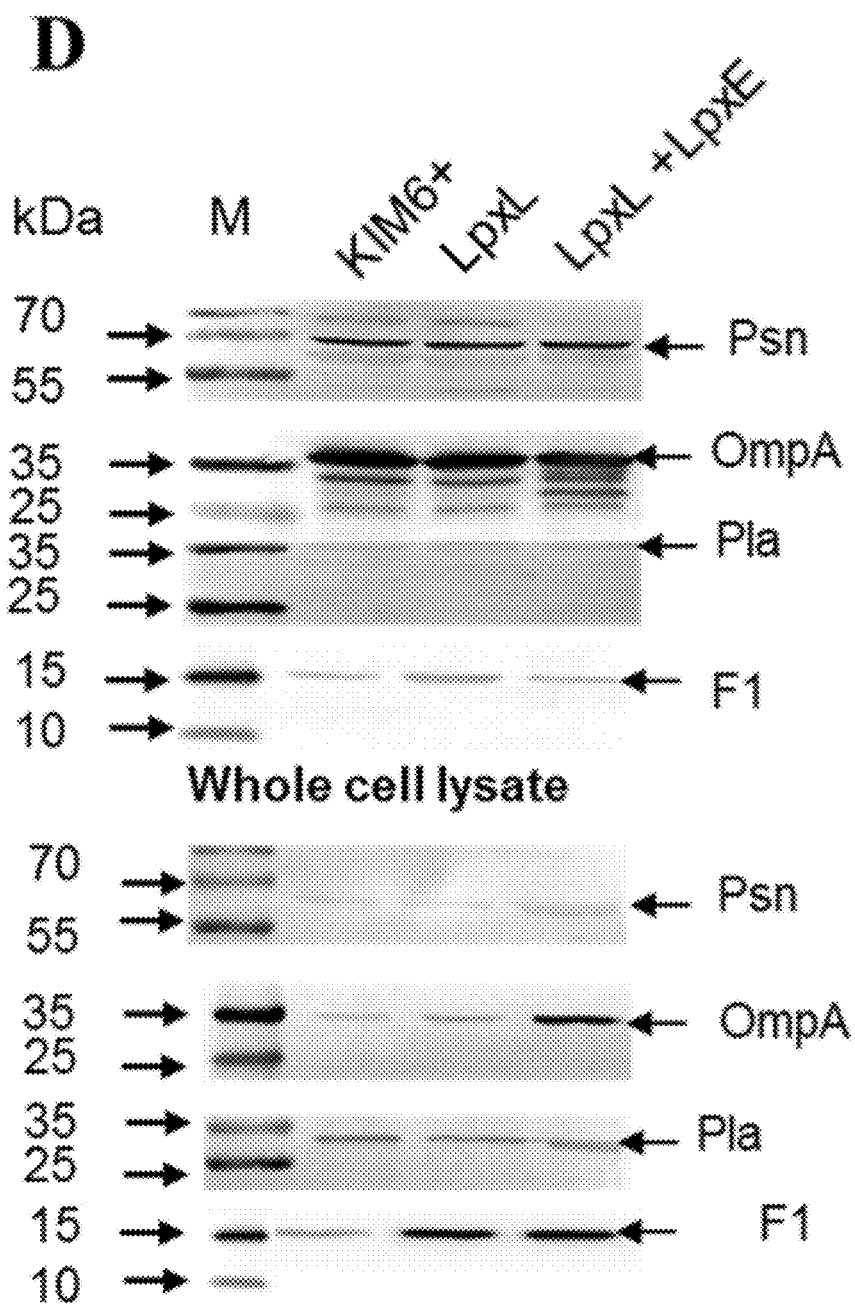
Figure 2E:
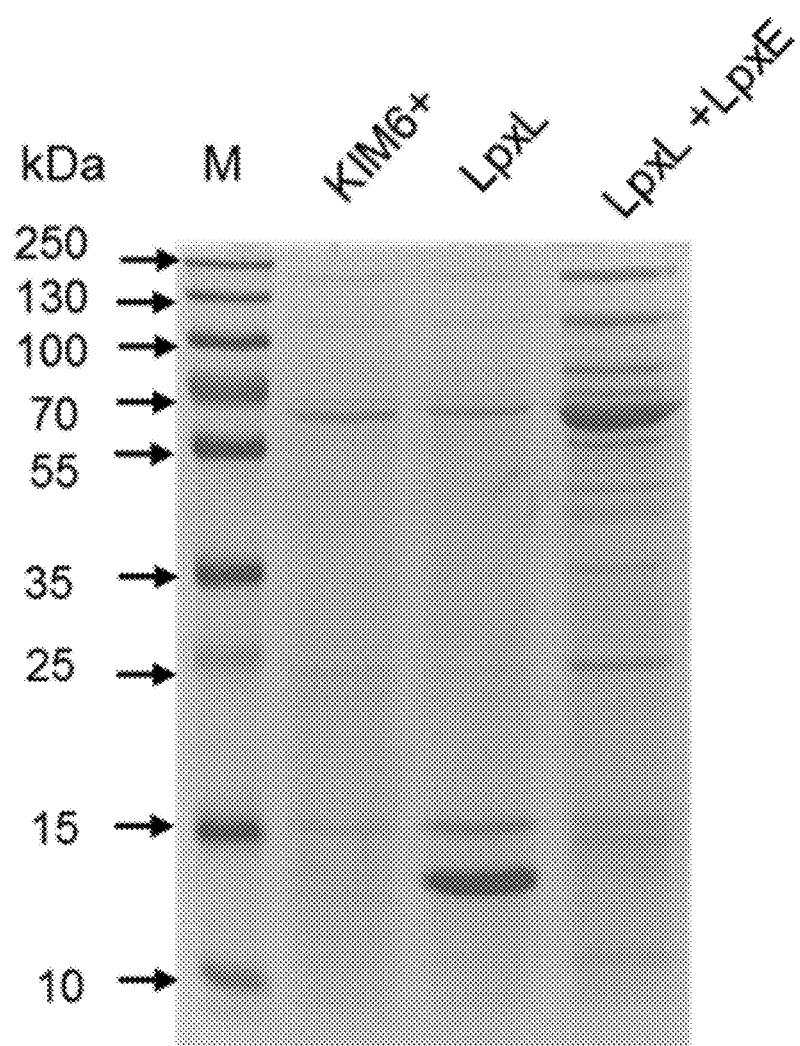

FIGS. 2A through 2E are an analysis of *Y. pestis* outer membrane vesicles (OMVs). FIG. 2A—TEM of OMVs purified from *Y. pestis* KIM6+ culture supernatants. Bars, 500 nm and 200 nm. FIG. 2B—Subcellular distribution of proteins presents in *Y. pestis* KIM6+ OMVs as a percentage of the total proteins identified by mass spectrometry listed in Table 2. FIG. 2C—Amounts of protein and relative lipid contents in OMVs purified from different *Y. pestis* strains [*Y. pestis* KIM6+, ×10015 (ΔlpxP:: $P_{lpxL}$lpxL) and χ10027 (ΔlpxP::$P_{lpxL}$lpxL ΔlacZ:: $P_{lpp}$lpxE)]. All the values were normalized according to the total bacterial number (×10$^{11}$ CFU). FIG. 2D—Whole cell lysates or OMVs isolated from *Y. pestis* KIM6+, ×10015 and χ10027 were examined for the presence of the outer membrane proteins Psn, OmpA, Pla, and Caf1(F1) by immunoblotting. FIG. 2E—Whole protein profiles of OMVs from different *Y. pestis* strains as shown in an SDS-PAGE gel. The results are representative of three experiments. Statistical significance: ns, no significance; ****, P<0.0001.

Figure 3A:
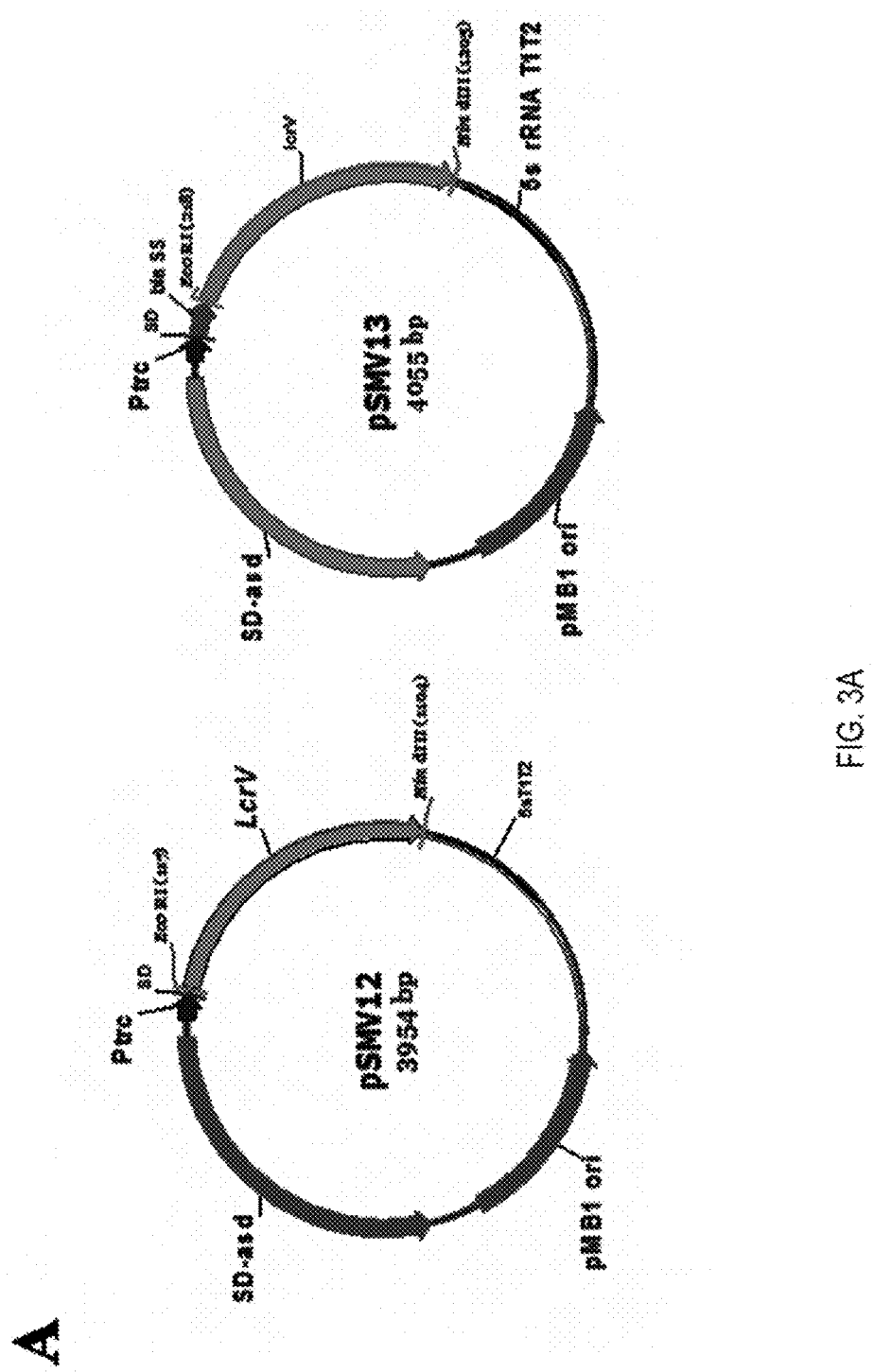
Figure 3B:
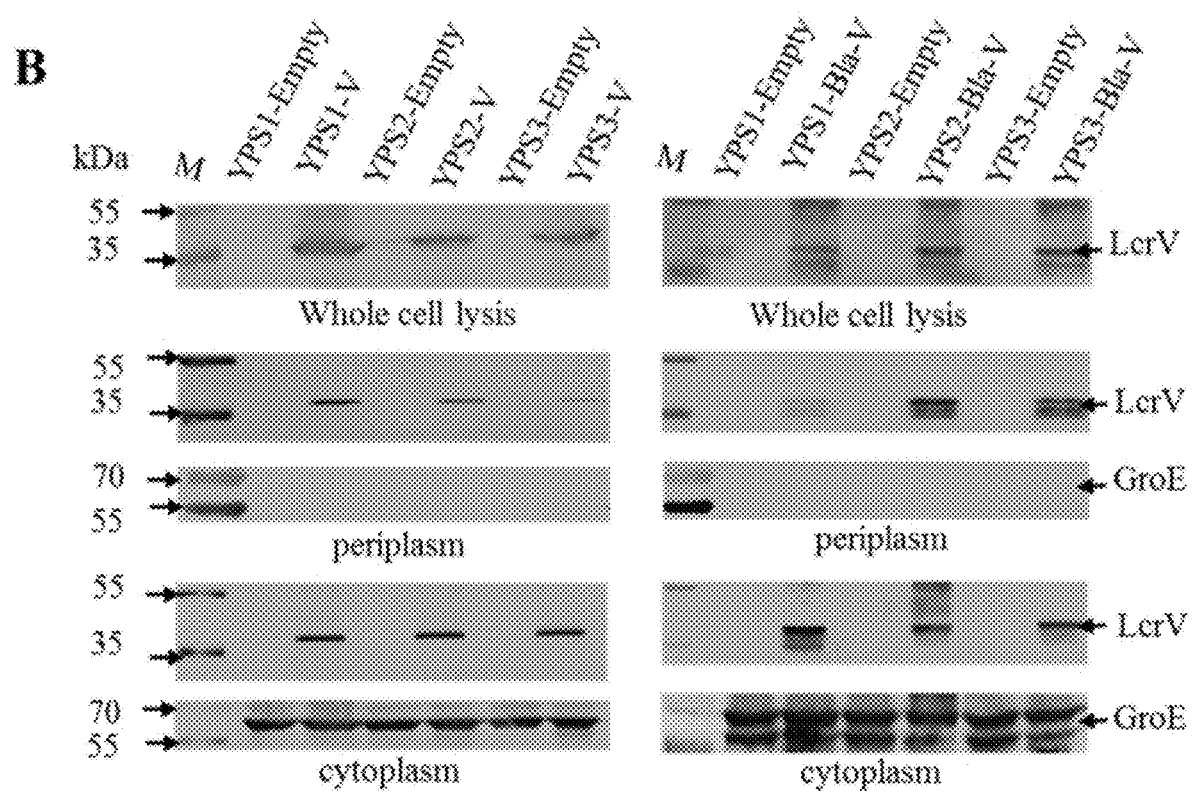
Figure 3C:
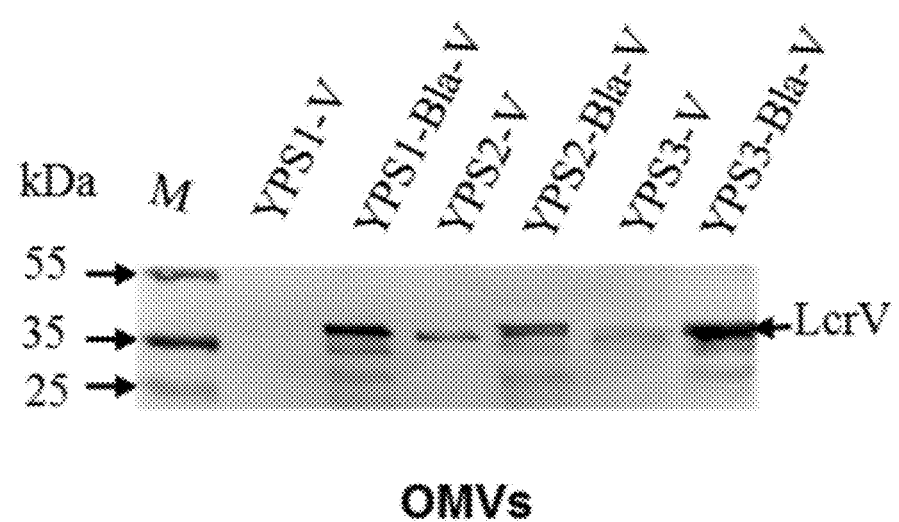
Figure 3D:
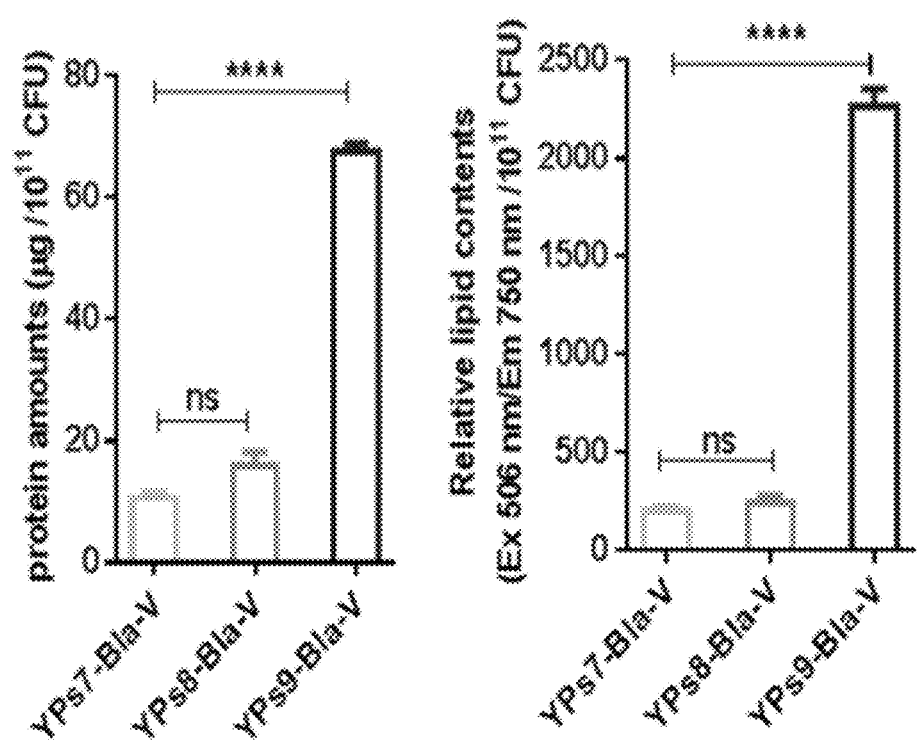

FIGS. 3A through 3F are a subcellular location analysis of the oversynthesis of LcrV antigen in *Y. pestis* mutants. FIG. 3A—Physical maps of the Asd+ plasmids pSMV12, harboring the native lcrV gene of *Y. pestis*, and pSMV13, harboring the N-terminal β-lactamase signal sequence (bla ss) and lcrV fusion to facilitate LcrV secretion by the T2SS. FIG. 3B—Comparison of LcrV amounts in different cell fractions. The total cell lysates and subcellular fractions, including the cytoplasmic and periplasmic fractions, were prepared from YPS1, YPS2 and YPS3 strains individually harboring pYA3342 (an empty plasmid), pSMV12 or pSMV13 (Table 1). The cells were grown in HIB broth at 28° C. for 14 h and then incubated at 37° C. for 4 h, as described in the Supplementary Information Materials and Methods. Fractions with 25 μl volumes from cultures grown to an OD$_{600}$ of 0.8 were evaluated by immunoblotting with LcrV-specific polyclonal rabbit antibody. GroEL was used as a cytoplasmic marker for fractionation. FIG. 3C—Comparison of the LcrV amounts in the OMV fractions isolated from YPS1, YPS2 and YPS3 strains individually harboring pSMV12 or pSMV13 (Table 1). OMVs were isolated from bacterial cultures as described in the Materials and Methods. Five-microliter volumes of OMVs normalized according to the bacterial numbers were evaluated by immunoblotting with LcrV-specific polyclonal rabbit antibody. FIG.

Figure 3E:
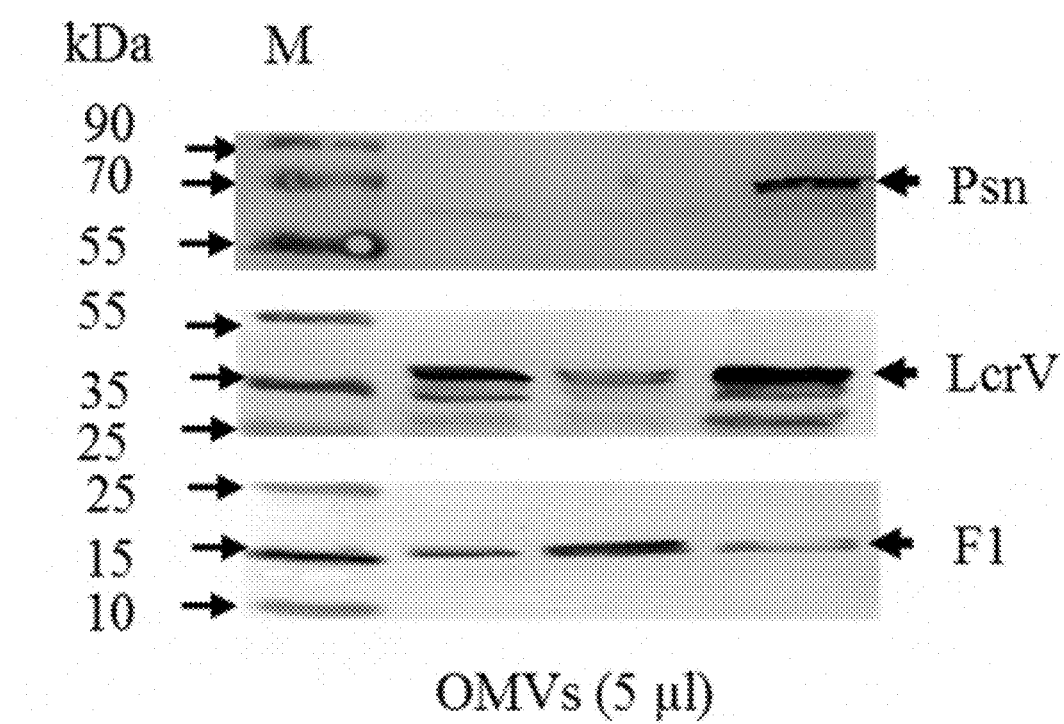
Figure 3F:
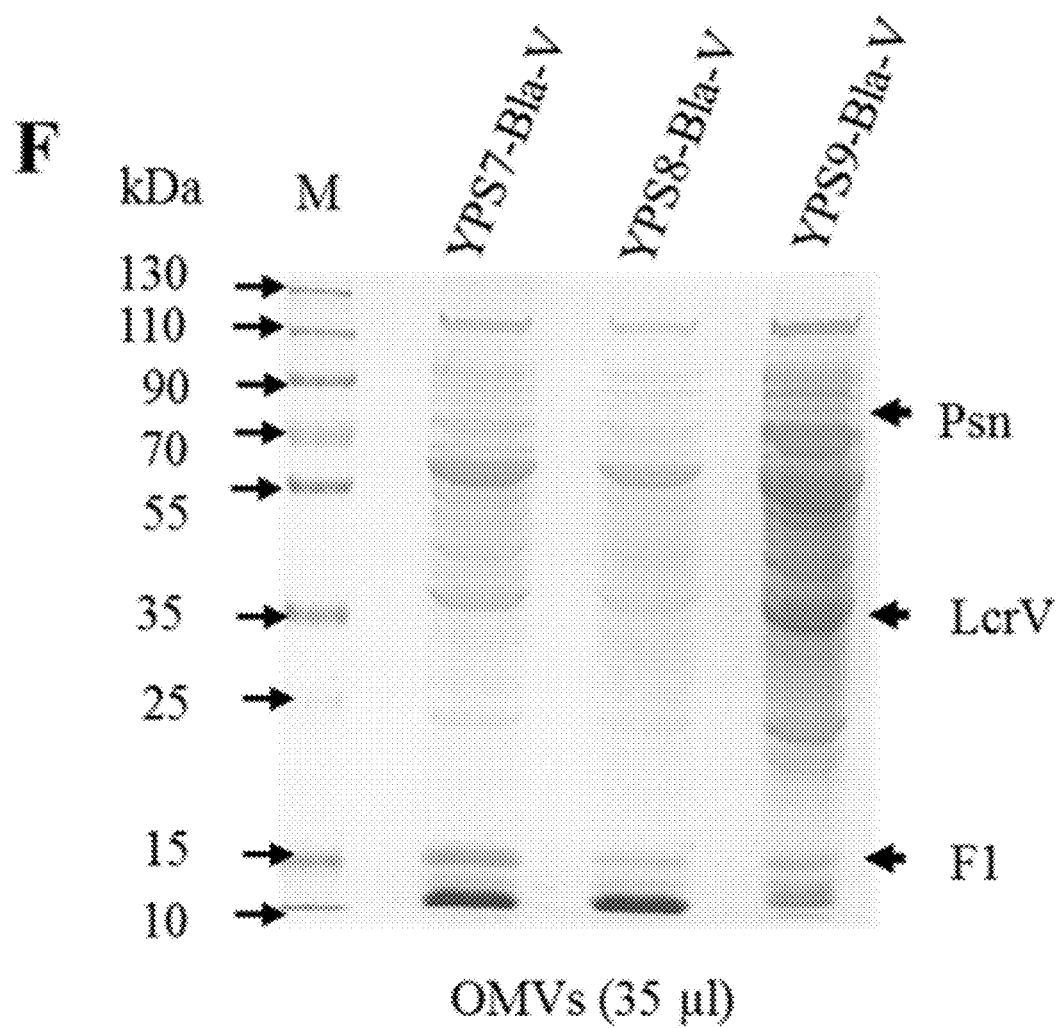

3D—Amounts of protein and relative lipid contents in OMVs purified from YPS1, YPS2 and YPS3 strains individually harboring pSMV13. All the values were normalized according to the total bacterial numbers ($\times 10^{11}$ CFU). FIG. 3E—Comparison of Psn, LcrV and F1 synthesis in the OMV fractions isolated from YPS1, YPS2 and YPS3 strains individually harboring pSMV13. FIG. 3F—Whole protein profiles of OMVs from YPS1, YPS2 and YPS3 strains individually harboring pSMV13 were examined by SDS-PAGE gels. The results are representative of three experiments. Statistical significance: ns, no significance; ****, P<0.0001

Figure 4A:
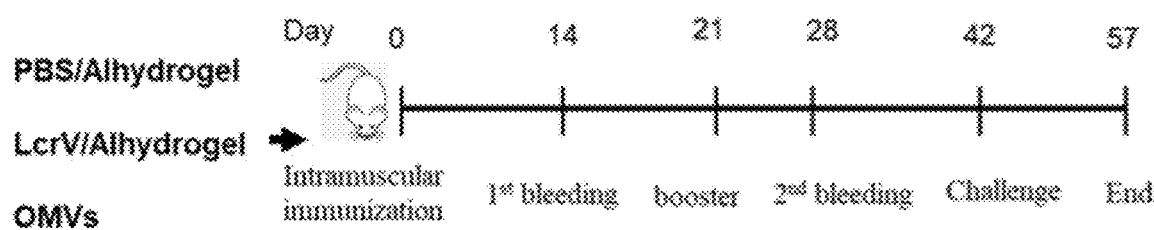
Figure 4B:
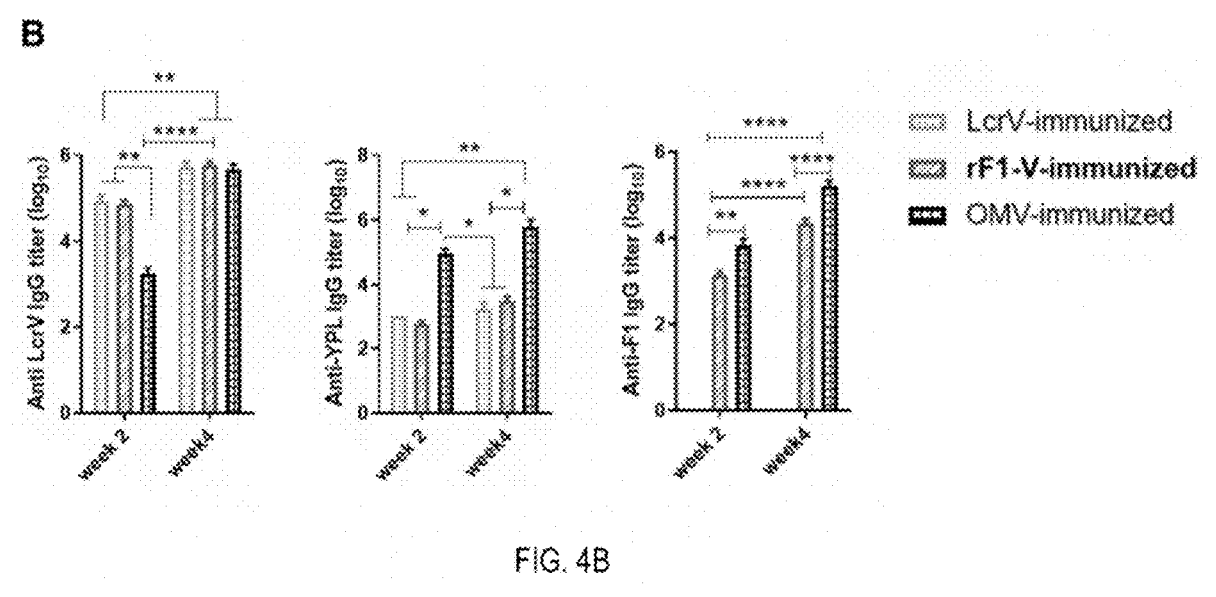
Figure 4C:
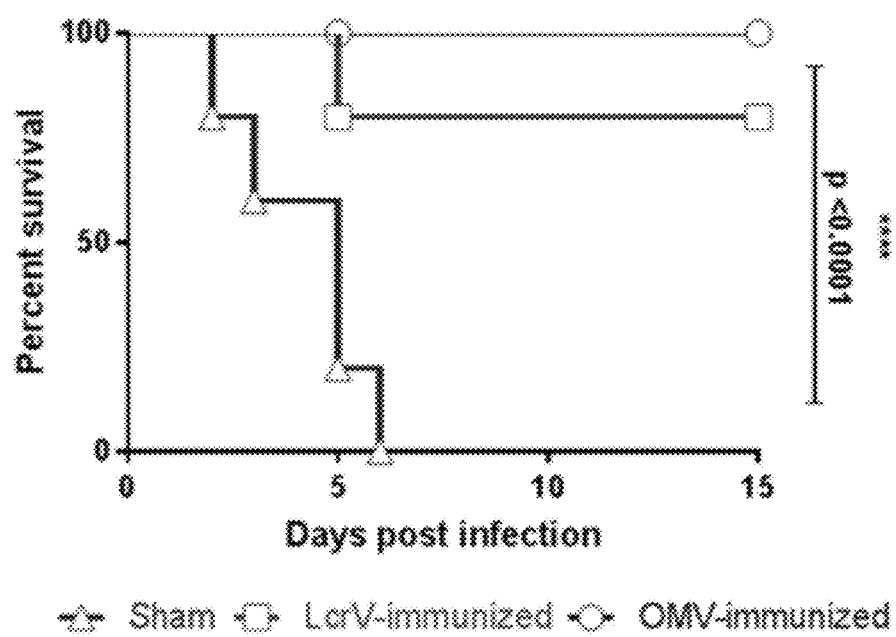
Figure 4D:
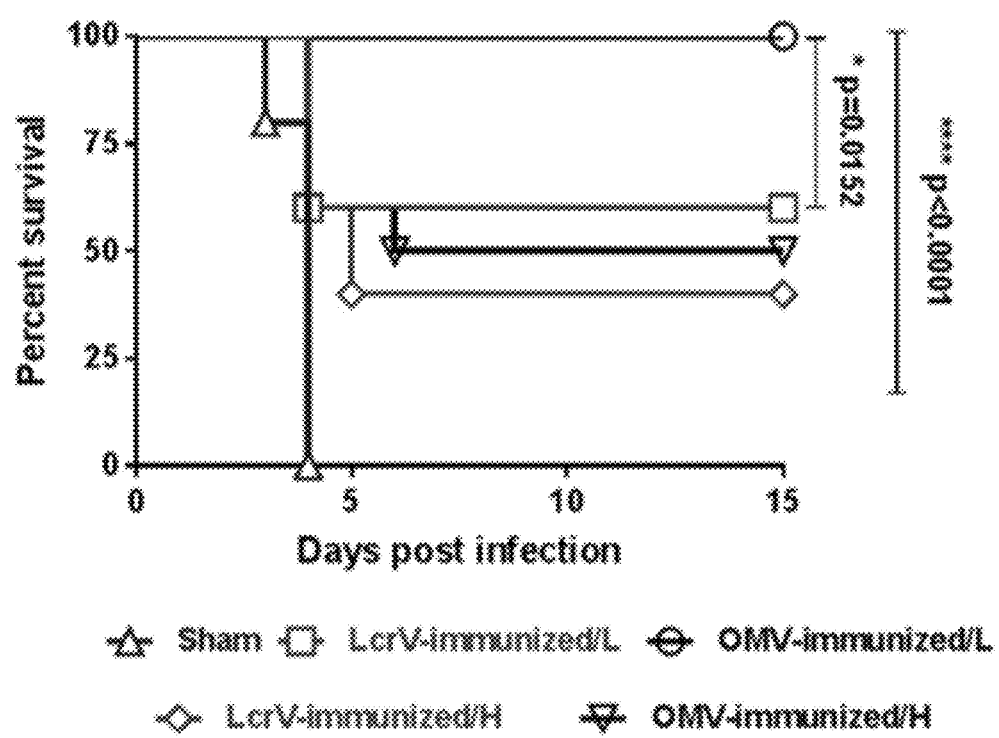

FIG. 4A though FIG. 4D are an analysis of total IgG titers in LcrV- or OMV-immunized mice and the survival of mice challenged by virulent *Y. pestis*. FIG. 4A—Immunization scheme used for the mouse study. FIG. 4B—LcrV, YPL (*Y. pestis* whole cell lysate) and F1-specific total IgG titers. FIG. 4C—Immunized and PBS (sham) groups of Swiss-Webster mice (10 mice per group, equal numbers of males and females) were subcutaneously challenged with $8 \times 10^5$ CFU of *Y. pestis* KIM6+(pCD1Ap) ($8 \times 10^4$ $LD_{50}$). FIG. 4D—Immunized and PBS (sham) groups of Swiss-Webster mice (10 mice per group, equal numbers of males and females) were intranasally challenged with a low dose (L: $5 \times 10^3$ CFU, 50 $LD_{50}$) or a high dose (H: $5 \times 10^4$ CFU, 500 $LD_{50}$) of *Y. pestis* KIM6+(pCD1Ap). Statistical significance: *, P<0.05;  P<0.01; * P<0.001, **** P<0.0001.

Figure 5A:
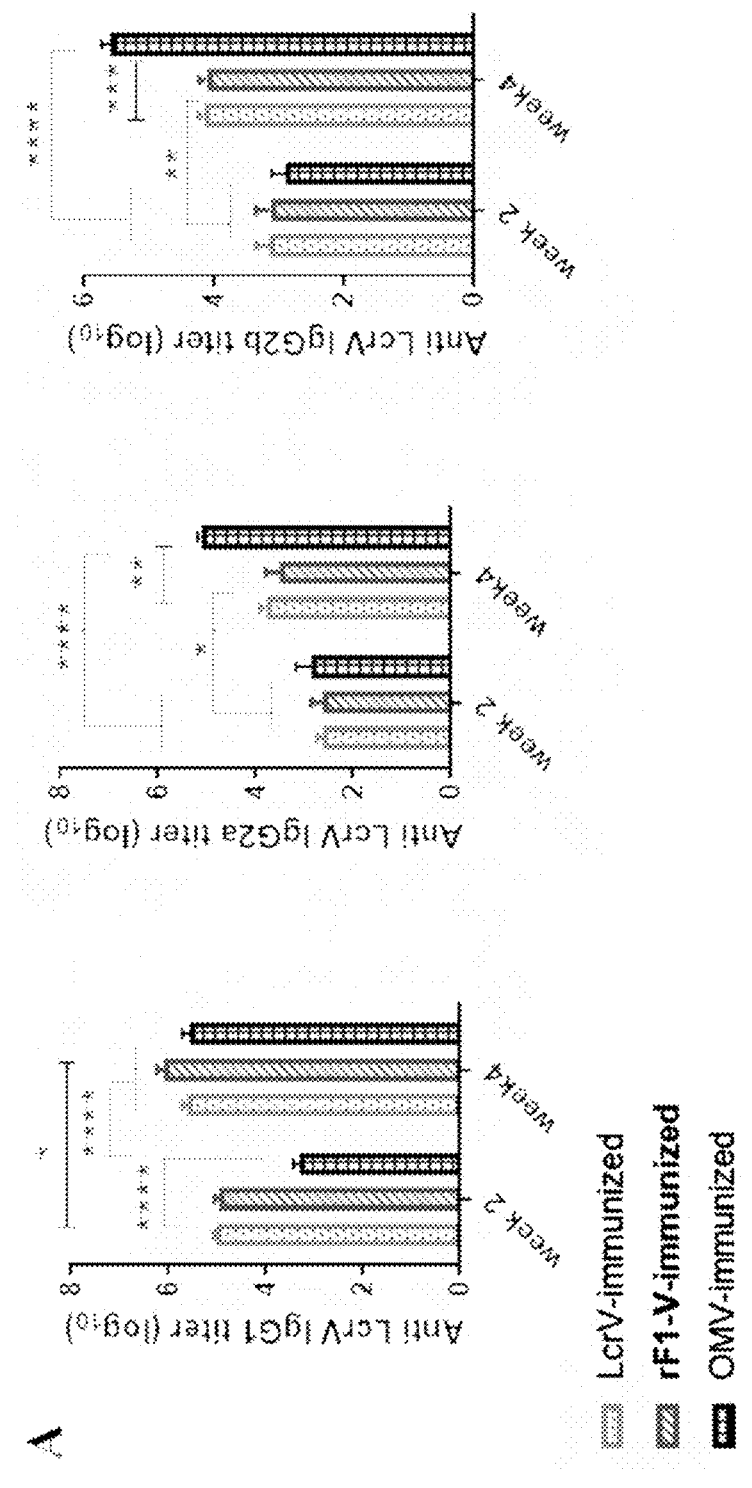
Figure 5B:
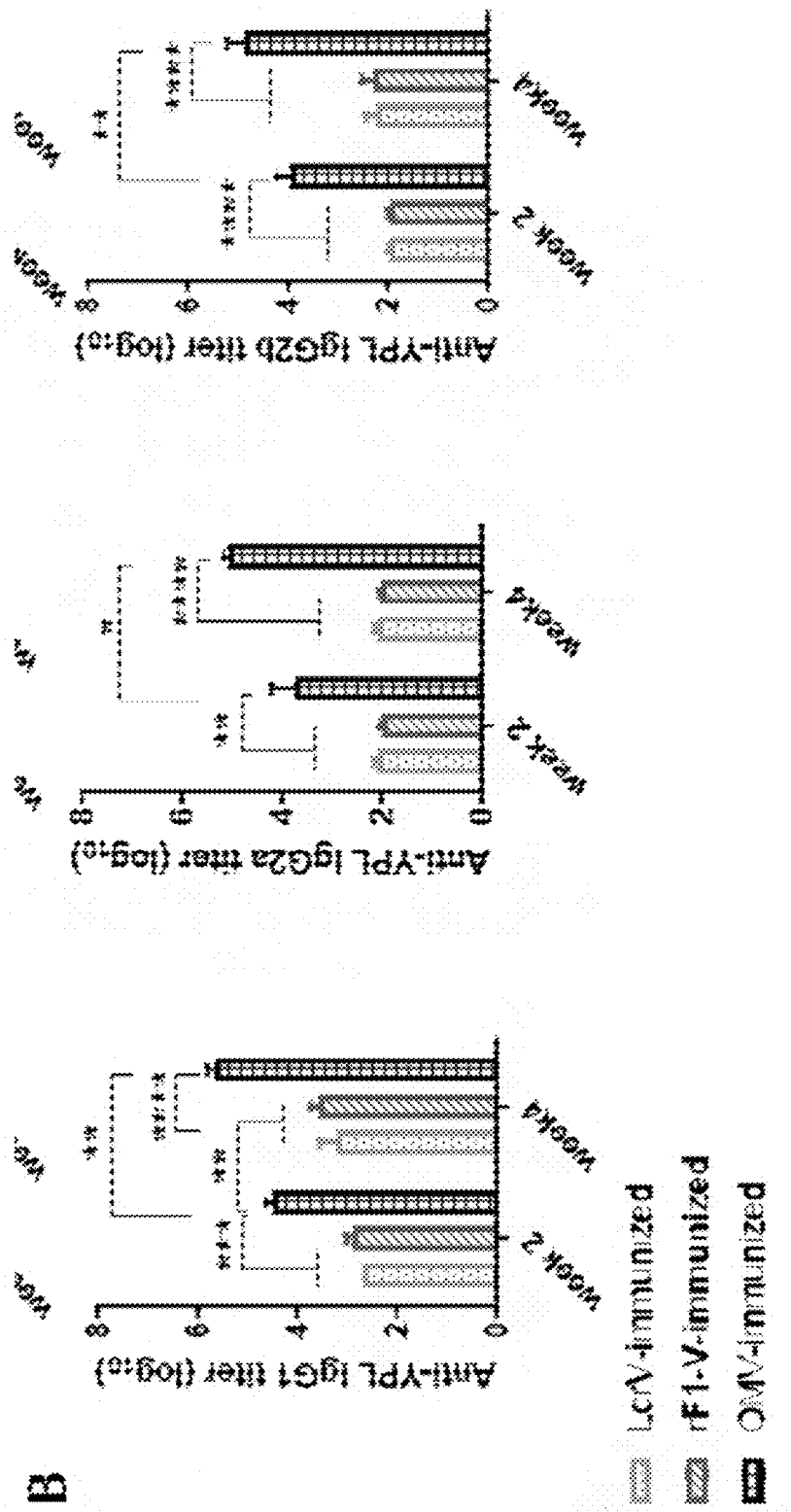
Figure 5C:
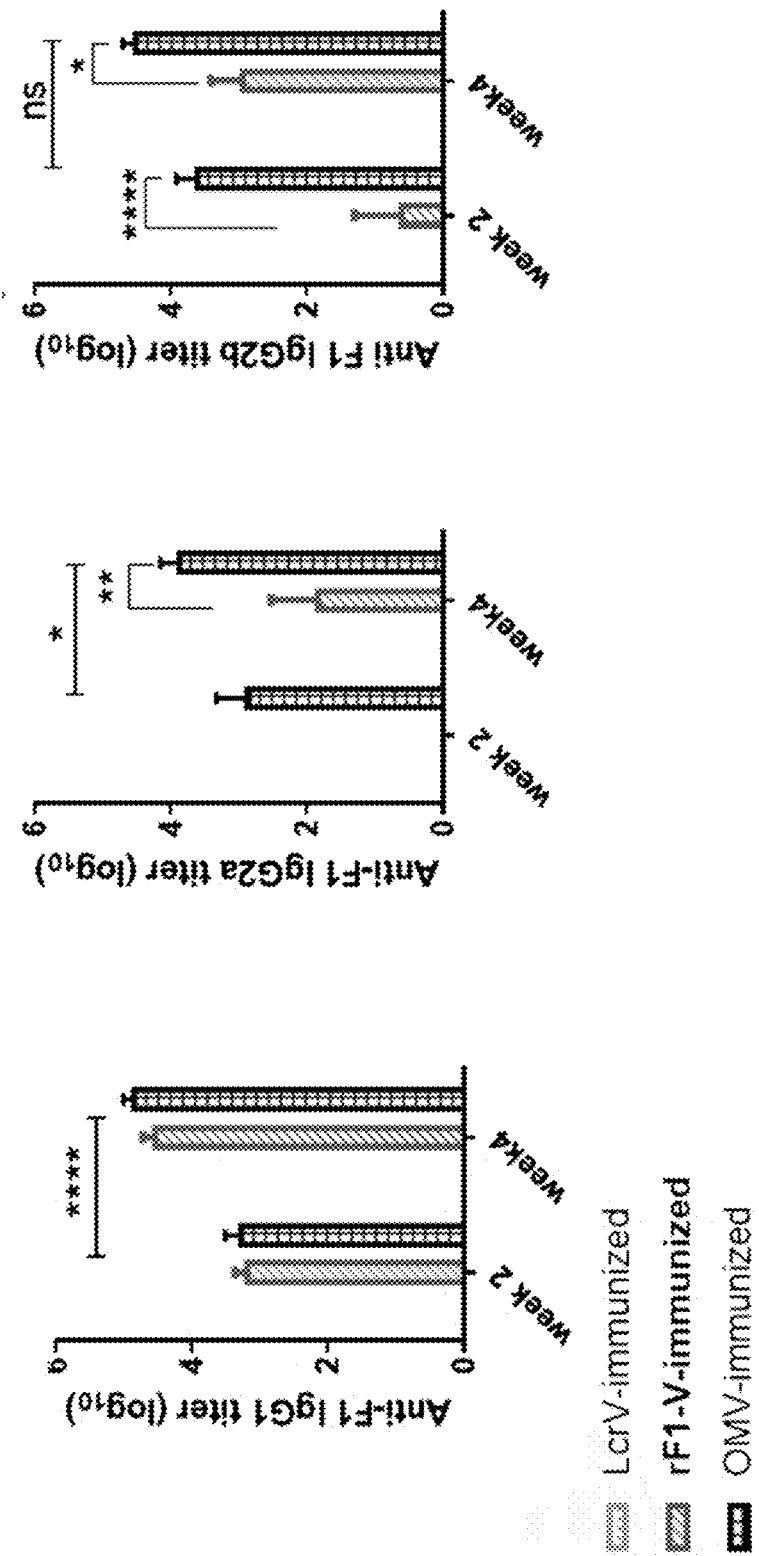

FIGS. 5A through 5C are a graphical analysis of antibody isotypes in immunized mice sera collected at days 14 and 28 after prime and booster immunization. FIG. 5A—Anti-LcrV IgG1, IgG2a and IgG2b. FIG. 5B—Anti-YPL IgG1, IgG2a and IgG2b. FIG. 5C—Anti-F1 IgG1, IgG2a and IgG2b. The statistical significance among the groups at day 14 and day 28 were analyzed by two-way multivariant ANOVA with a Tukey post hoc test: *, P<0.05; , P<0.01; *, P<0.001, ****, P<0.0001.

Figure 6A:
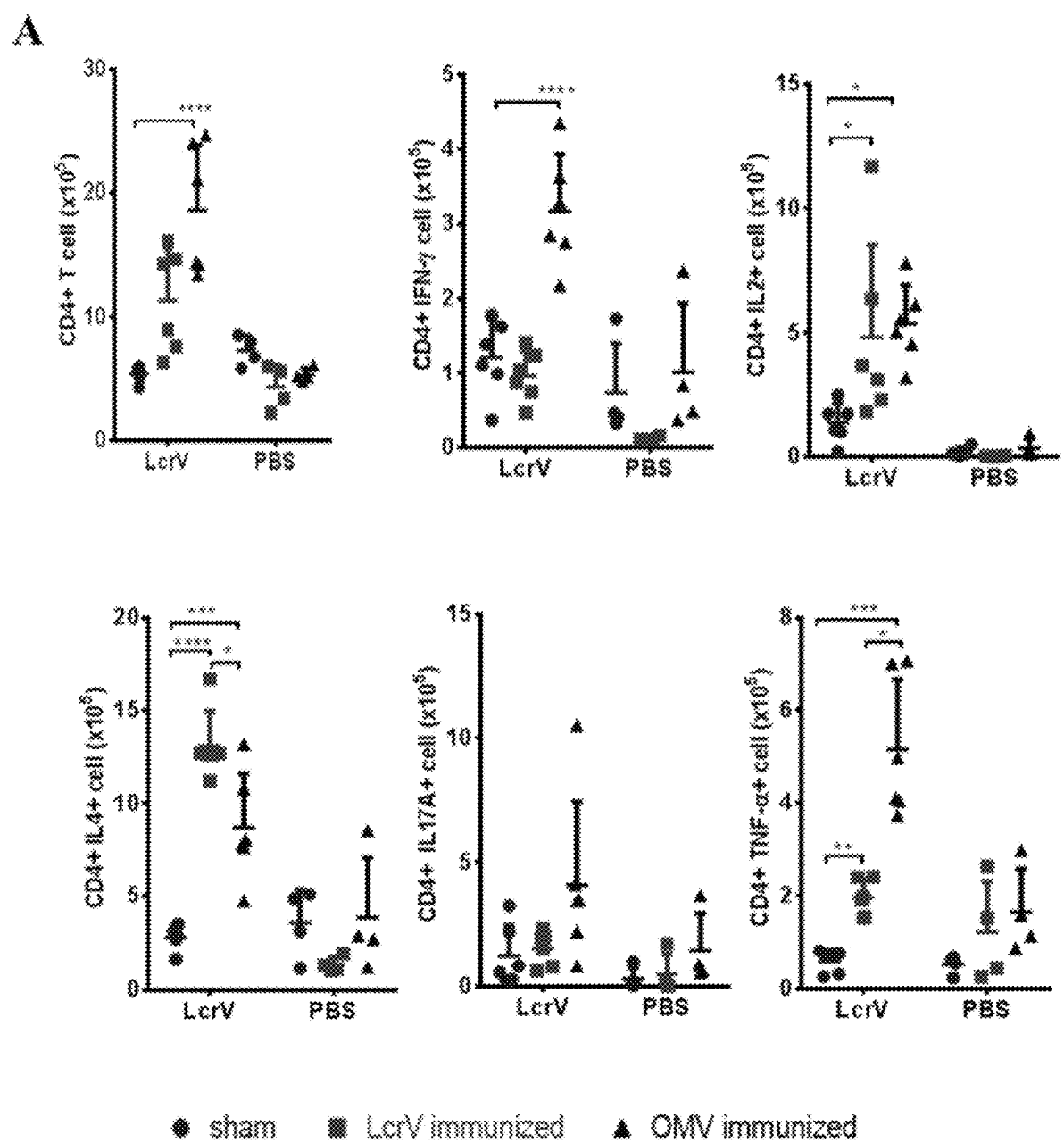
Figure 6B:
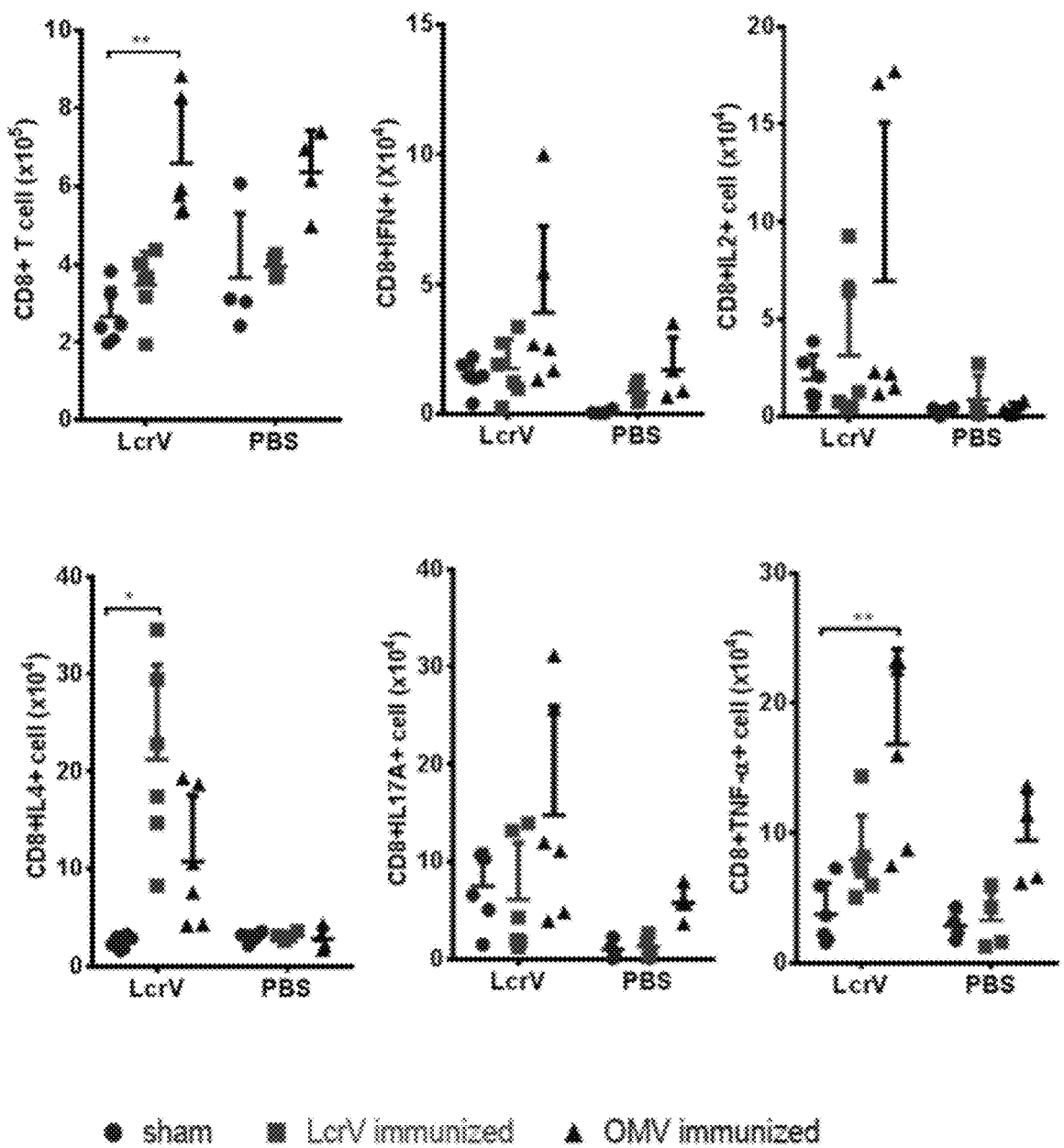

FIGS. 6A and 6B are a graphical analysis of antigen-specific T cells obtained from lungs and associated cytokine responses. On day 42 after the initial immunization, lymphocytes were aseptically isolated from mice and stimulated in vitro with 20 µg/ml purified recombinant LcrV protein for 72 h to detect specific CD4+ and CD8+ T cells encoding IFN-γ, IL-2, IL-4, IL-17 and TNF-α. Sham mice lung cells were considered as controls. FIG. 6A—CD4+ T-cell numbers in lungs and CD4+ IFN-γ+-, CD4+ IL-2+-, CD4+ IL-4+-, CD4+ IL-17+-, and CD4+ TNF-α+-positive cell numbers. FIG. 6B—CD8+ T-cell numbers in lungs and CD8+ IFN-γ+-, CD8+ IL-2+-, CD8+ IL-4+-, CD8+ IL-17+-, and CD8+ TNF-α+-positive cell numbers. Each symbol represents a data point obtained from an individual mouse, with horizontal mean value bars±SD. Statistical significance: *, P<0.05; , P<0.01; *, P<0.001; ****, P<0.0001.

Figures 7A, 7B:
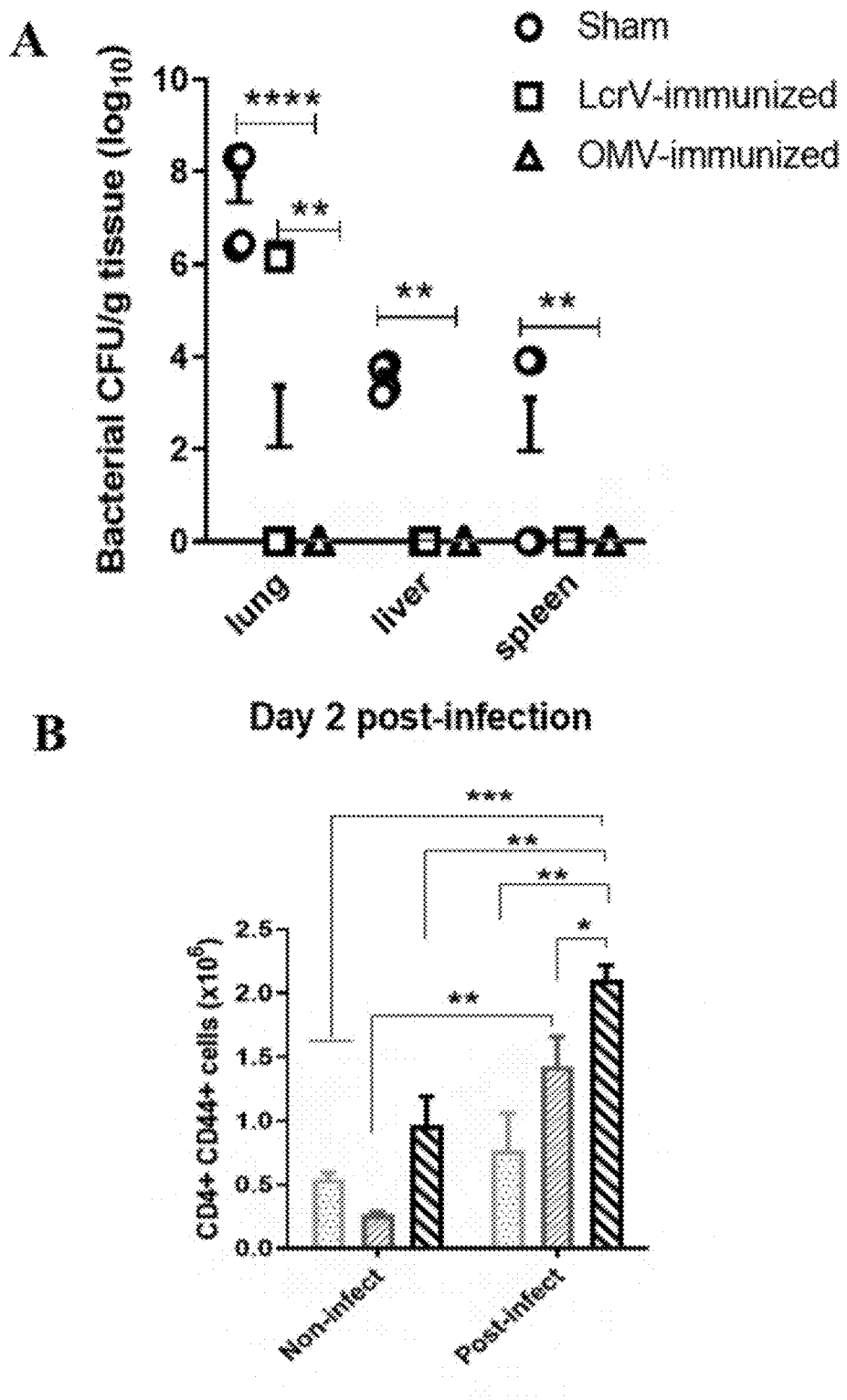
Figures 7D, 7E, 7F:
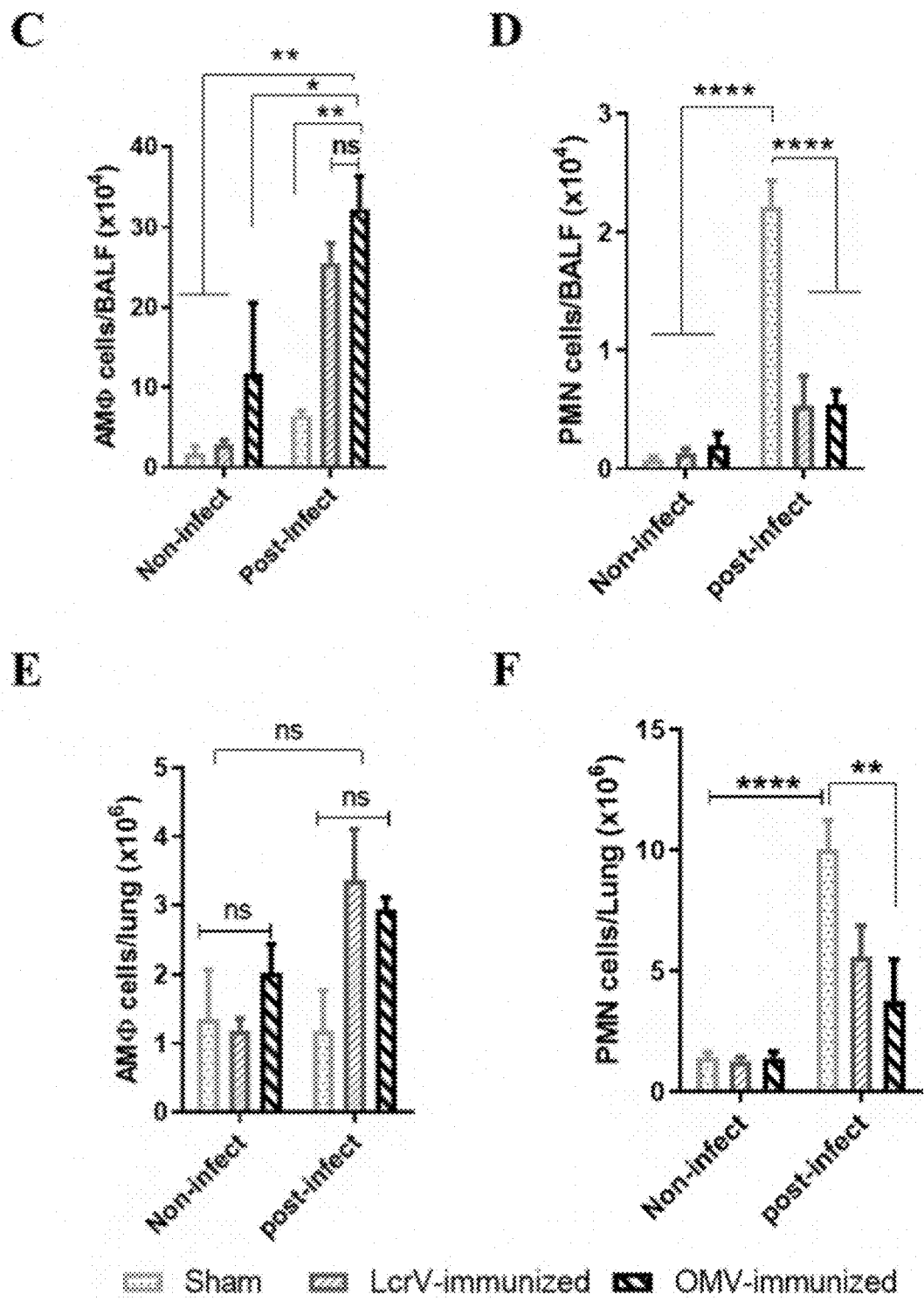

FIGS. 7A through 7F are a graphical analysis of in vivo responses after *Y. pestis* pulmonary challenge. Sham-, LcrV- or OMV-immunized Swiss-Webster mice (3 mice per group) were infected i.n. with $3 \times 10^3$ CFU of *Y. pestis* KIM6+ (pCD1Ap). The groups of immunized mice infected with PBS served as negative controls. On day 2 post challenge, different tissues (lungs, livers and spleens) and bronchoalveolar lavage fluid (BALF) were collected from the euthanized mice. FIG. 7A—Bacterial burden was evaluated in the lungs, livers and spleens. FIG. 7B—CD4+CD44+ cell numbers in the lungs of mice with or without infection were analyzed. FIG. 7C—Alveolar macrophages in the BALF of mice with or without infection. FIG. 7D—Neutrophils in the BALF of mice with or without infection. FIG. 7E—Alveolar macrophages in the lungs of mice with or without infection. FIG. 7F—Neutrophils in the lungs of mice with or without infection. Statistical significance: ns, no significance; *, P<0.05; , P<0.01; *, P<0.001, ****, P<0.0001.

Figure 8A:
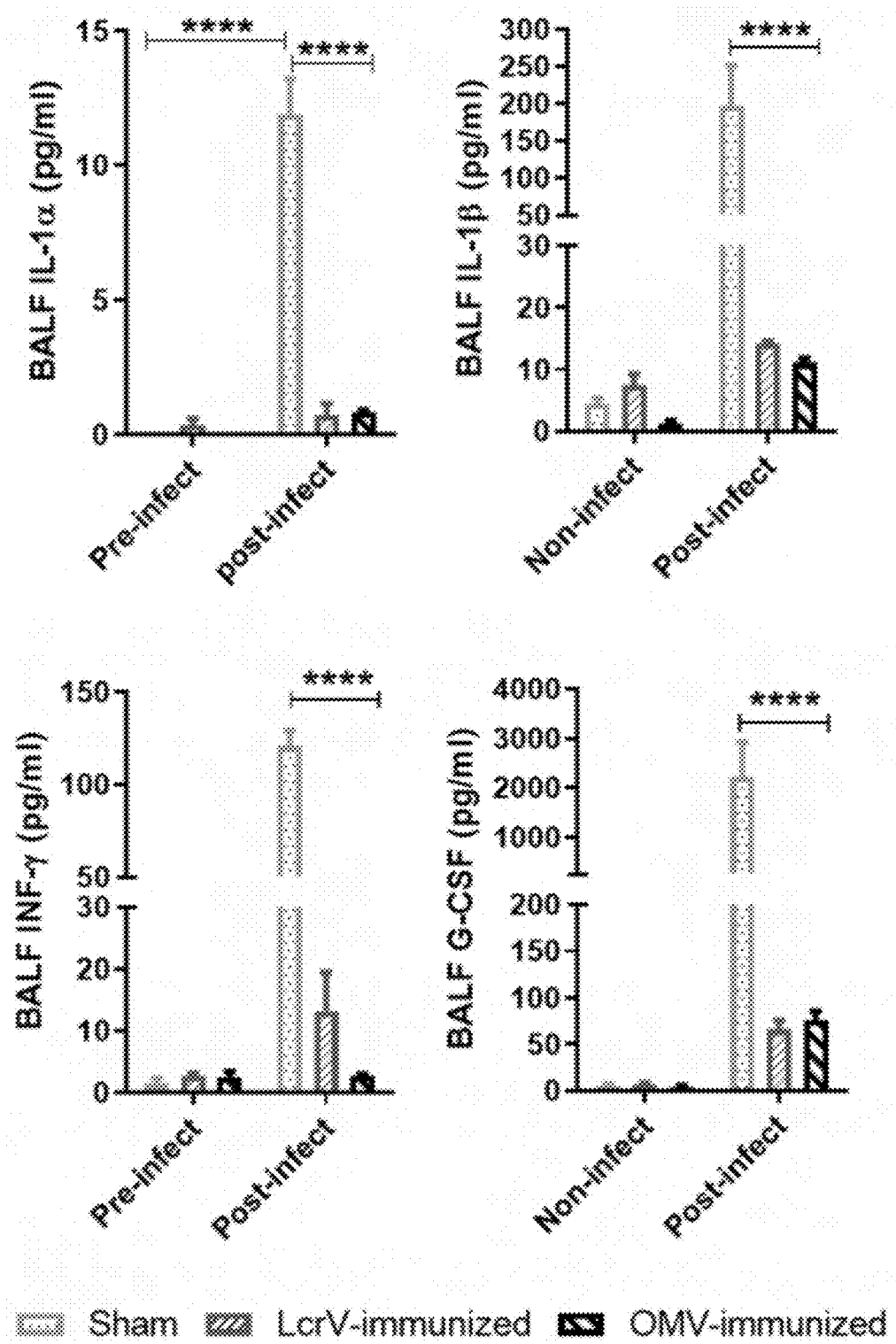
Figure 8B:
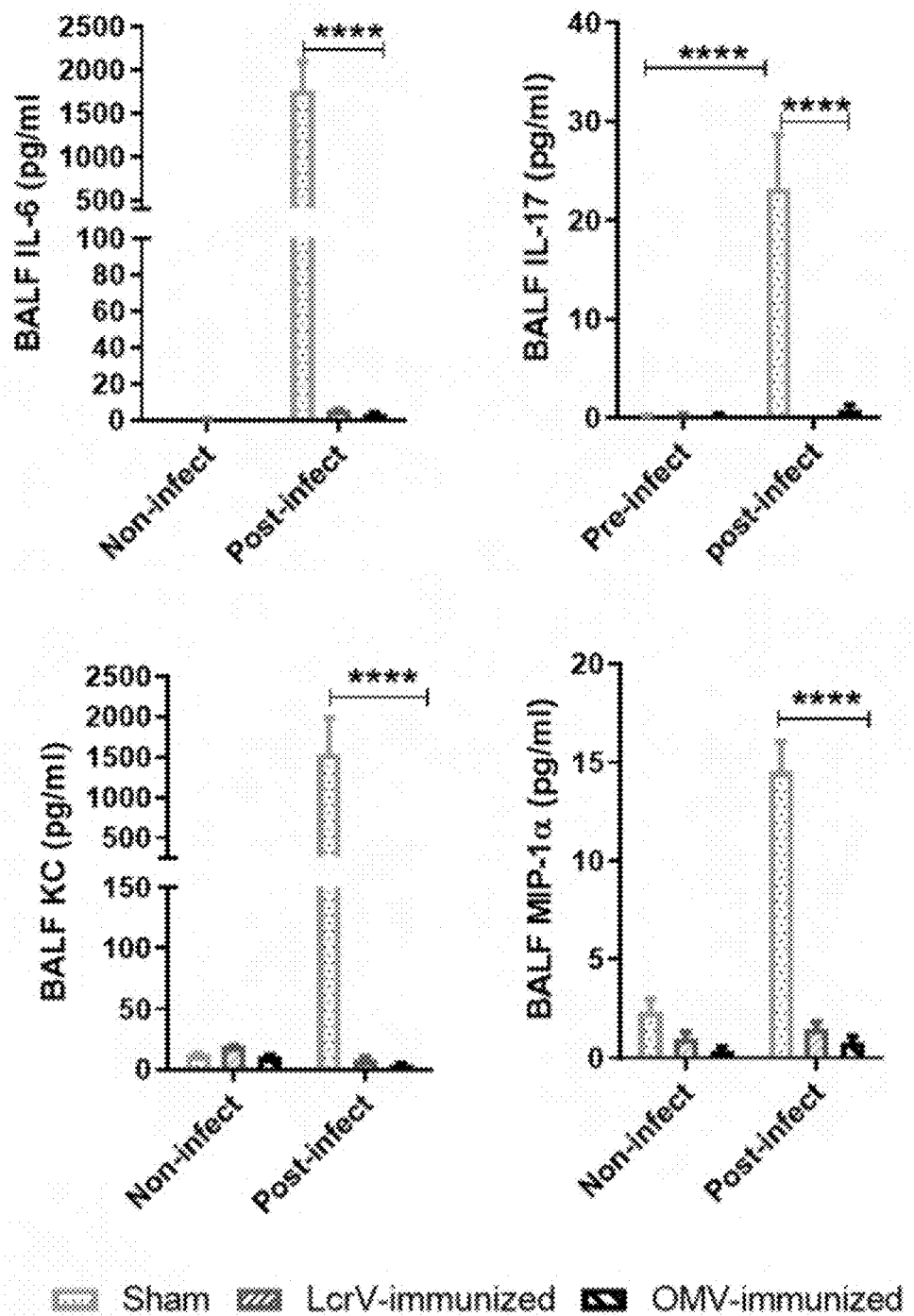

FIG. 8A and FIG. 8B are comparisons of cytokine and chemokine levels in the BALF from mice with and without pulmonary *Y. pestis* challenge. Sham-, LcrV- or OMV-immunized Swiss-Webster mice (3 mice per group) were infected i.n. with $3 \times 10^3$ CFU of *Y. pestis* KIM6+(pCD1Ap). The groups of immunized mice infected with PBS served as negative controls. On day 2 post challenge, BALF from each euthanized mouse was collected at 48 h post infection, filtered through a 0.22-µm syringe filter and checked for sterility before transfer to the BSL2 lab for analysis. A Bio-Plex Pro™ Mouse Cytokine Assay kit (Bio-Plex) was used to detect the cytokines and chemokines, such as IL-1α, IL-1β, IL-6, IL-17, IFN-γ, G-CSF, KC and MIP-1α, in the BALF collected from mice according to the manufacturer's instructions. The statistical significance among the groups was analyzed by two-way multivariant ANOVA with a Tukey post hoc test. ****, P<0.0001. Abbreviations: interferon (IFN) γ; granulocyte CSF (G-CSF); Keratinocyte chemoattractant (KC); macrophage inflammatory protein 1-alpha (MIP-1-α).

Figure 9A:
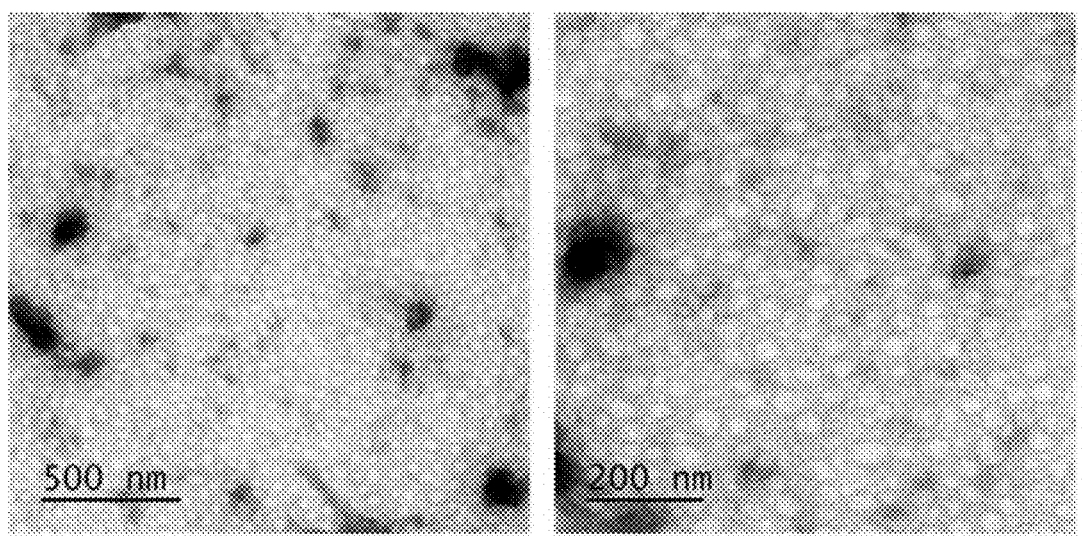
Figure 9B:
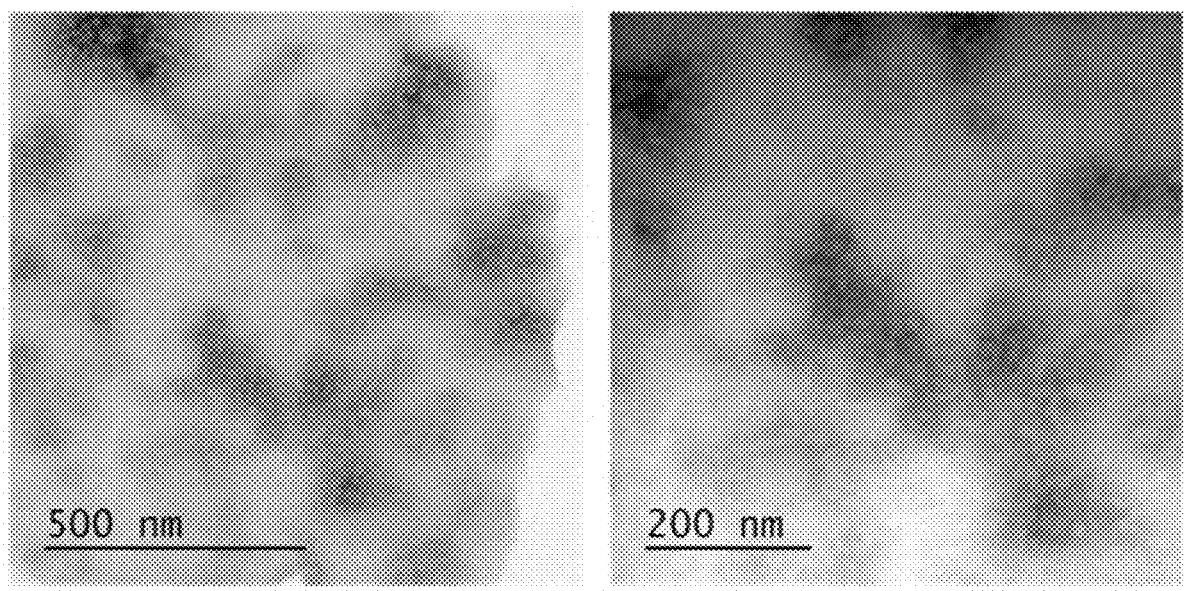

FIGS. 9A and 9B are visualizations of Outer membrane vesicles (OMVs) via transmission electron microscopy (TEM). FIG. 9A—TEM of OMVs purified from χ10015 (ΔlpxP:: $P_{lpxL}$lpxL) culture supernatants. FIG. 9B—TEM of OMVs purified from χ10027 (ΔlpxP:: $P_{lpxL}$lpxL ΔlacZ $P_{lp-p}$lpxE) culture supernatants. Bars, 500 nm and 200 nm.

Figure 10A:
Figure 10B:
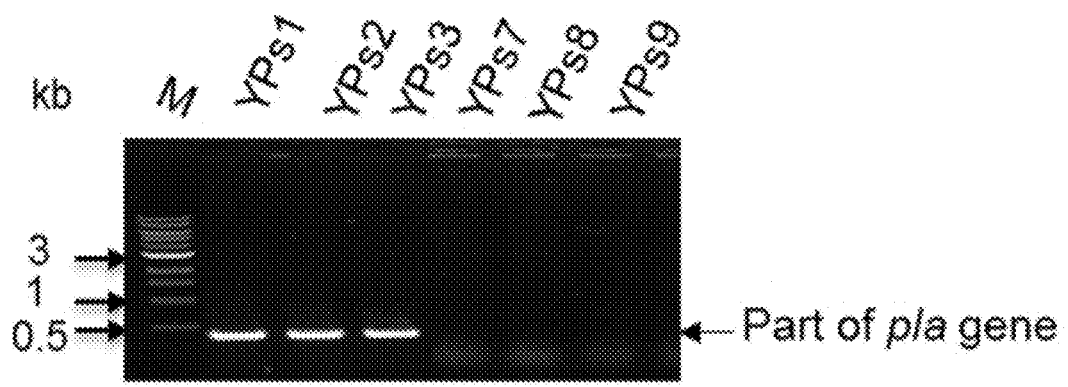
Figure 10B:
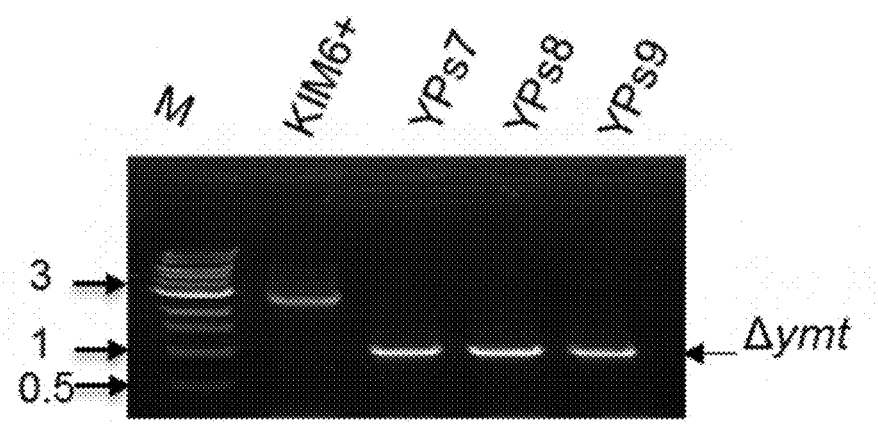
Figure 10B:
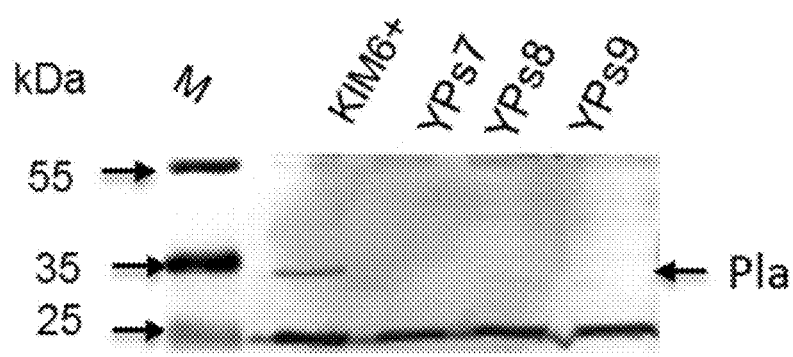

FIGS. 10A through 10B are illustrations of the elimination of potential virulence factors from *Y. pestis* constructions, where FIG. 10A shows elimination of the pPCP1 plasmid and deletion of the ymt gene from *Y. pestis* constructions and FIG. 10B shows removal of the pPCP1 plasmid and deletion of the ymt gene were verified by PCR, and presence and absence of Pla encoded in the pPCP1 plasmid were verified by western blotting.

Figure 11A:
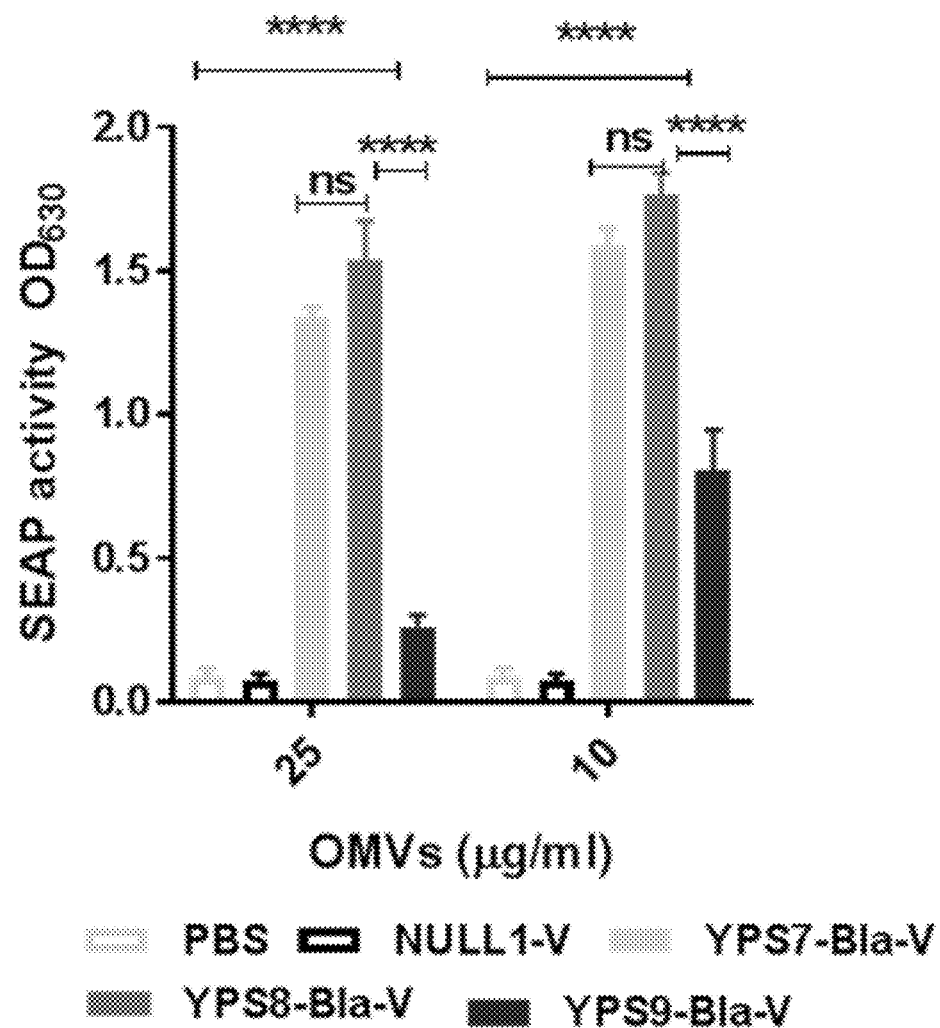
Figure 11B:
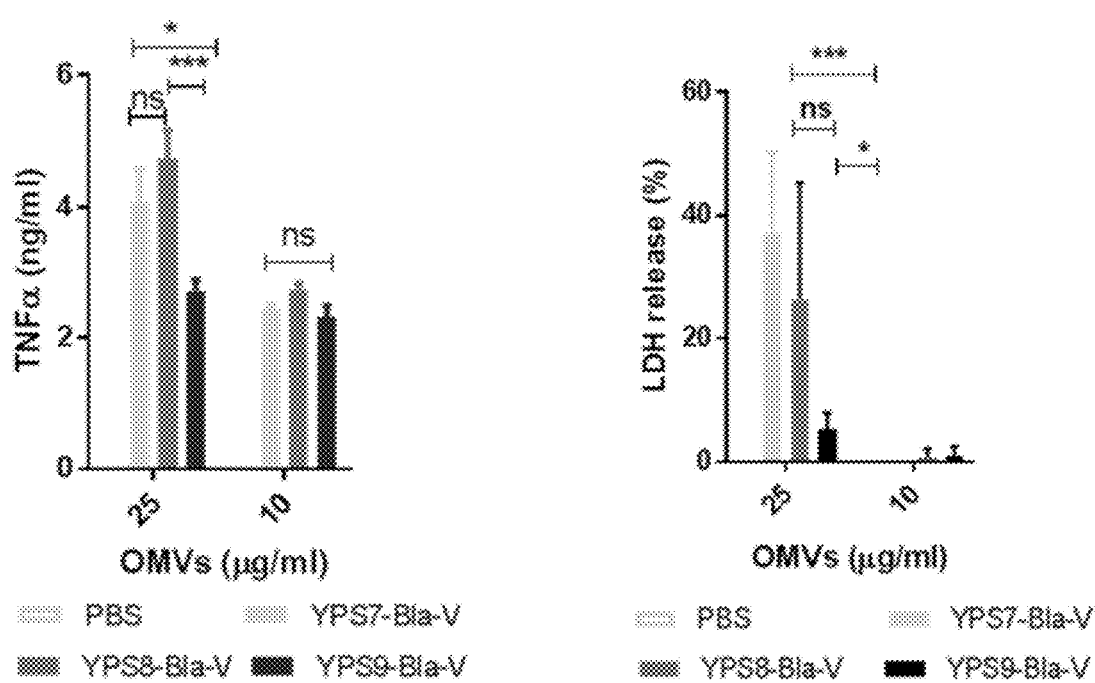

FIGS. 11A and 11B are a graphical analysis of the stimulation and cytotoxicity of OMVs in vitro. FIG. 11A is a comparison of the secreted embryonic alkaline phosphatase (SEAP) activities in HEK-Blue™ cells with or without murine toll-like receptor 4. HEK-Blue™ mTLR4 (InvivoGen) cells were co-cultured with 25 or 10 µg/ml OMVs from *Y. pestis* YPS7(Bla-V), YPS8(Bla-V) and YPS9 (Bla-V) strains for 8 hours, respectively. HEK-Blue™ Null1-v cells or PBS were used as negative controls and 20 ng/ml of LPS from *Salmonella* was used as positive control. FIG. 11B is a comparison of the secreted TNF-α and percentage of LDH release from murine macrophage RAW 264.7 cells treated with 25 or 10 µg/ml OMVs from *Y. pestis* YPS7(Bla-V), YPS8(Bla-V) and YPS9(Bla-V) strains for 24 hours, respectively.

Figure 12A:
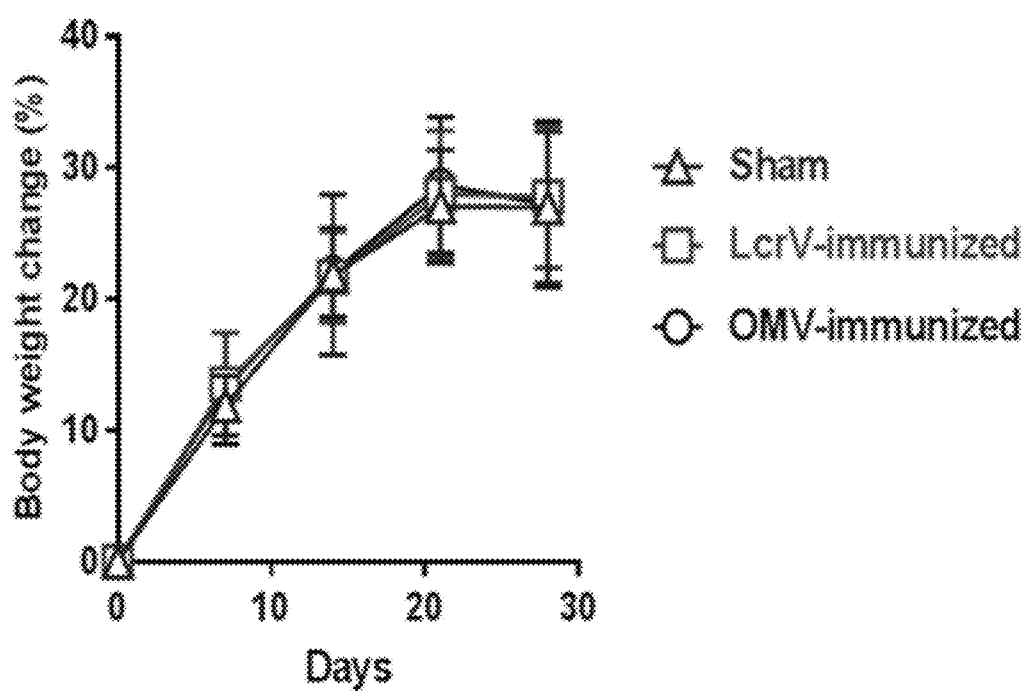
Figure 12B:
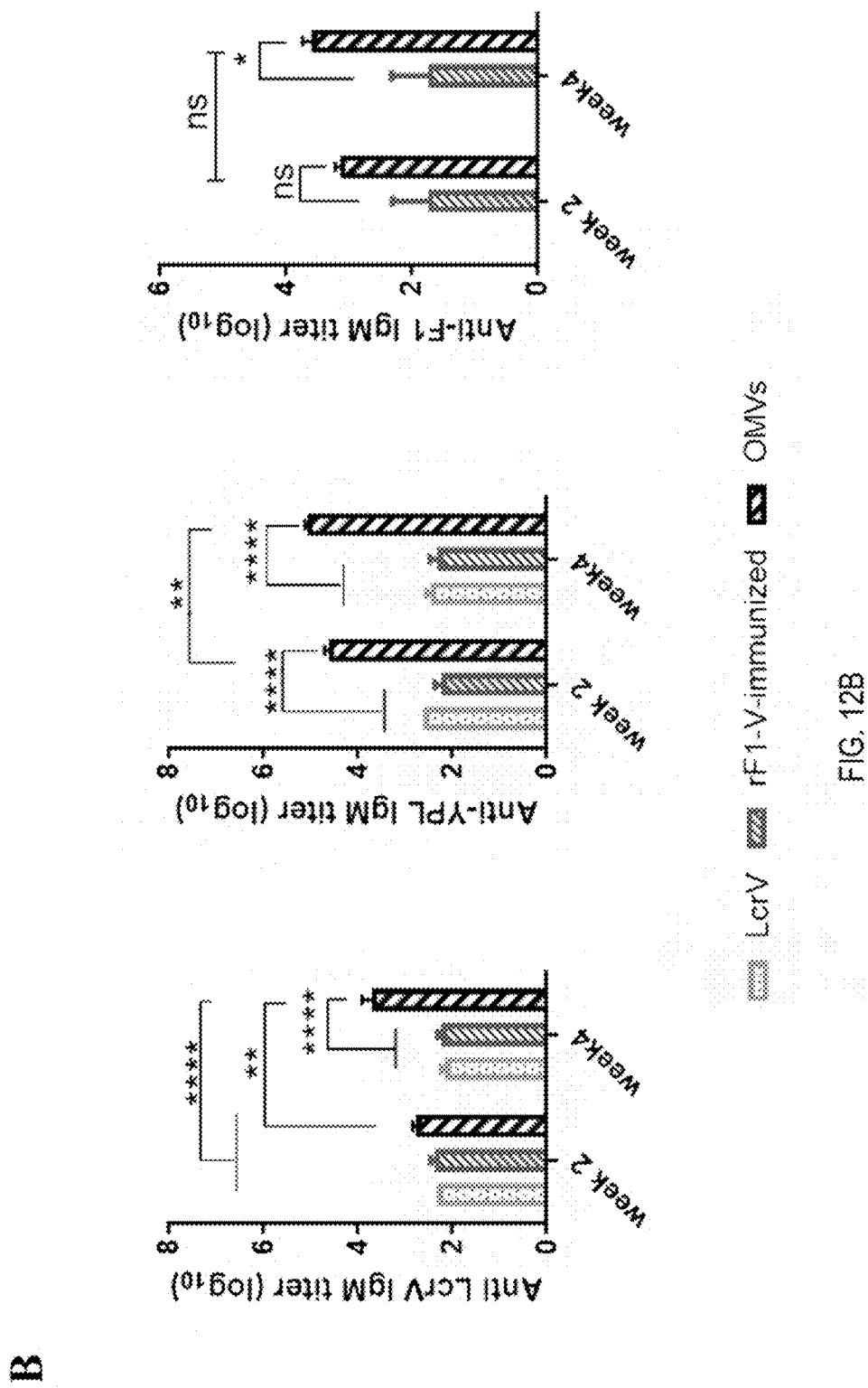

FIGS. 12A and 12B are a graphical analysis of mouse body-weight changes after immunization and the IgM titers in LcrV- or OMV-immunized mice. FIG. 12A—The increase rates of mouse body weight after immunization with OMVs, LcrV/alhydrogel or PBS/alhydrogel (sham). FIG. 12B—LcrV, YPL (*Y. pestis* whole cell lysate) and F1-specific IgM titers in mice at day 14 and 28 post immunization. Data represented mean value±standard deviation (SD). *, P<0.05; , P<0.01; *, P<0.001.

Figure 13A:
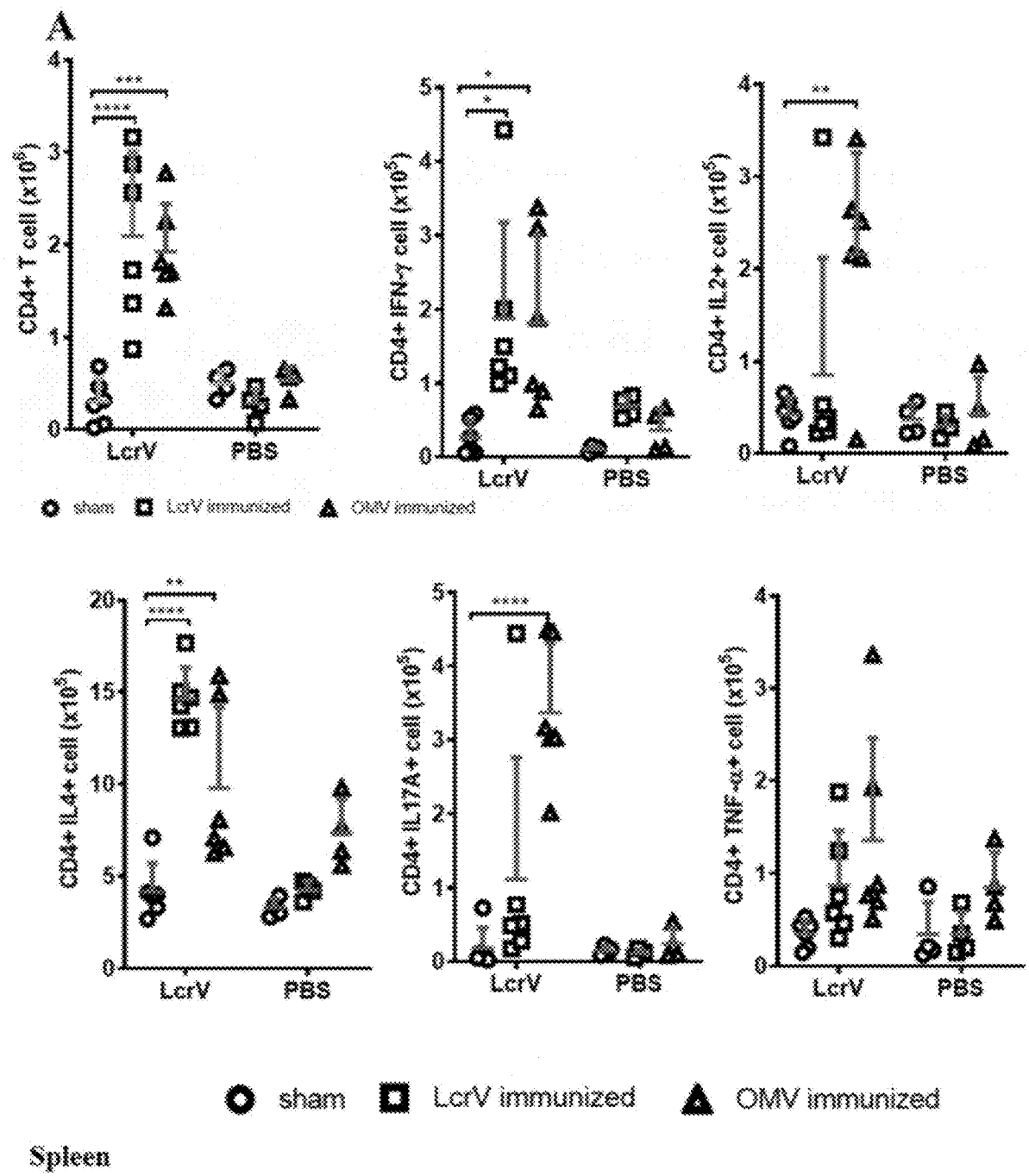
Figure 13B:
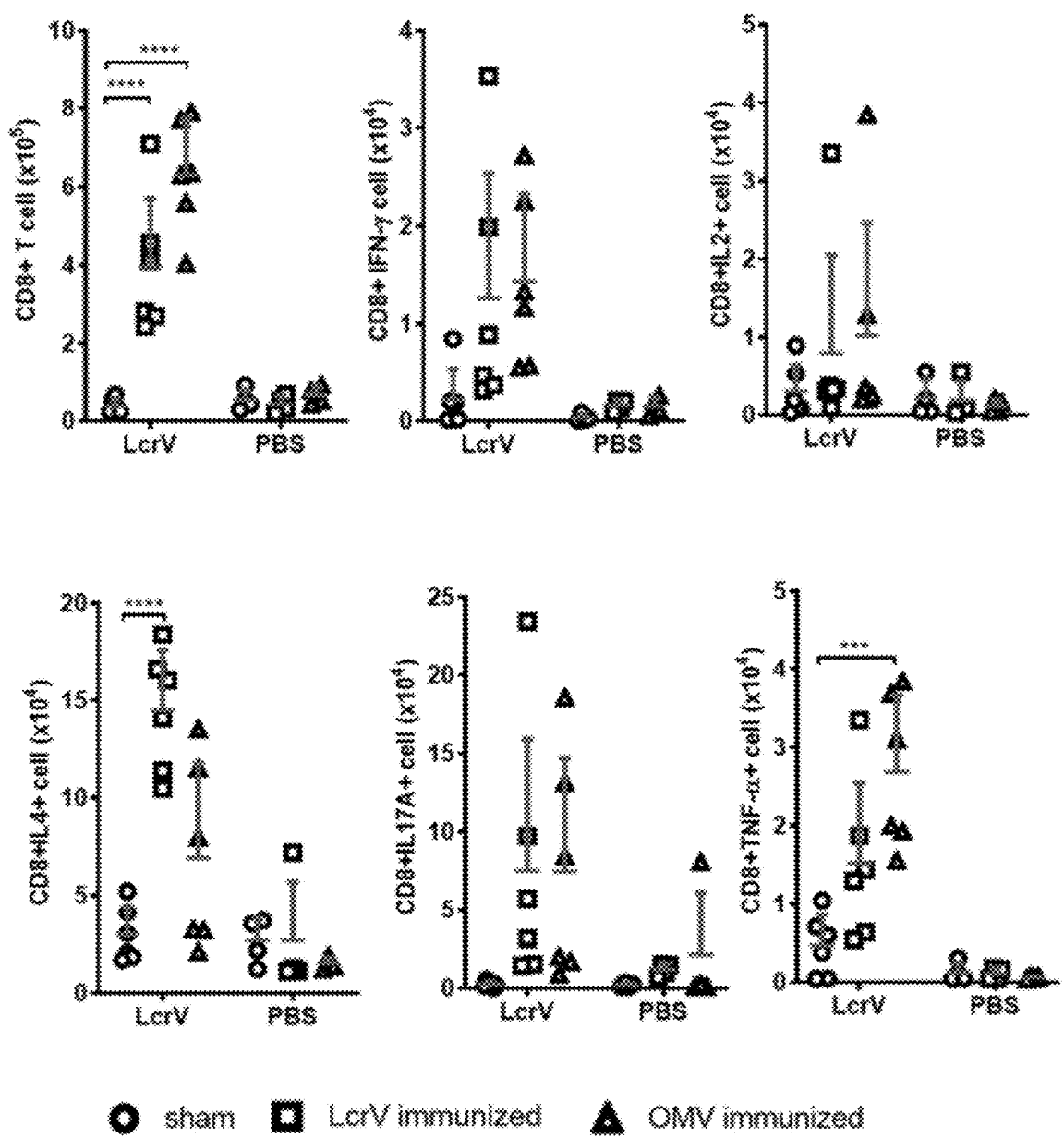

FIGS. 13A and 13B are an analysis of antigen-specific T cells from spleens and associated cytokine responses. On the day 42 after initial immunization, splenocytes were aseptically isolated from mice and stimulated in vitro with 20 µg/ml purified LcrV protein for 72 h to assess specific CD4+ and CD8+ T cells encoding IFN-γ, IL-2, IL-4, IL-17 and TNF-α. The sham mice spleen cells were considered as negative controls. FIG. 13A—CD4+ T-cell numbers, CD4+ IFN-γ+-, CD4+ IL-2+-, CD4+ IL-4+-, CD4+ IL-17+-, and CD4+ TNF-α+-positive cell numbers in spleens. FIG. 13B—CD8+ T-cell numbers, CD8+ IFN-γ+-, CD8+ IL-2+-, CD8+ IL-4+-, CD8+ IL-17+-, and CD8+ TNF-α+-positive cell numbers in spleens. Each symbol represents data obtained from individual mice, with horizontal mean value bars±SD. The statistical significance among the groups was analyzed by two-way multivariant ANOVA with a Tukey post hoc test. *, P<0.05; , P<0.01; *, P<0.001; ****, P<0.0001. Abbreviations: interferon (IFN) γ; tumor necrosis factor (TNF) α.

Figure 14A:
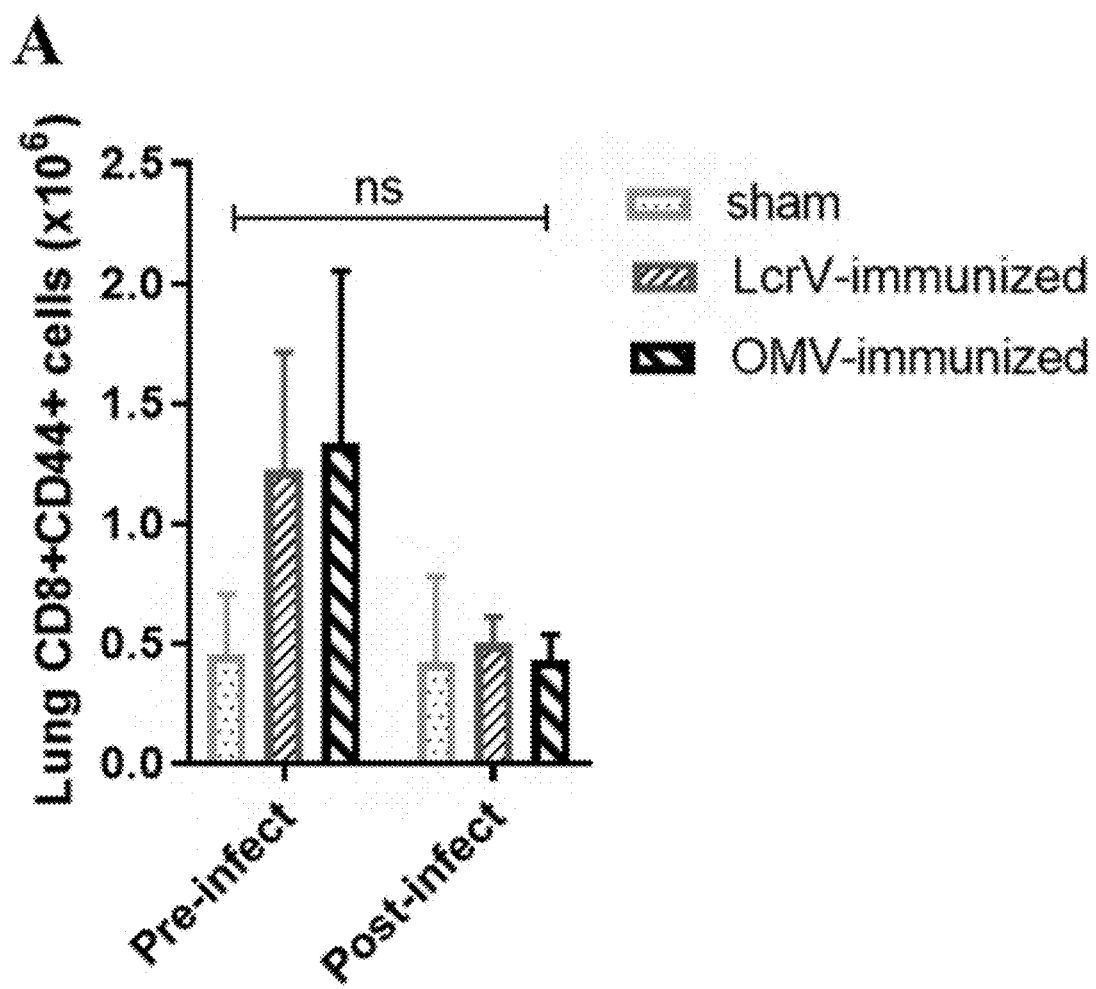
Figure 14B:
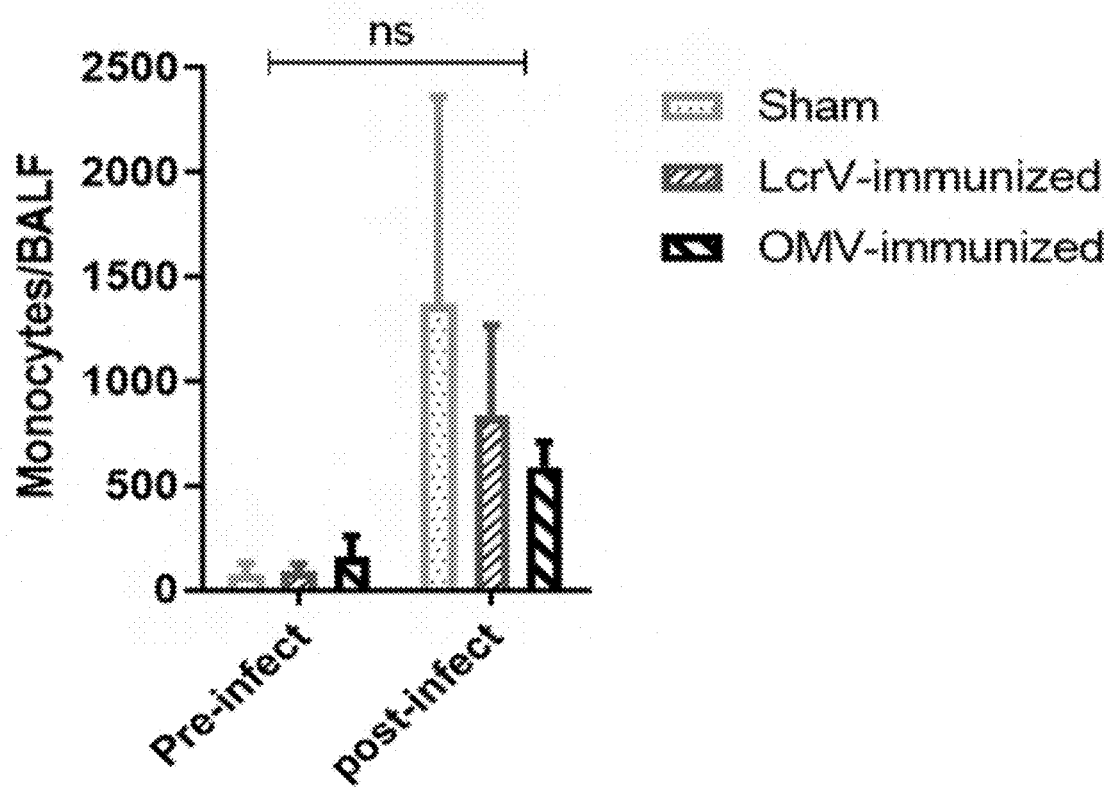
Figure 14C:
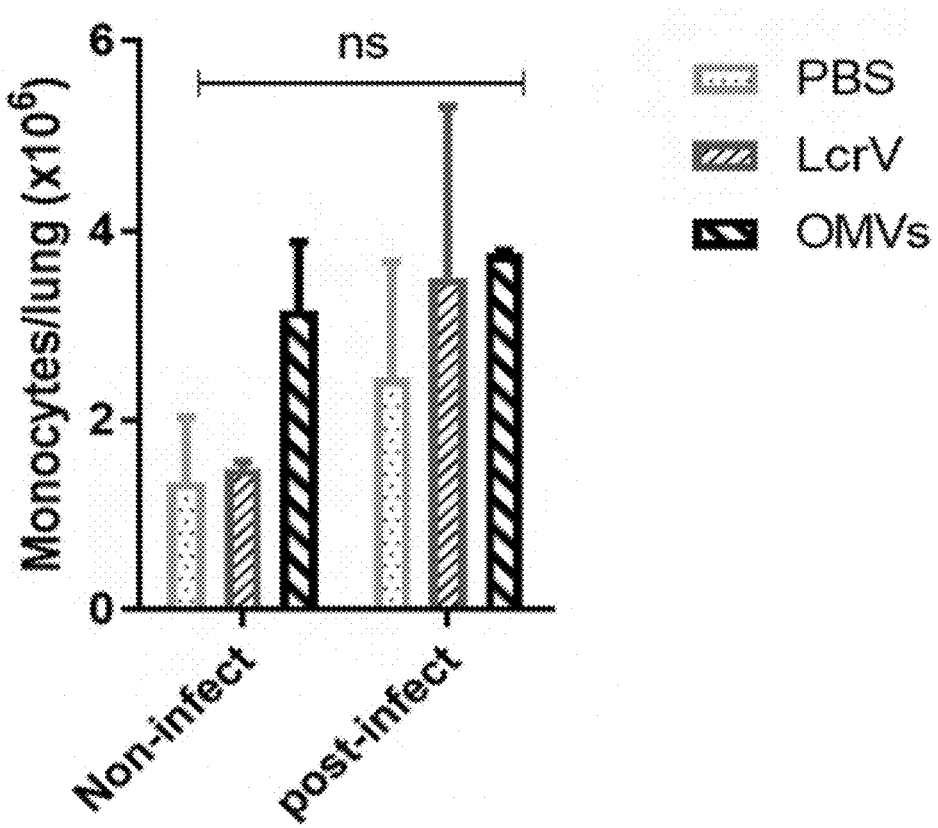

FIG. 14A through FIG. 14C are an analysis of the variations of CD8+CD44+ and monocytes in lungs of mice after Y. pestis pulmonary challenge. FIG. 14A—CD8+CD44+ cell numbers in the lungs of mice with or without infection were analyzed. FIG. 14B—Monocytes in the BALFs of mice with or without infection. FIG. 14C Monocytes in the lungs of mice with or without infection. The statistical significance among the groups was analyzed by two-way multivariant ANOVA with a Tukey post hoc test. ns, no significance.

Figure 15A:
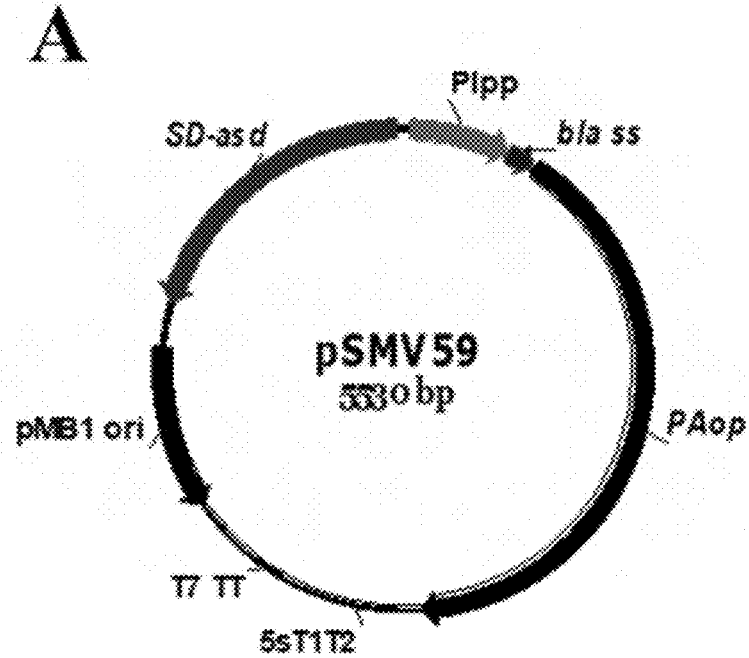
Figure 15A:
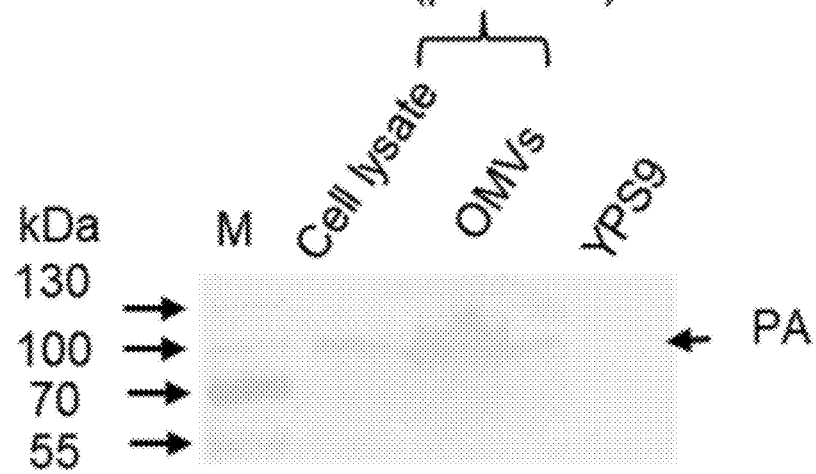
Figure 15B:
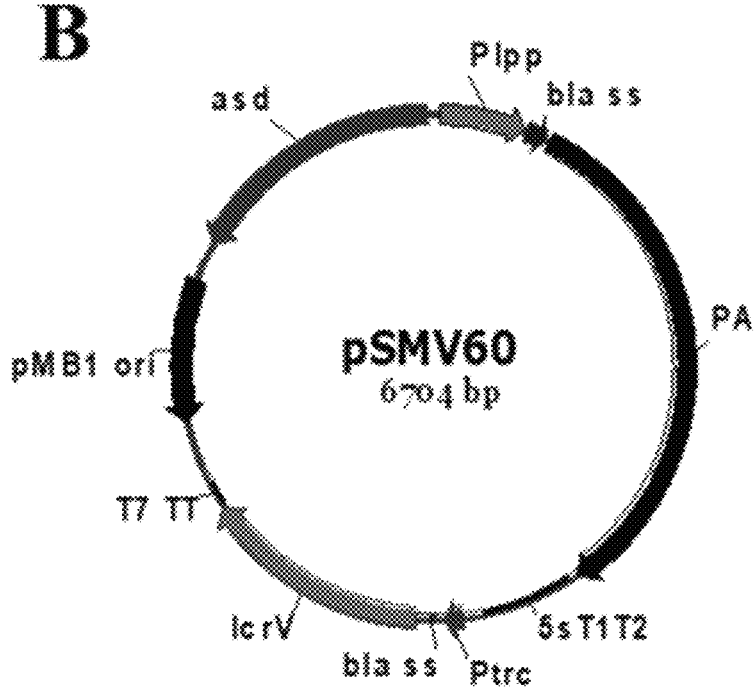
Figure 15B:
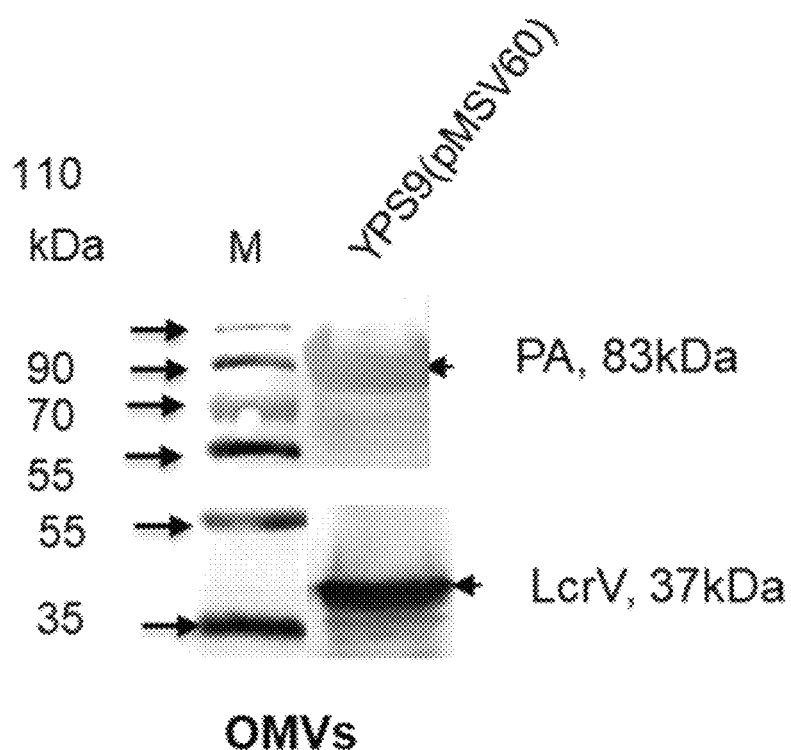

FIGS. 15A and 15B are an analysis of over-synthesizing PA antigen of B. anthracis in Y. pestis mutants. FIG. 15A—Physical maps of Asd+ plasmids pSMV59 harboring the N-terminal β-lactamase signal sequence (bla ss) and codon-optimized pagA fusion to facilitate PA secretion by Type II secretion system. PA synthesis was detected by immunoblotting with PA-specific polyclonal rabbit antibody in whole cell lysate and OMVs of YPS9(pSMV59). FIG. 15B—Physical maps of Asd+ plasmids pSMV60 harboring both the N-terminal β-lactamase signal sequence (bla ss) and codon-optimized pagA fusion and the N-terminal β-lactamase signal sequence (bla ss) and lcrV fusion. LcrV and PA were synthesized in OMVs from YPS9(pSMV60)

Figure 16A:
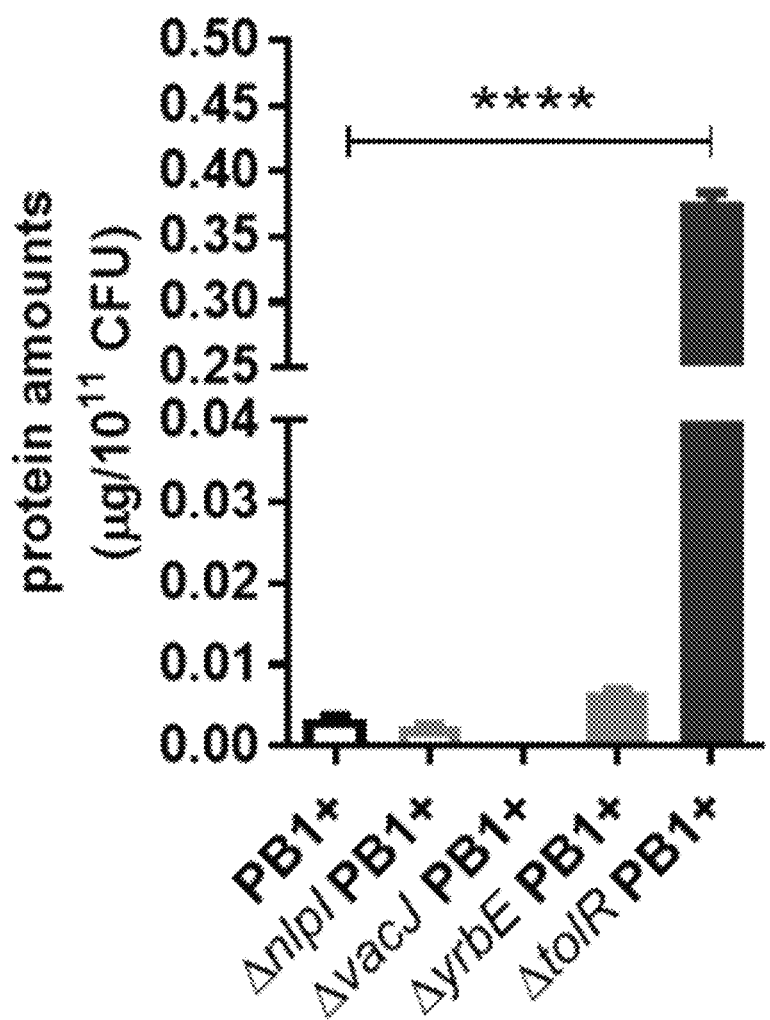
Figure 16B:
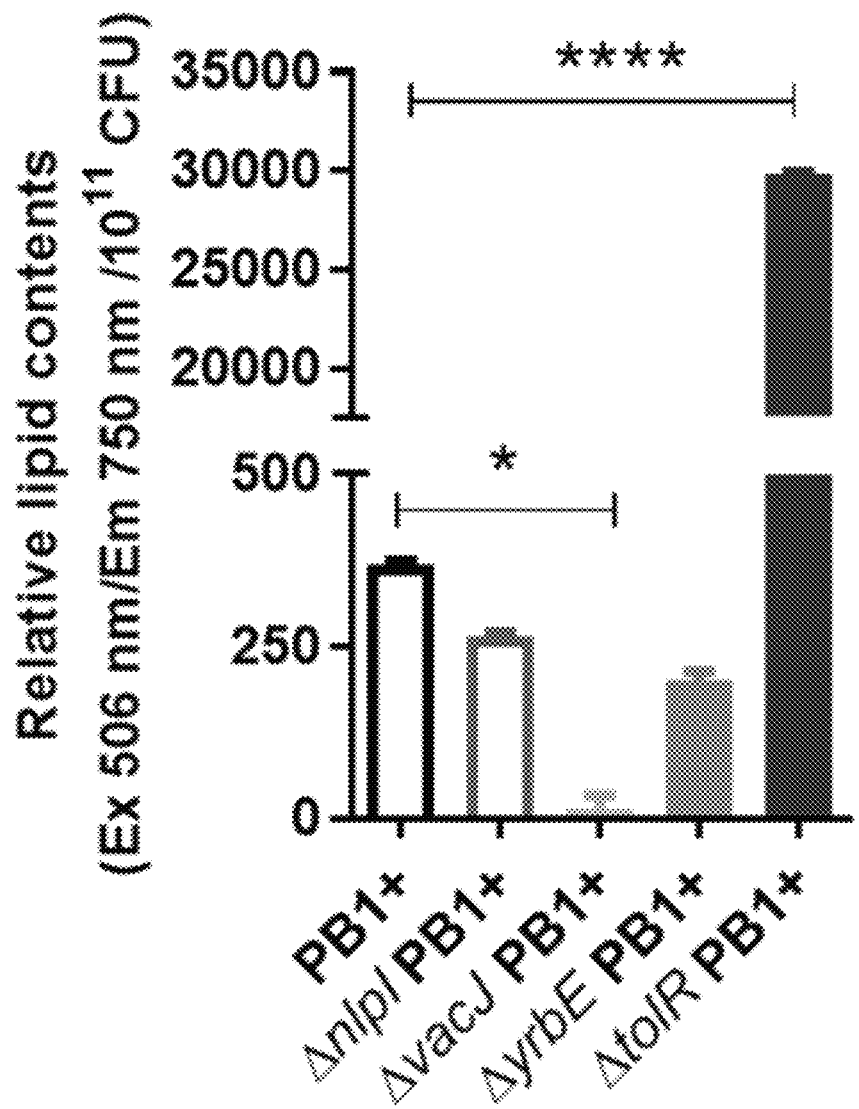

FIG. 16A and FIG. 16B are a series of graphs of the production of OMVs in different Yptb PB1+ strains where FIG. 16A shows protein amounts in OMVs (Bradford protein assay) and FIG. 16B shows the relative value of lipid contents (Fluorescent lipophilic dye FM4-64).

Figure 17A:
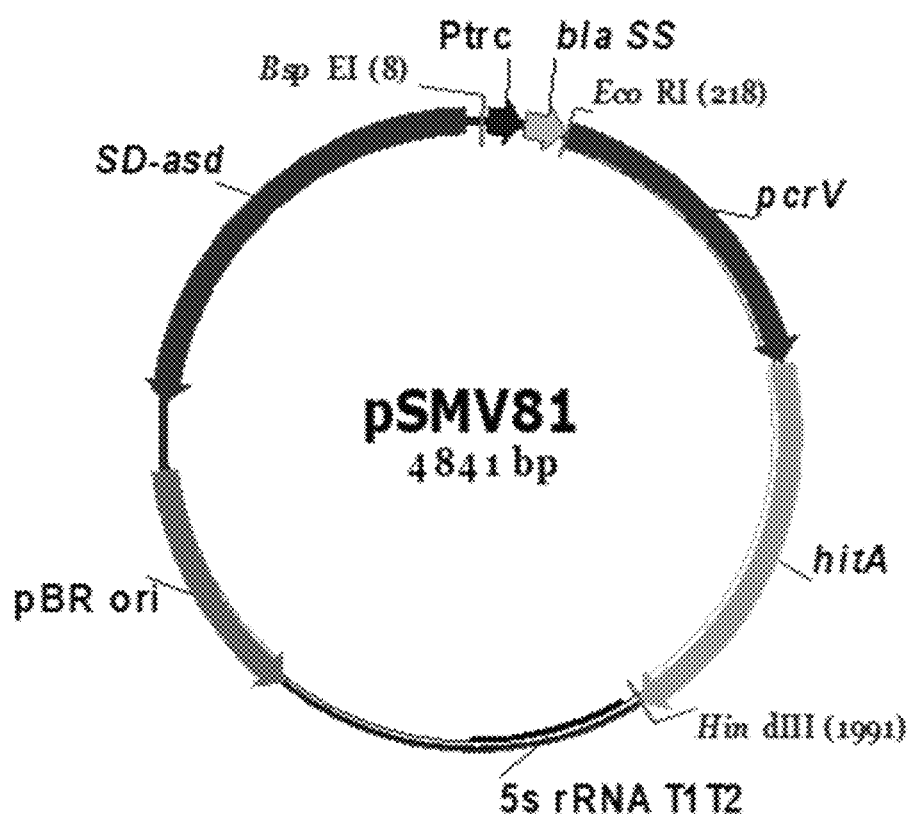
Figure 17B:
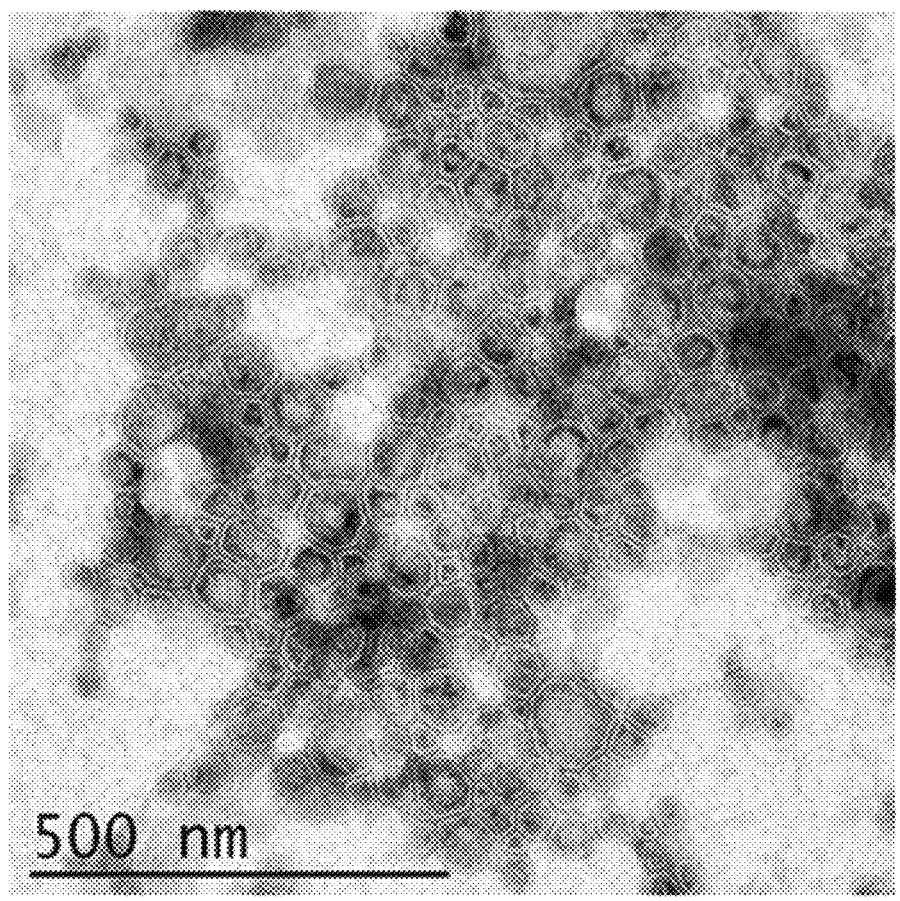
Figure 17C:
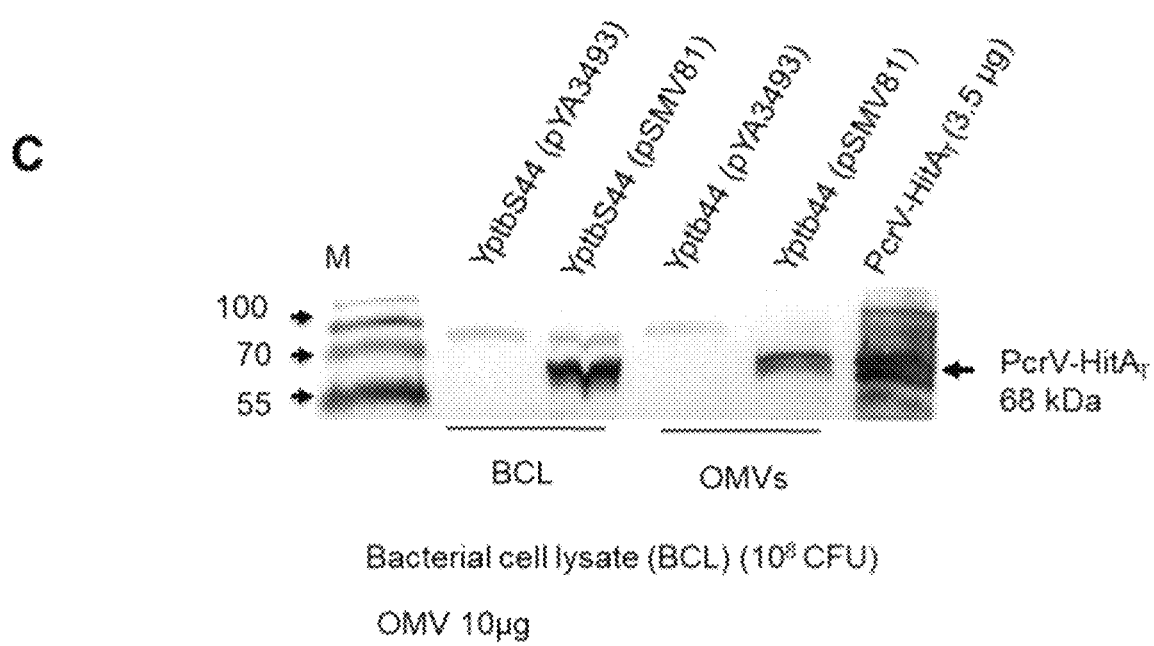

FIGS. 17A through 17C is a series of graphs of the production of OMVs in different Yptb PB1+ strains: FIG. 17A—Physical maps of Asd+ plasmids pSMV81 harboring the N-terminal β-lactamase signal sequence (bla ss) and codon-optimized pcrV-hitA fusion (PH); FIG. 17B—OMV isolated from YptbS-44 harboring pSMV81; FIG. 18C—PcrV-HitA (PH) fusion antigen synthesis was detected by immunoblotting with respective polyclonal rabbit antibody in whole cell lysate and OMVs of YptbS-44(pSMV81).

Figure 18A:
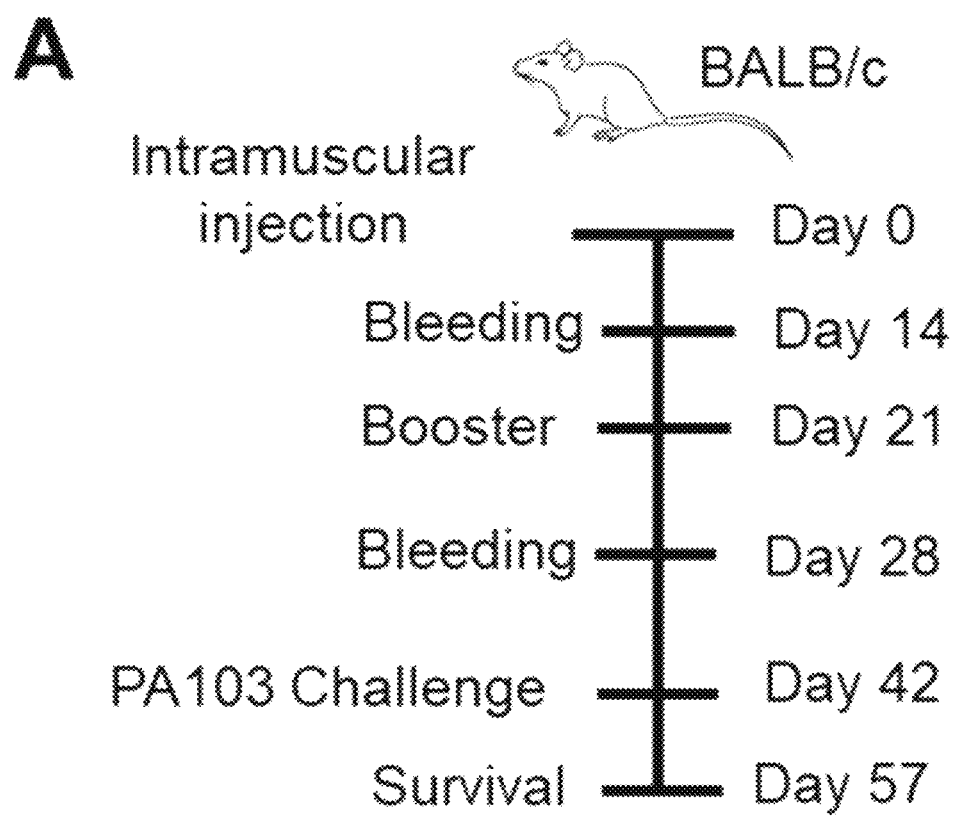
Figure 18B:
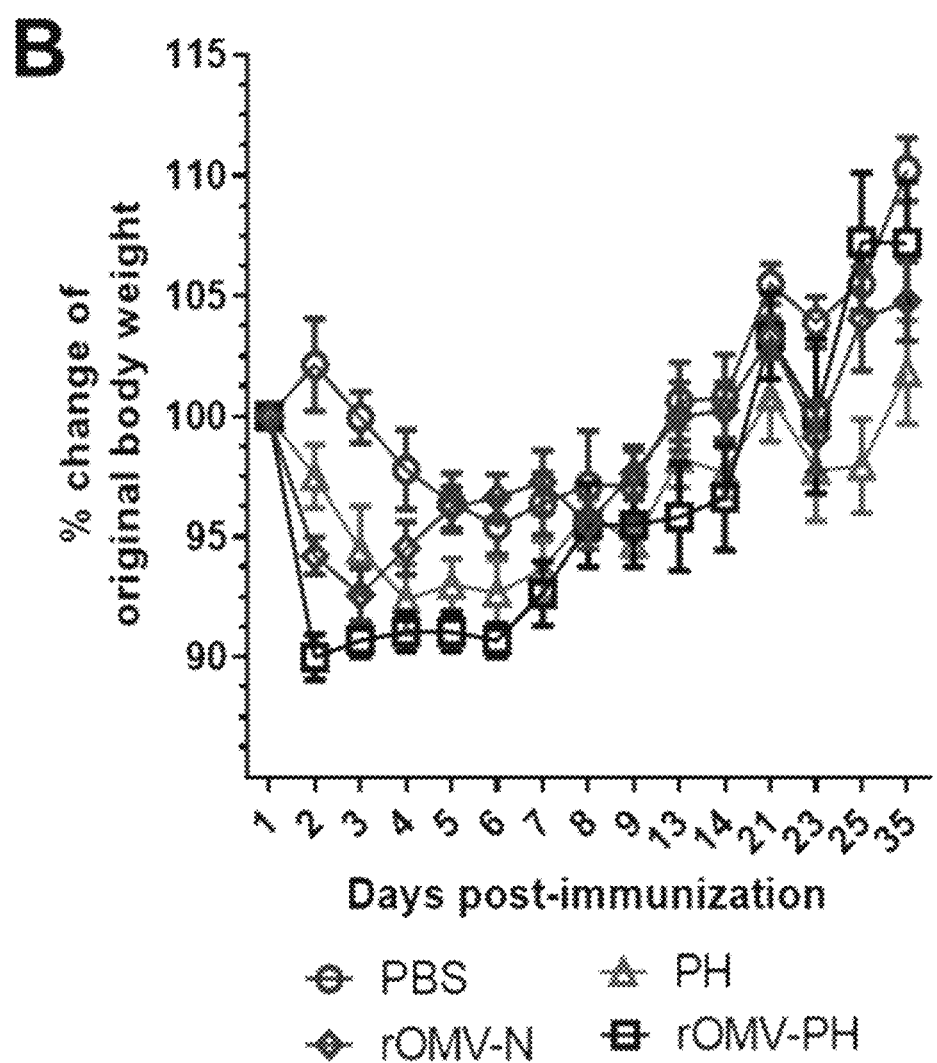
Figure 18C:
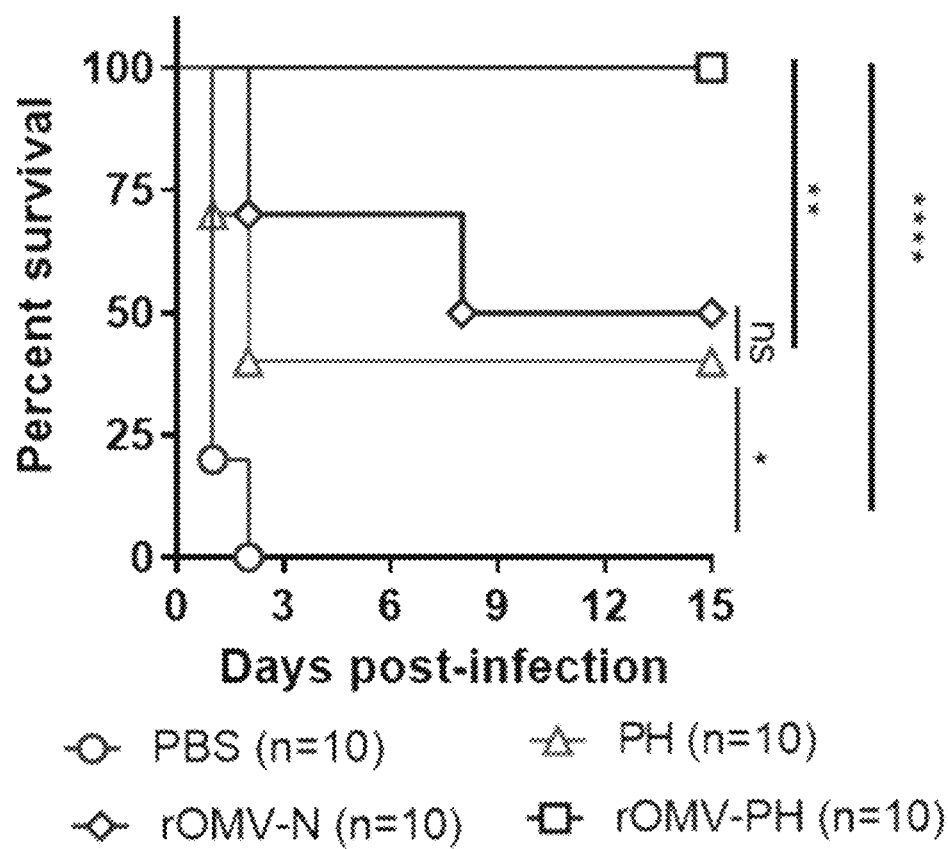
Figure 18D:
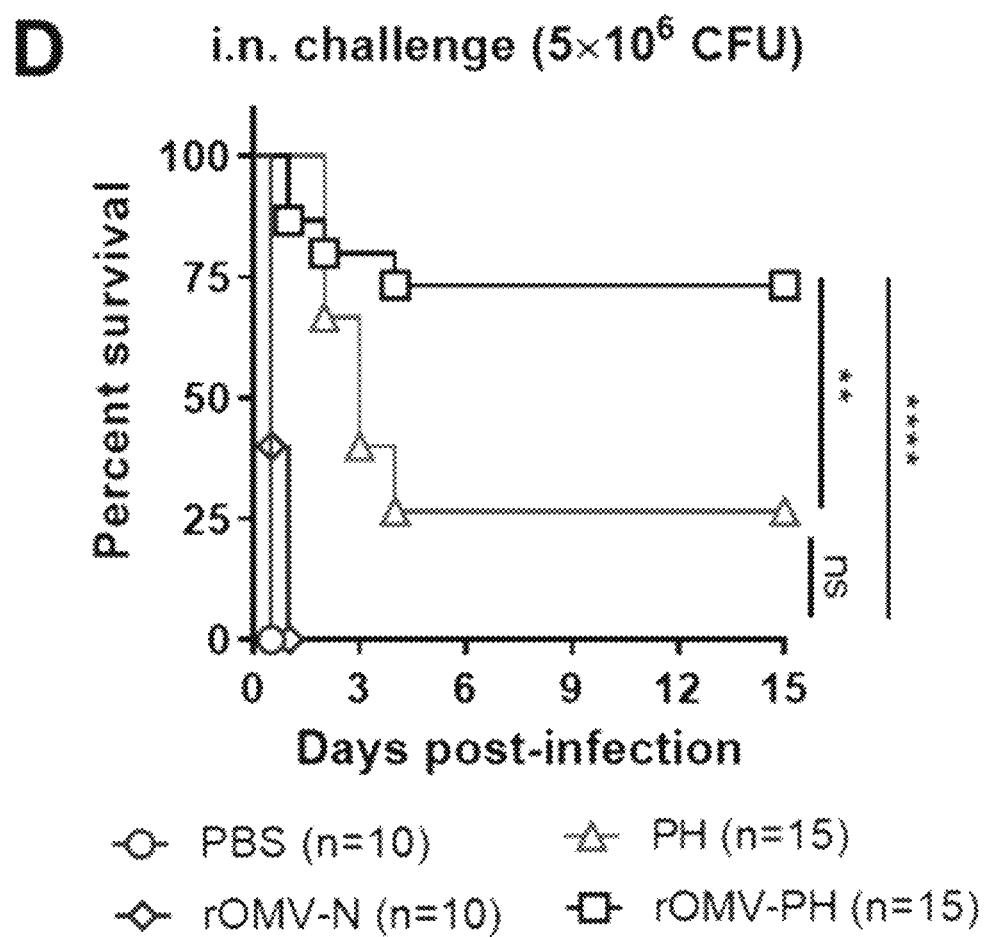

FIGS. 18A through 18D are a series of graphs of the survival of mice challenged by virulent P. aeruginosa PA103. FIG. 18A—Immunization scheme used for the mouse study; FIG. 18B—Rates of mouse body-weight change; FIG. 18C—OMV immunized- or PBS immunized-(sham) groups of BALB/c mice (10 mice per group, equal numbers of males and females) were subcutaneously challenged with 6.7×107 CFU of P. aeruginosa PA103. FIG. 18D—OMV immunized-, Broken OMV immunized- or PBS immunized-(sham) groups of BALB/c mice (10 mice per group, equal numbers of males and females) were intranasally challenged with 5×106 CFU of P. aeruginosa PA103. The experiments were performed twice, and data were combined for analysis. Statistical significance was analyzed by Log-rank (Mantel-Cox) test: ns, no significance; *, p<0.05; , p<0.01; **, p<0.0001.

Figure 19A:
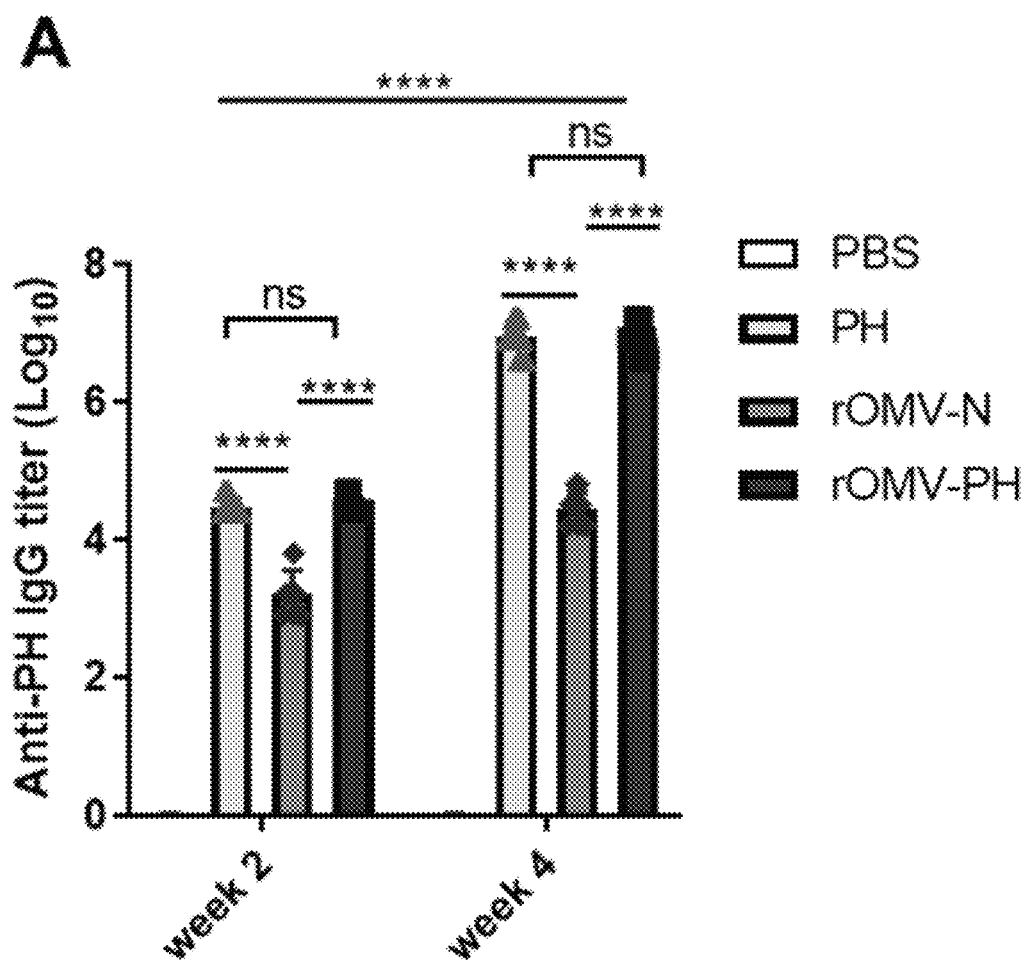
Figure 19B:
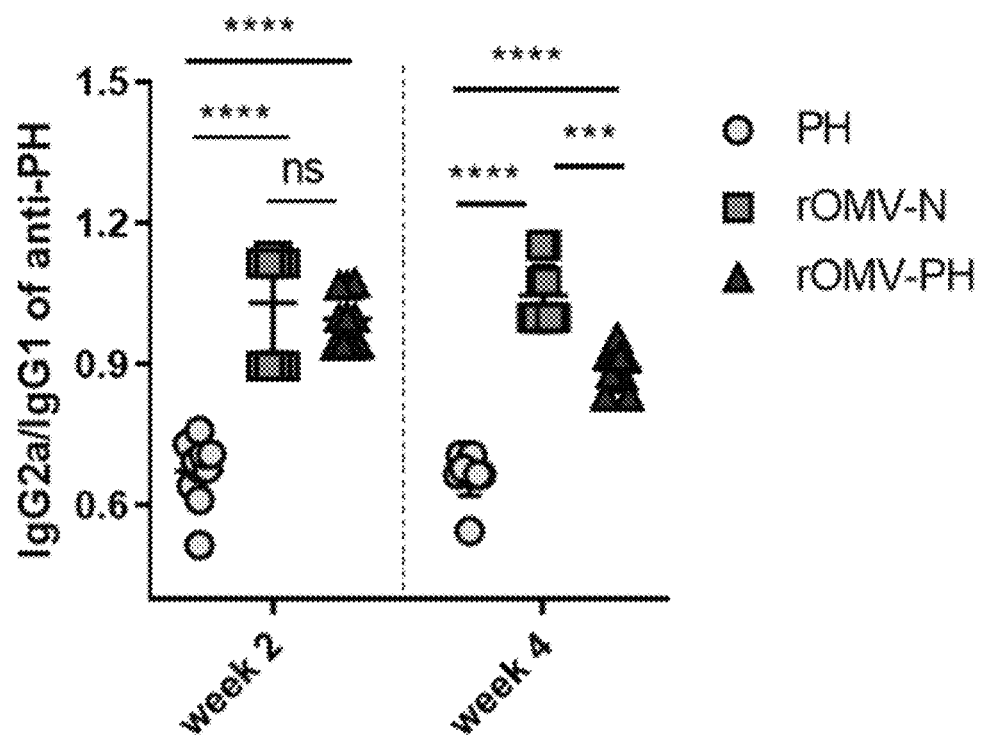
Figure 19C:
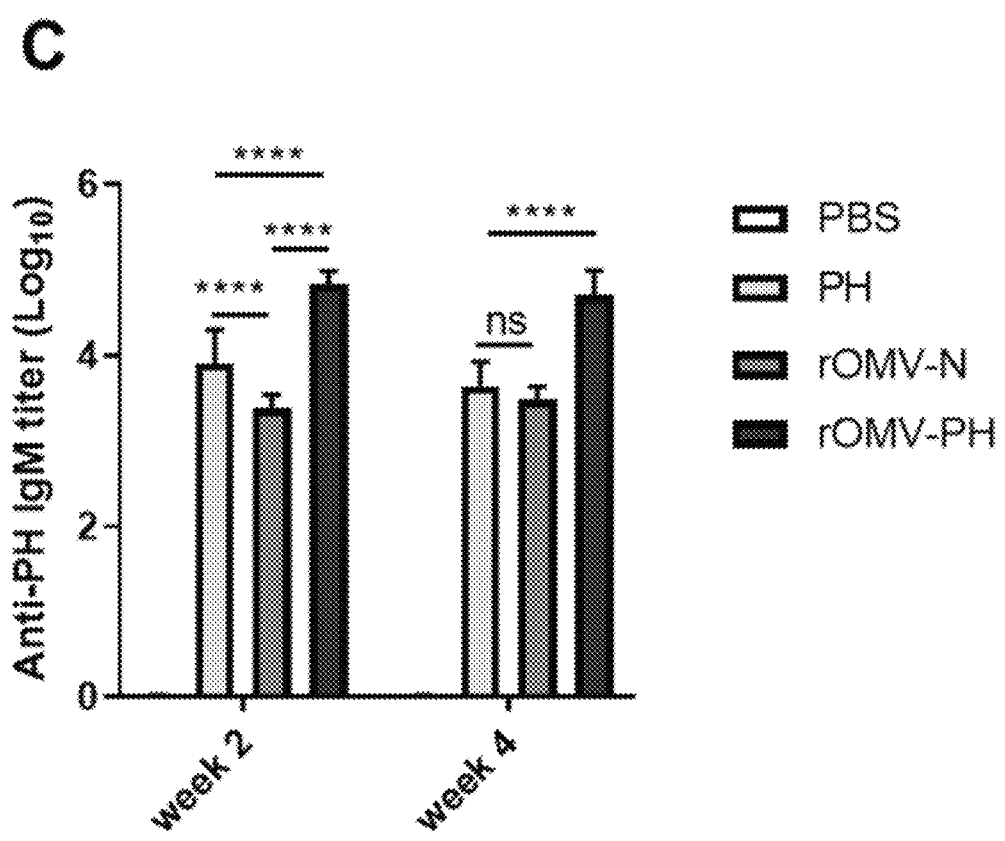
Figure 19D:
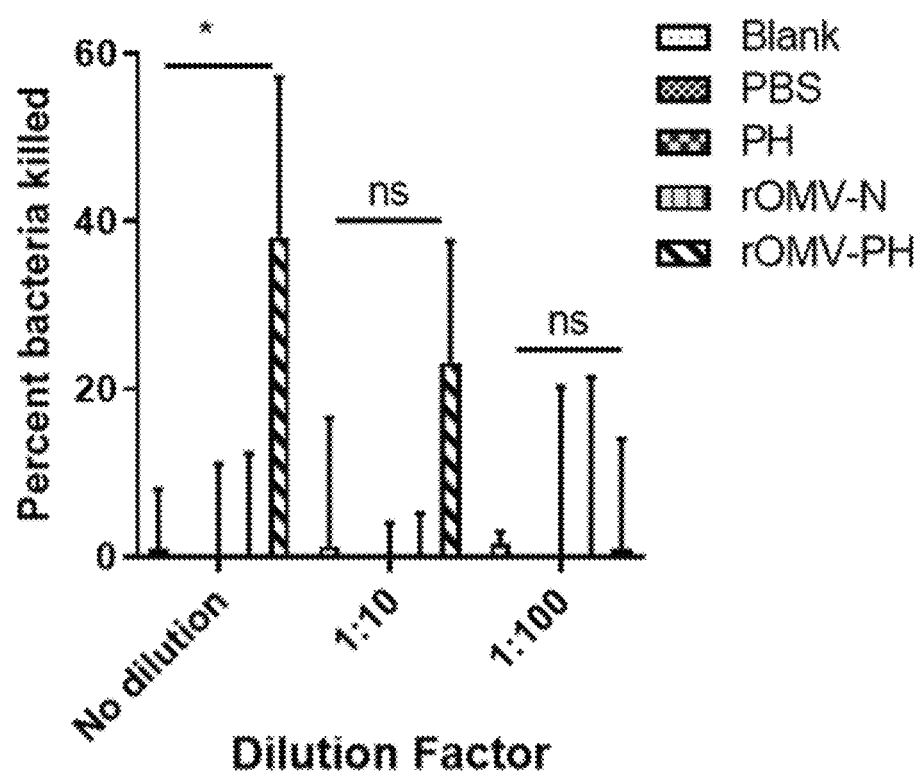

FIGS. 19A through 19D are a series of graphs of Antibody responses to PH fusion antigen in immunized mice and antibody opsonophagocytic killing capacity. BALB/c mice were immunized intramuscularly with 50 µg rOMVs/100 µl PBS, 10 µg PH/alhydrogel/100 µl PBS, or alhydrogel alone/100 µl PBS as negative controls and them boosted on day 21 after prime immunization. Blood was collected on days 14 and 28 and antigen-specific antibodies were determined by ELISA. Data represent 10 mice per group. FIG. 19A—Anti-PH total IgG titers at days 14 and 28 in different immunized mice. FIG. 19B—Ratios of IgG2a/IgG1 to the PH fusion antigen at days 14 and 28. FIG. 19C—Anti-PH IgM titers at days 14 and 28 in different immunized mice. FIG. 19D—Comparative analysis of opsonophagocytic killing activity against PA103 using anti-sera from different immunized mice. Data were shown as the mean±SD. The statistical significance among groups were analyzed by two-way multivariant ANOVA with a Tukey post hoc test: ns, no significance; *, p<0.05; , p<0.01; *, p<0.001; ****, p<0.0001.

Figure 20A:
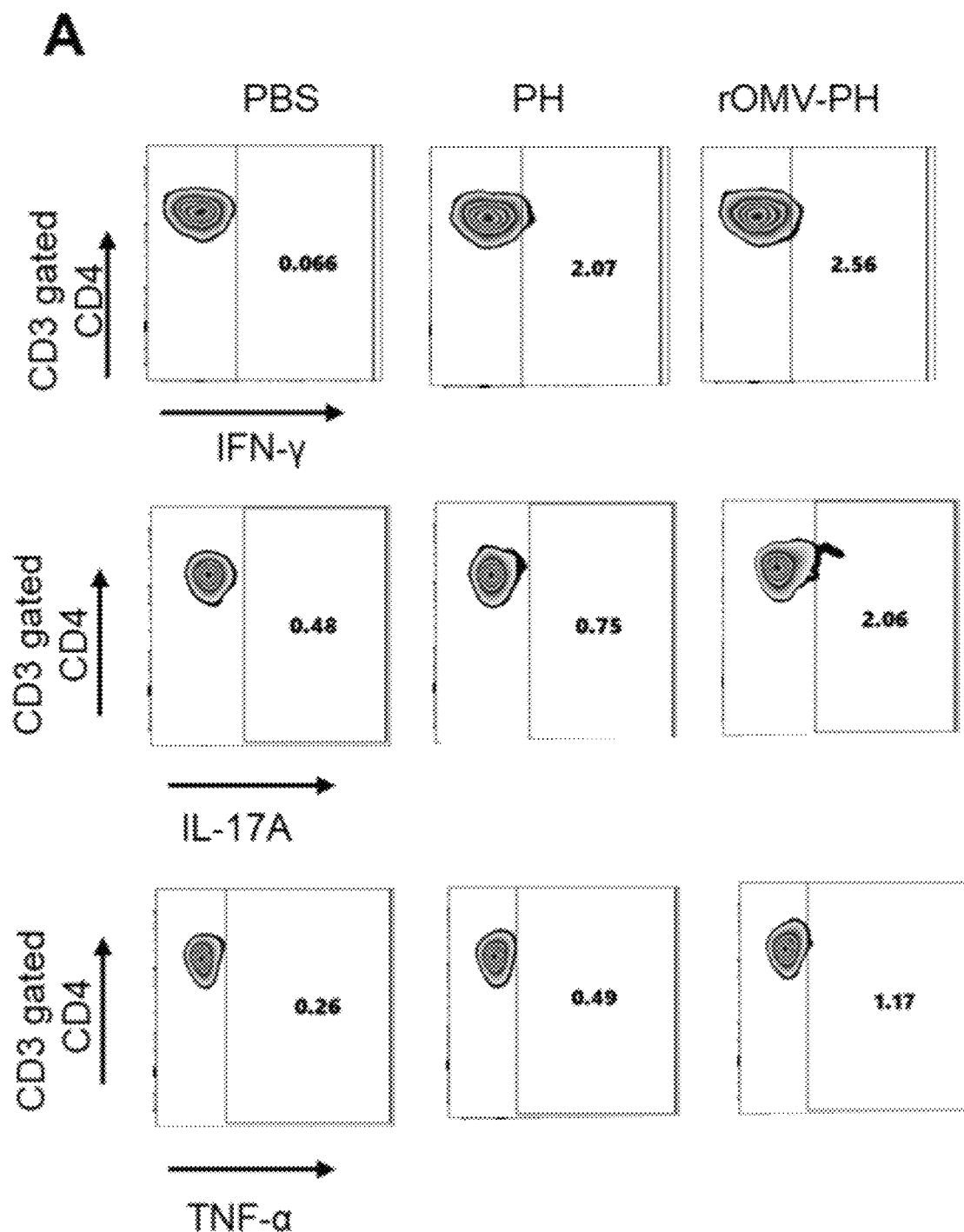
Figure 20B:
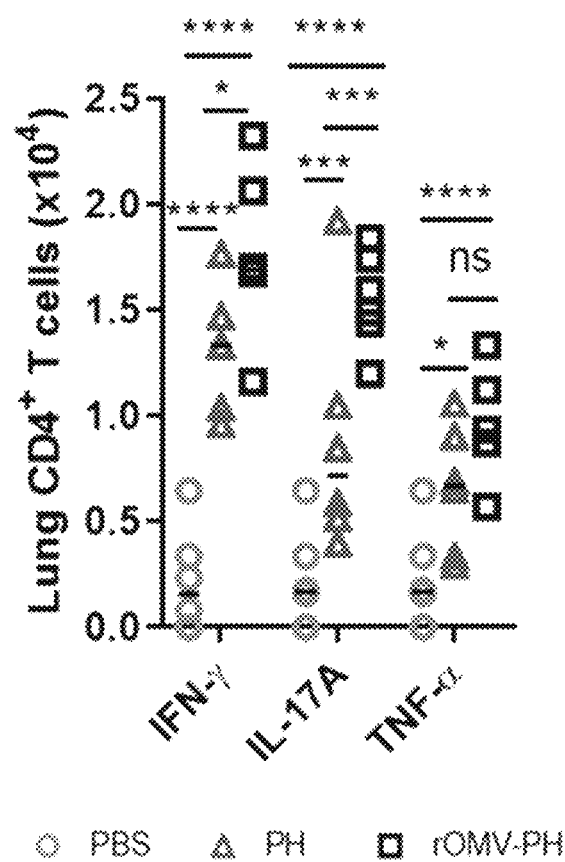
Figure 20C:
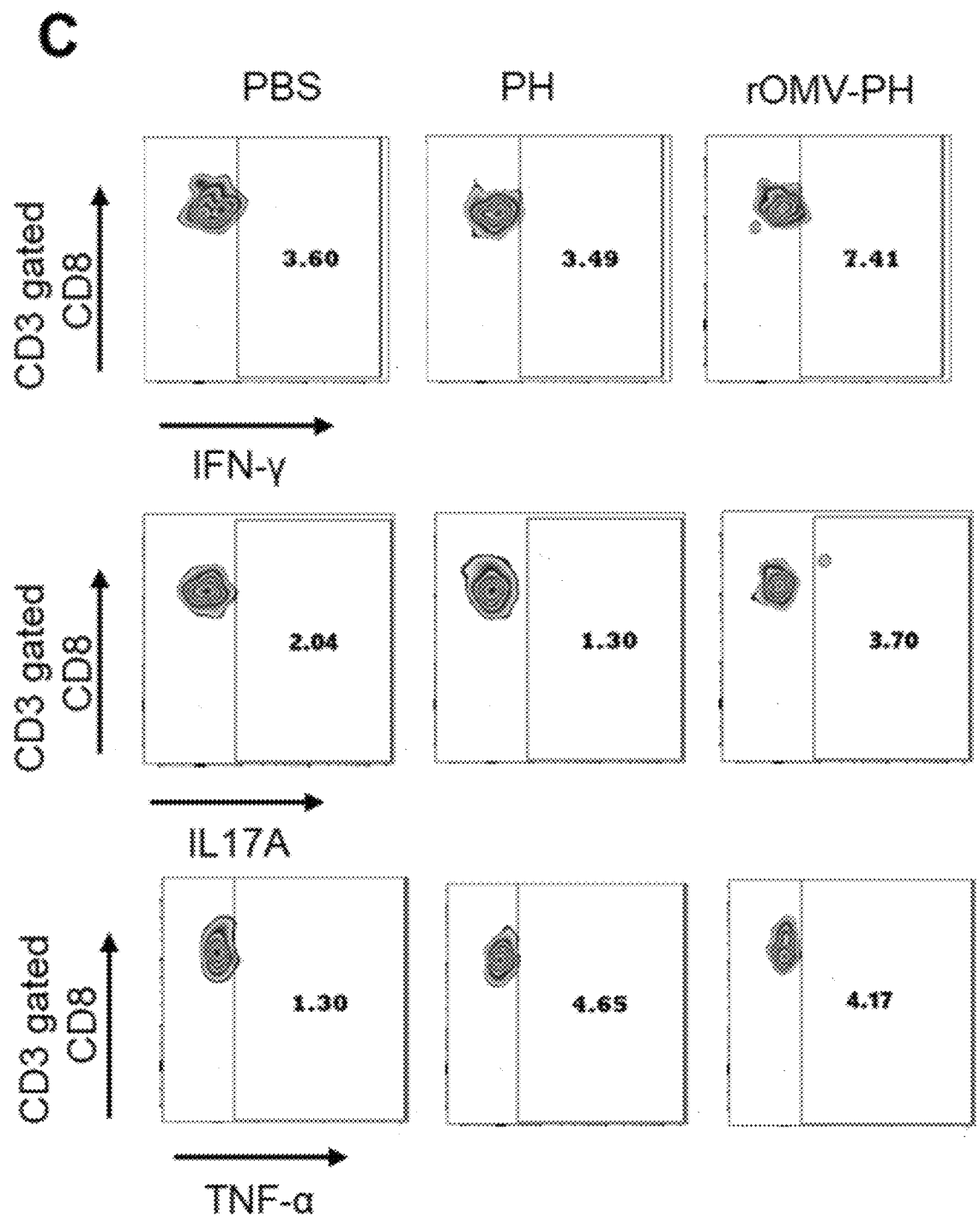
Figure 20D:
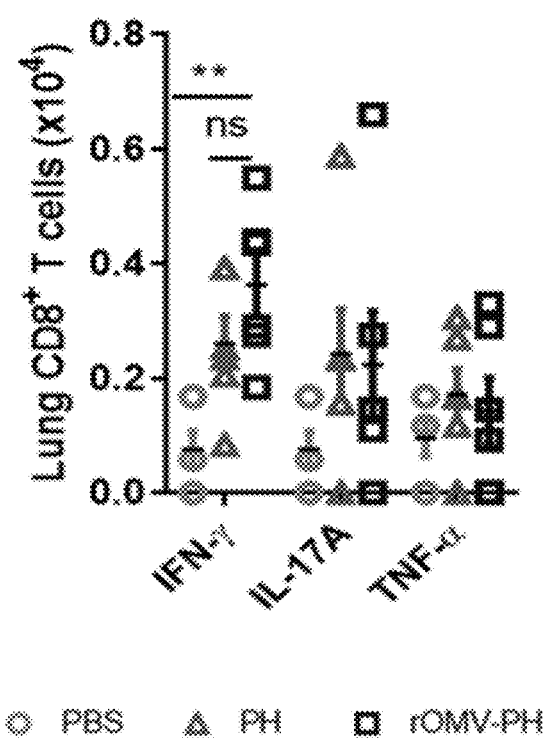
Figure 20E:
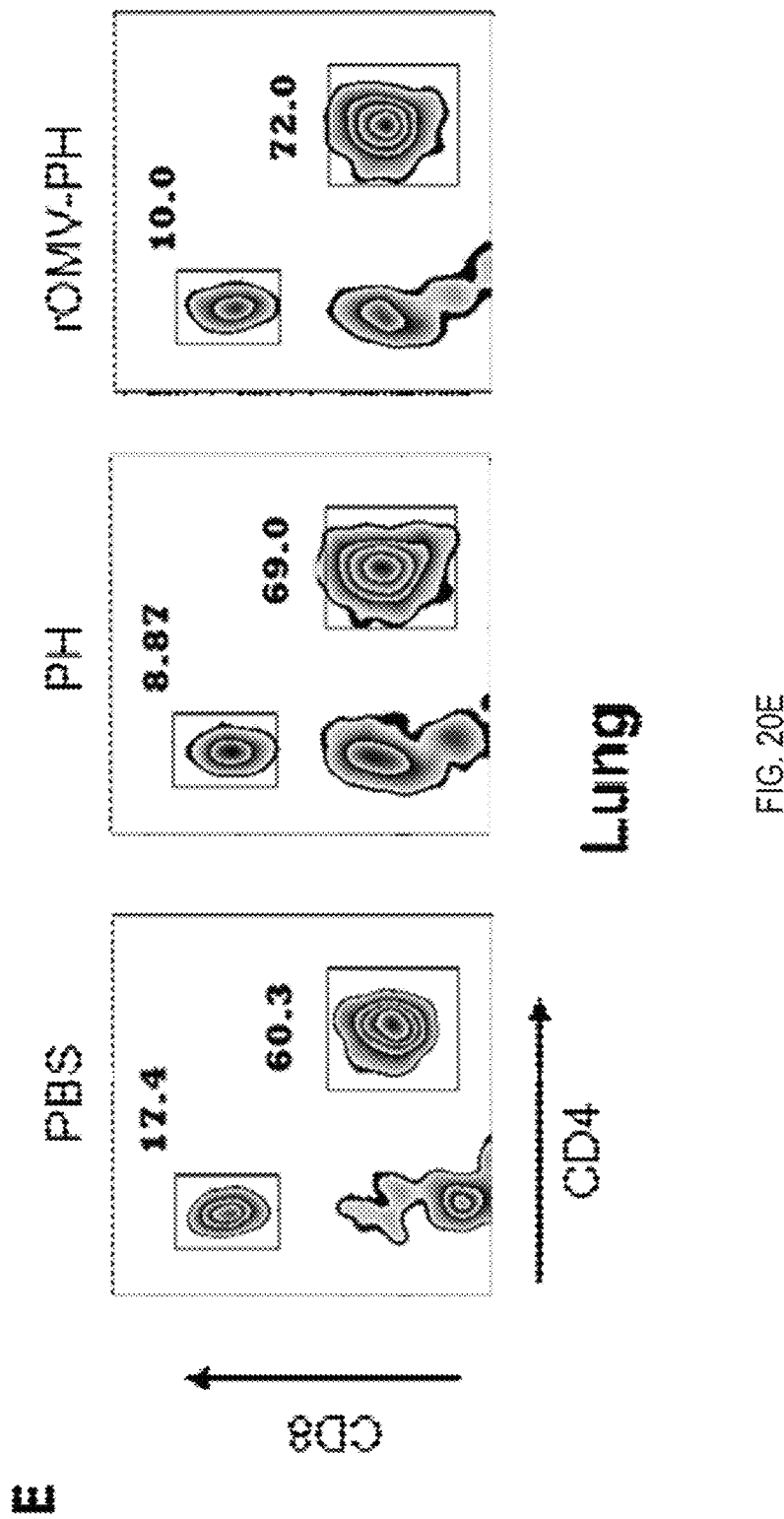
Figure 20F:
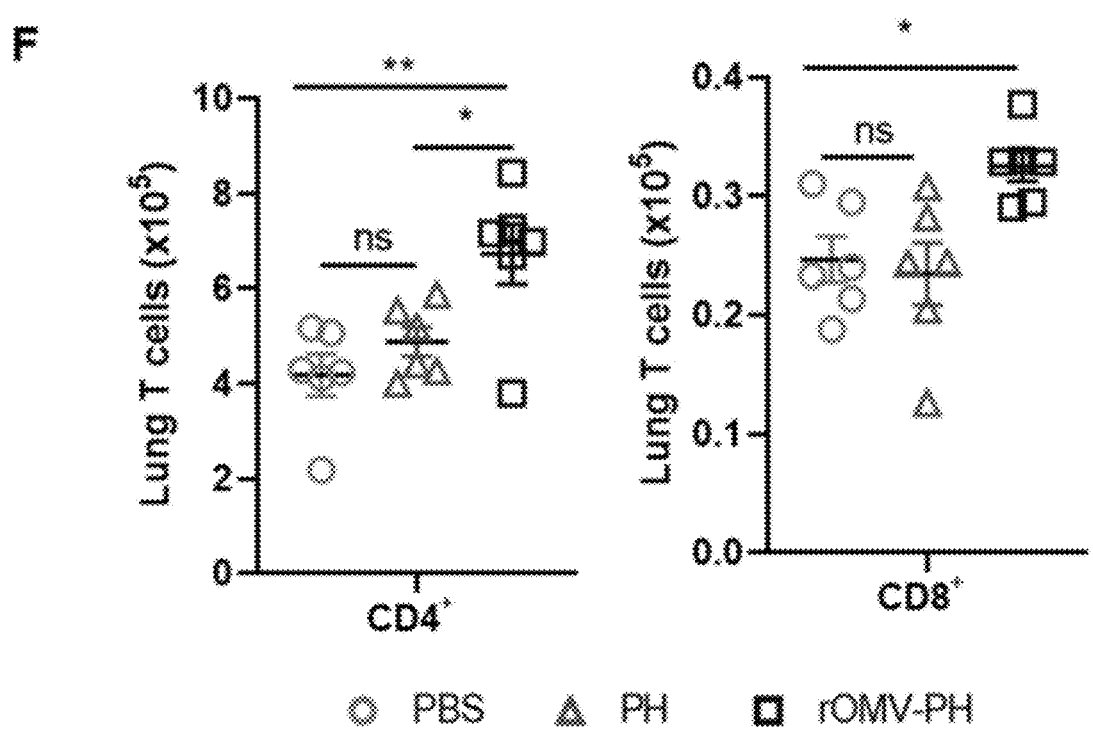

FIGS. 20A through 20F are a series of graph of Analysis of antigen-specific T cell responses obtained from lungs and associated cytokine production. On day 42 after the initial immunization, lung cells were aseptically isolated from mice (n=6) and stimulated in vitro with 20 µg/ml purified recombinant PH-His protein for 72 h to detect specific CD4+ and CD8+ T cells producing IFN-γ, IL-17 and TNF-α. Lung cells from PBS-immunized mice were considered as controls. FIG. 20A—Representative flow cytometry profiles of CD4+ T cells producing IFN-γ, IL-17 or TNF-α in the lungs of different immunized mice. FIG. 20B—Quantification of CD4+ IFN-γ+-, CD4+ IL-17+-, and CD4+ TNF-α+-positive cell numbers in the lungs of mice. FIG. 20C—Representative flow cytometry profiles of CD8+ T cells producing IFN-γ, IL-17 or TNF-α in the lungs of different immunized mice. FIG. 20D—Quantification of CD8+ IFN-γ+-, CD8+ IL-17+-, and CD8+ TNF-α+-positive cell numbers in the lungs of mice. FIG. 20E—Representative flow cytometry profiles of CD4+ and CD8+ T cells in 85 the lungs of different immunized mice after stimulation. FIG. 20F—Quantification of CD4+ and CD8+ 86 T-cell numbers in the lungs of mice. Each symbol represents a data point obtained from an individual mouse, with mean±SD. The experiments were performed twice, and data were combined for analysis. The statistical significance among the groups were analyzed by two-way multivariant ANOVA with a Tukey post hoc test: ns, no significance; *, p<0.05; , p<0.01; *, p<0.001; ****, p<0.0001. Abbreviations: interferon (INF)-γ; tumor necrosis factor (TNF)-α.

Figure 21A:
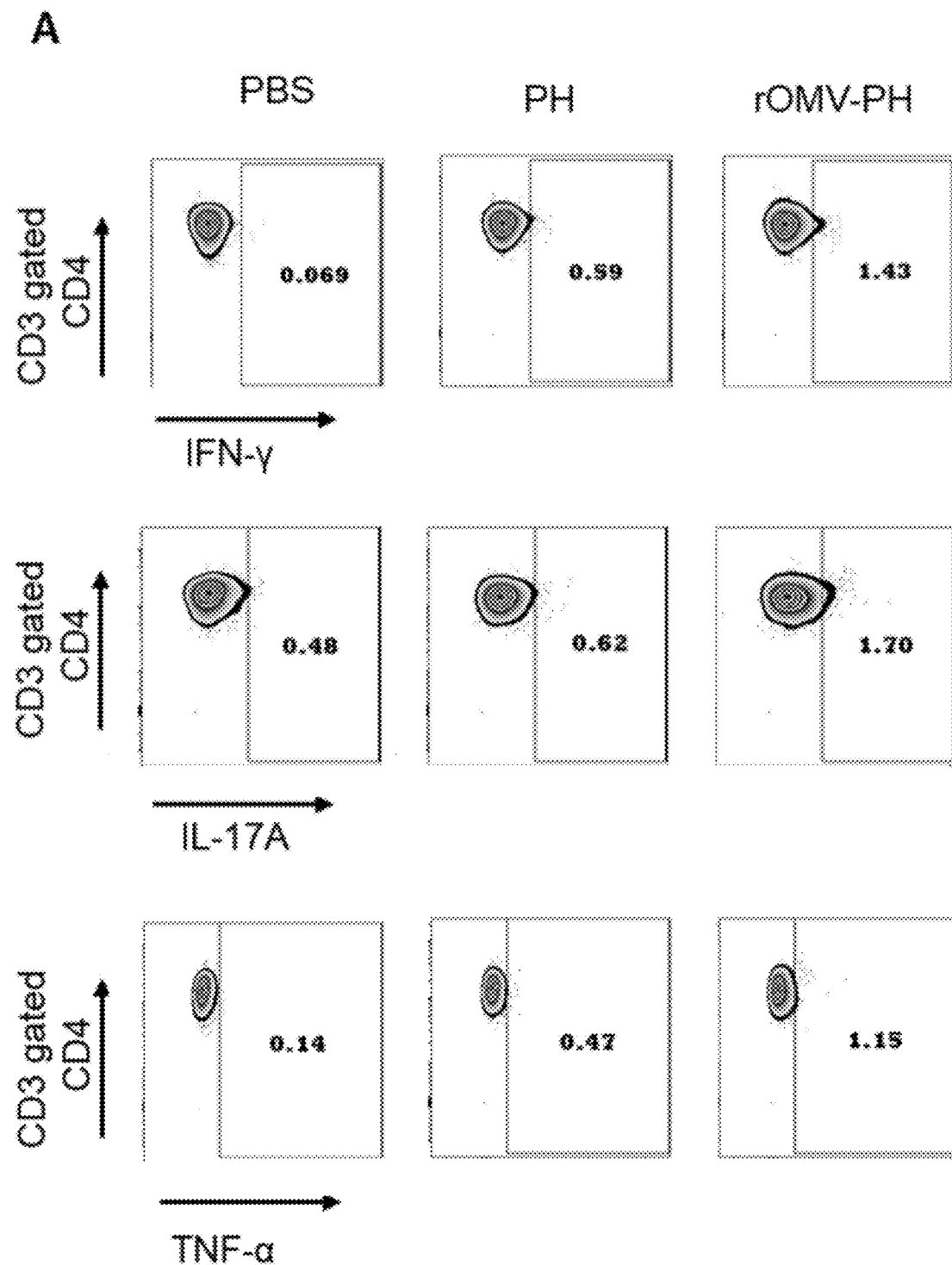
Figure 21B:
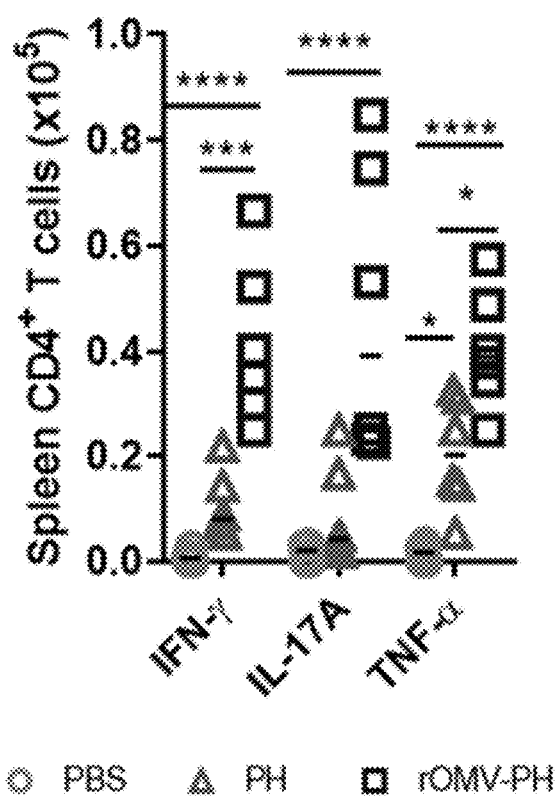
Figure 21C:
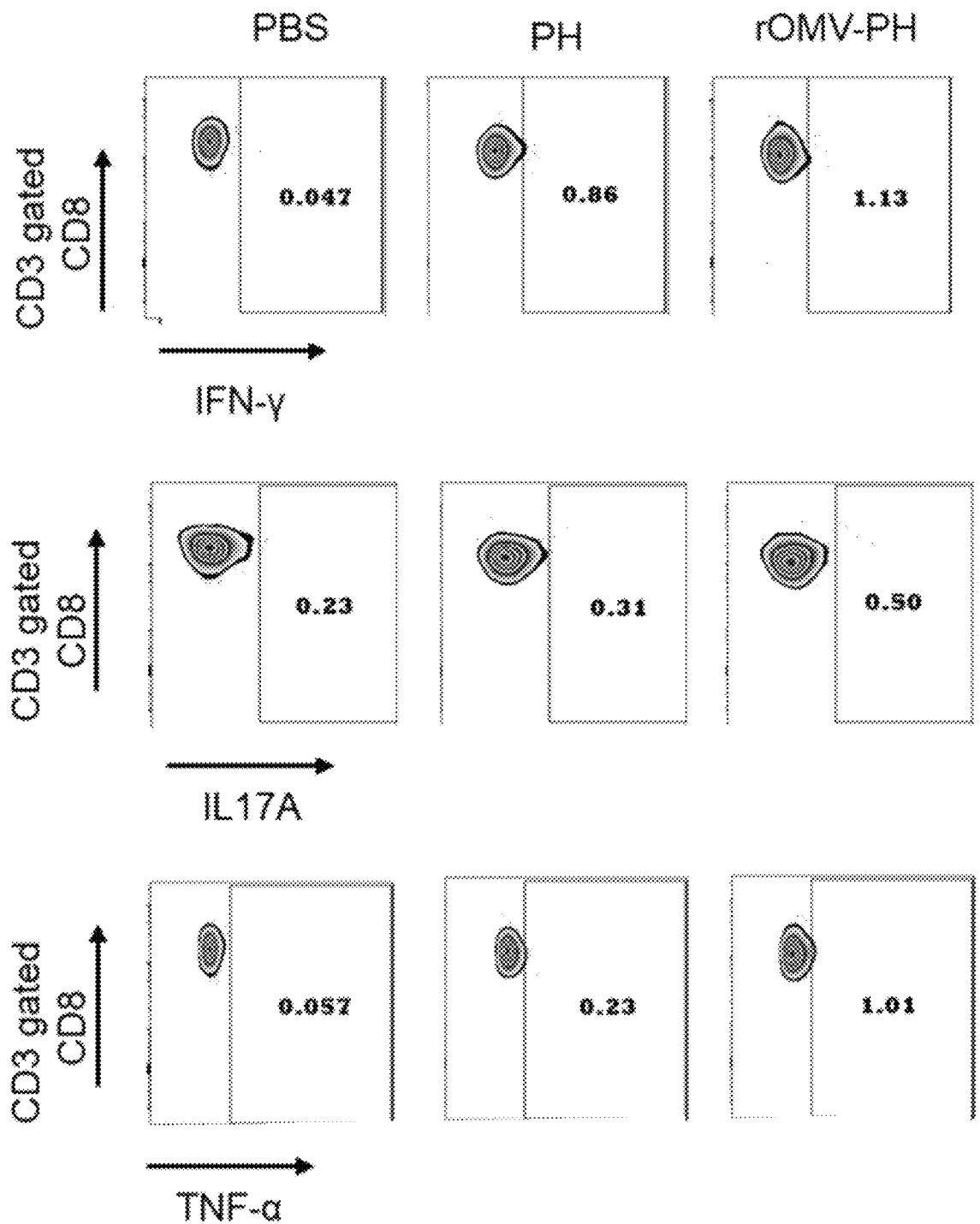
Figure 21D:
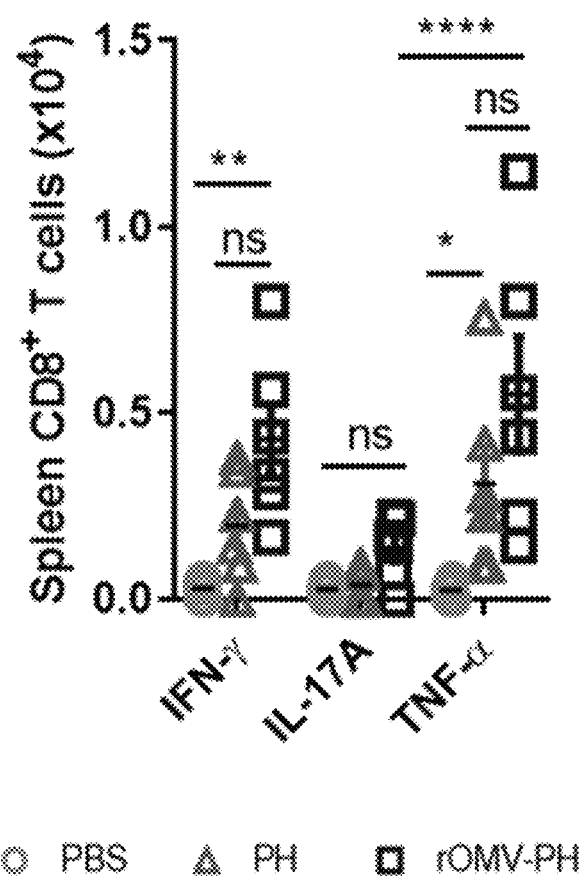
Figure 21E:
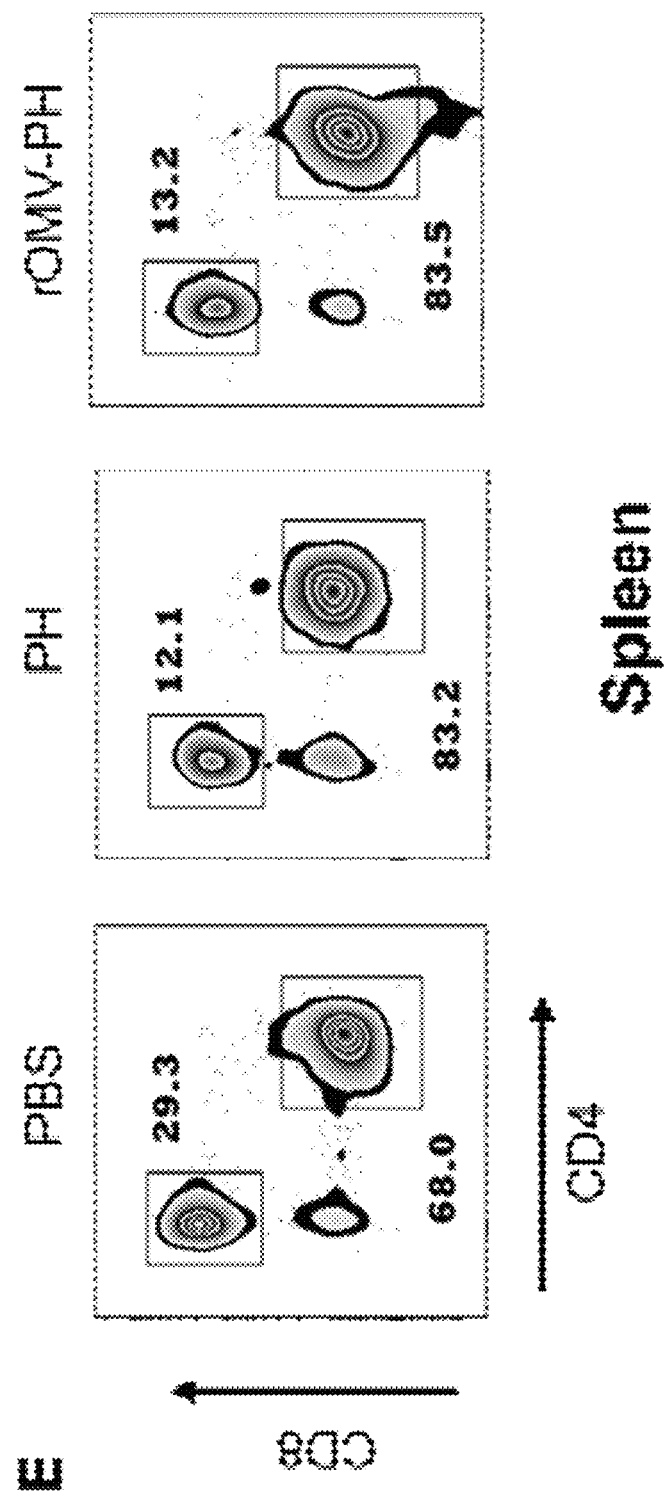
Figure 21F:
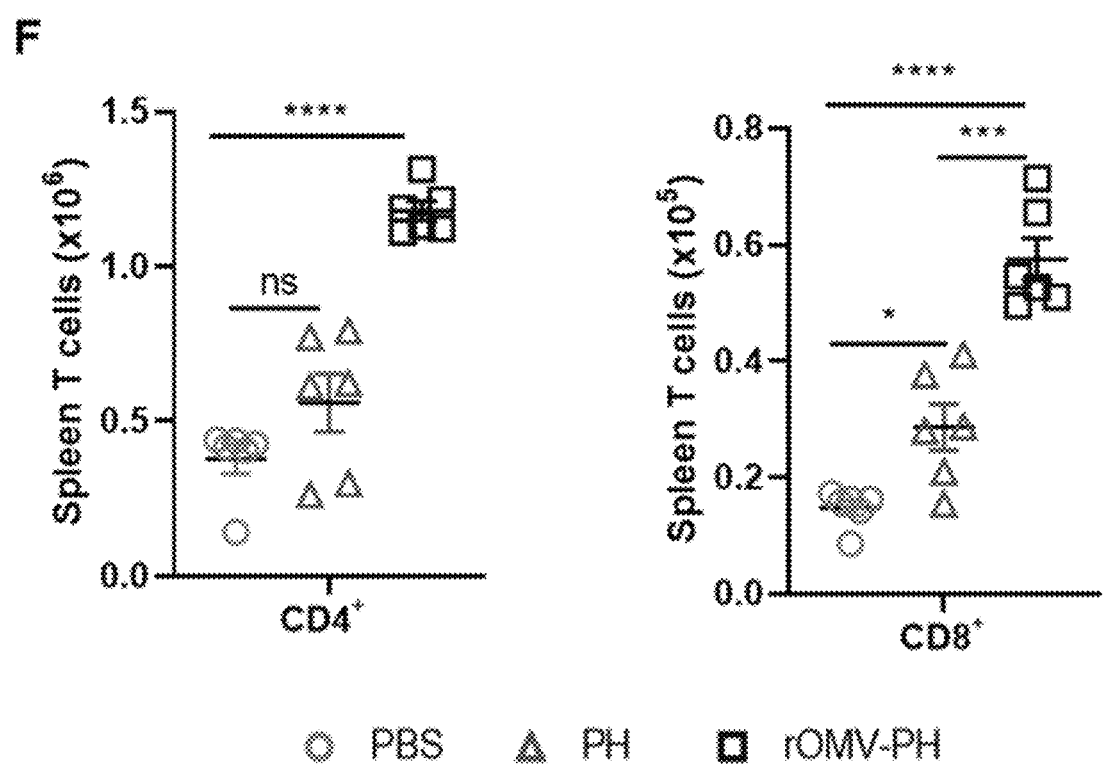

FIGS. 21A through 21F are a series of graph of Analysis of antigen-specific T cell responses obtained from spleens and associated cytokine production. On day 42 after the initial immunization, splenic cells were aseptically isolated from mice (n=6) and stimulated in vitro with 20 µg/ml purified recombinant PH-His protein for 72 h to detect specific CD4+ and CD8+ T cells encoding IFN-γ, IL-17 and TNF-α. Splenic cells from PBS-immunized mice were considered as controls. FIG. 21A—Representative flow cytometry profiles of CD4+ T cells producing IFN-γ, IL-17 or TNF-α in the spleens of different immunized mice. FIG. 21B—Quantification of CD4+ IFN-γ+-, CD4+ IL-17+-, and CD4+ TNF-α+-positive cell numbers in the spleens of mice. FIG. 21C—Representative flow cytometry profiles of CD8+ T cells producing IFN-γ, IL-17 or TNF-α in the spleens of different immunized mice. FIG. 21D—Quantification of CD8+ IFN-γ+-, CD8+ IL-17+-, and CD8+ TNF-α+-positive cell numbers in the spleens of mice. FIG. 21E—Representative flow cytometry profiles of CD4+ and 87 CD8+ T cells in the spleens of different immunized mice after stimulation. FIG. 21F—Quantification of 88 CD4+ and CD8+ T-cell numbers in the spleens of mice. Each symbol represents a data point obtained from an individual mouse, with mean±SD. The experiments were performed twice, and data were combined for analysis. The statistical significance among the groups were analyzed by two-way multivariant ANOVA with a Tukey post hoc test: ns, no significance; *, p<0.05; , p<0.01; *, p<0.001; ****, p<0.0001.

Figure 22A:
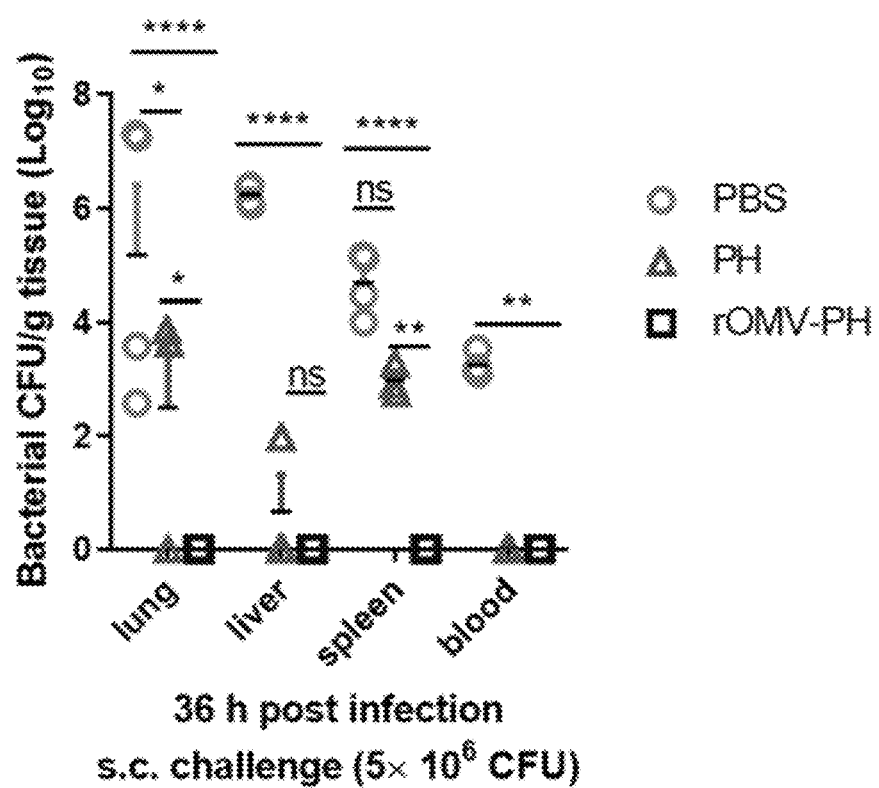
Figure 22B:
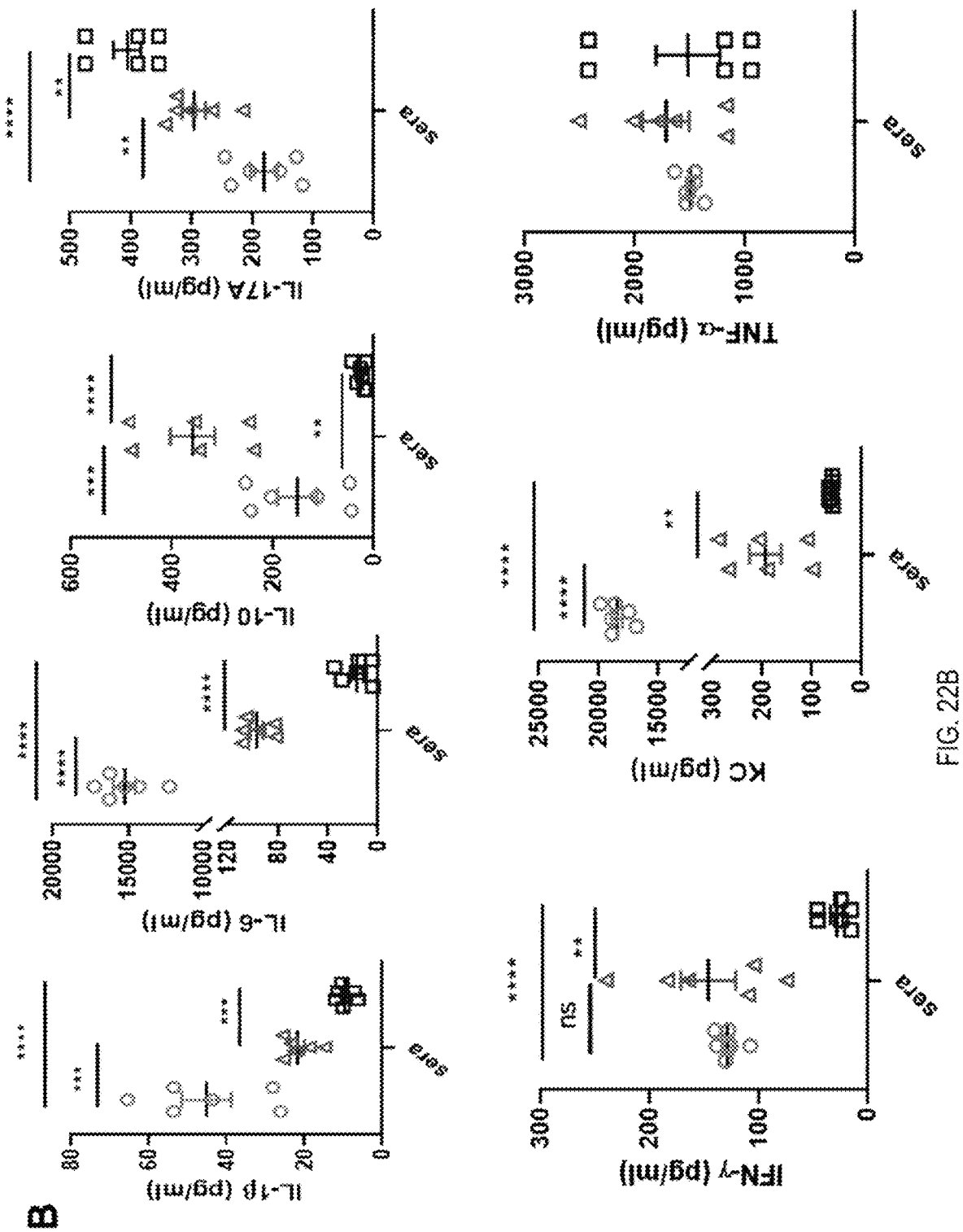

FIGS. 22A through 22B are a series of graphs of In vivo responses after s.c. challenge with *P. aeruginosa* PA103. PBS-, PH- or rOMV-PH-immunized BALB/c mice (n=6) were infected s.c. with a sublethal dose (5×106 CFU) of PA103. On 36-h post challenge, different tissues (lung, liver spleen and blood) were collected from euthanized mice. FIG. 22A—Bacterial burden was evaluated in the lungs, livers, spleens, and blood. FIG. 22B—Amounts of cytokine/chemokine (IL-1β, IL-6, IL-10, IL-17A, IFN-γ, KC and TNF-α) in sera from immunized mice on 36-h post infection. Data were shown as the mean±SD. The experiments were performed twice, and data were combined for analysis. The statistical significance among the groups were analyzed by two-way multivariant ANOVA with a Tukey post hoc test: ns, no significance; *, p<0.05; , p<0.01; *, p<0.001; ****, p<0.0001.

Figure 23A:
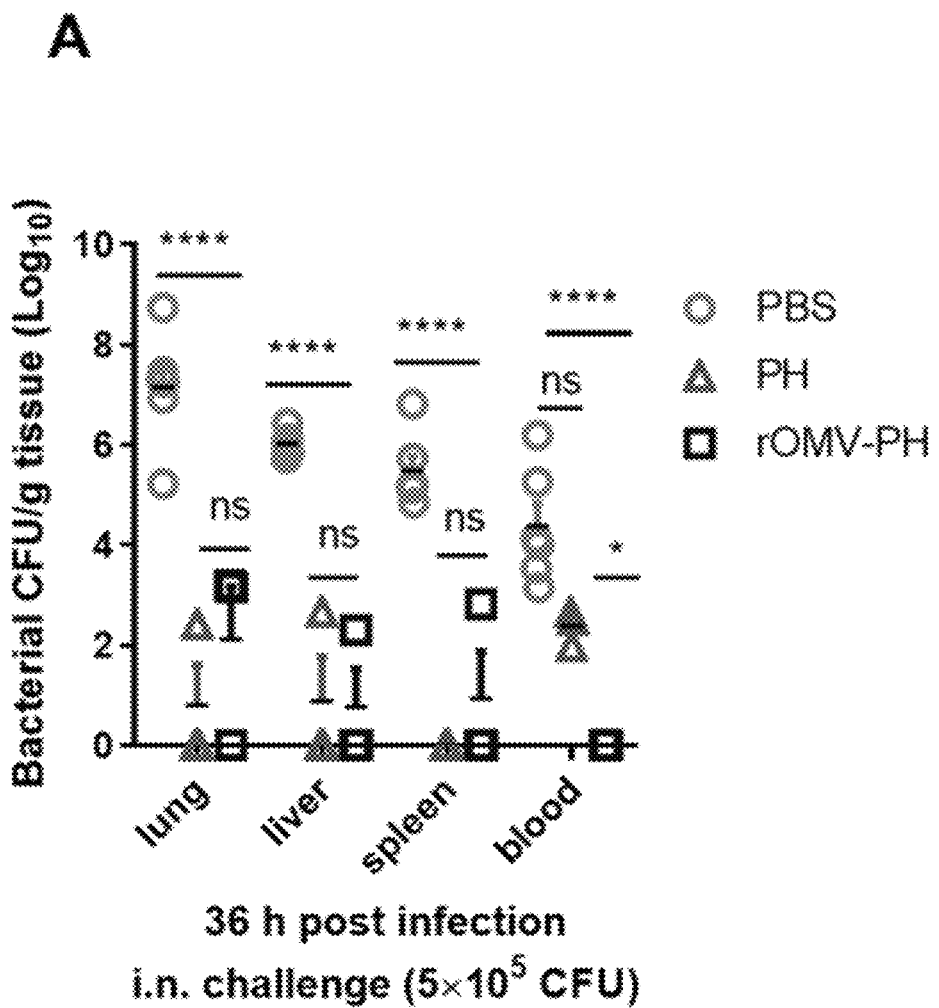
Figure 23B:
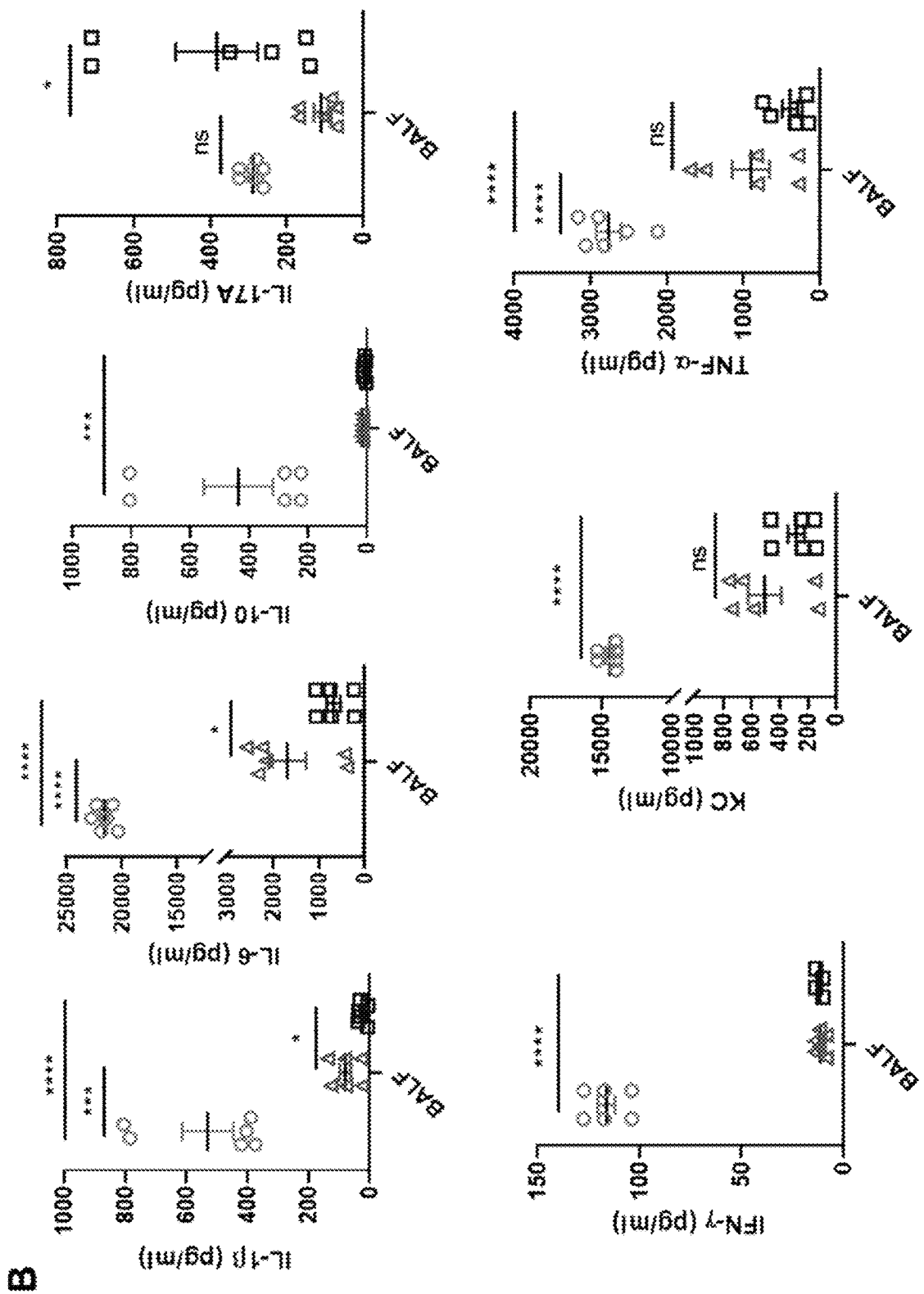

FIGS. 23A through 23B are a series of graphs of In vivo responses after i.n. challenge with *P. aeruginosa* PA103. PBS-, PH- or rOMV-PH-immunized BALB/c mice (n=6) were infected i.n. with a sublethal dose (5×105 CFU) of PA103. On 36-h post challenge, different tissues (lung, liver spleen and blood) were collected from euthanized mice. FIG. 23A—Bacterial burden was evaluated in the lungs, livers, spleens, and blood. FIG. 23A—Amounts of cytokine/chemokine (IL-1β, IL-6, IL-10, IL-17A, IFN-γ, KC and TNF-α) in Bronchoalveolar lavage fluid (BALF) from immunized mice on 36-h post infection. Data were shown as the mean±SD. The experiments were performed twice, and data were combined for analysis. The statistical significance among the groups were analyzed by two-way multivariant ANOVA with a Tukey post hoc test: ns, no significance; *, p<0.05; , p<0.01; *, p<0.001; ****, p<0.0001.

Figure 24A:
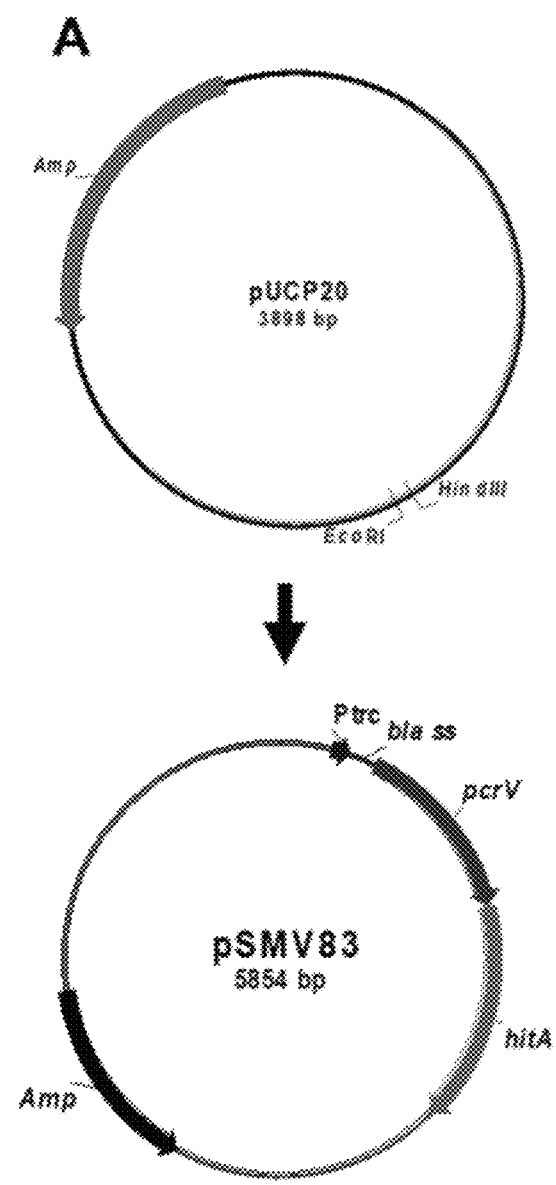
Figure 24B:
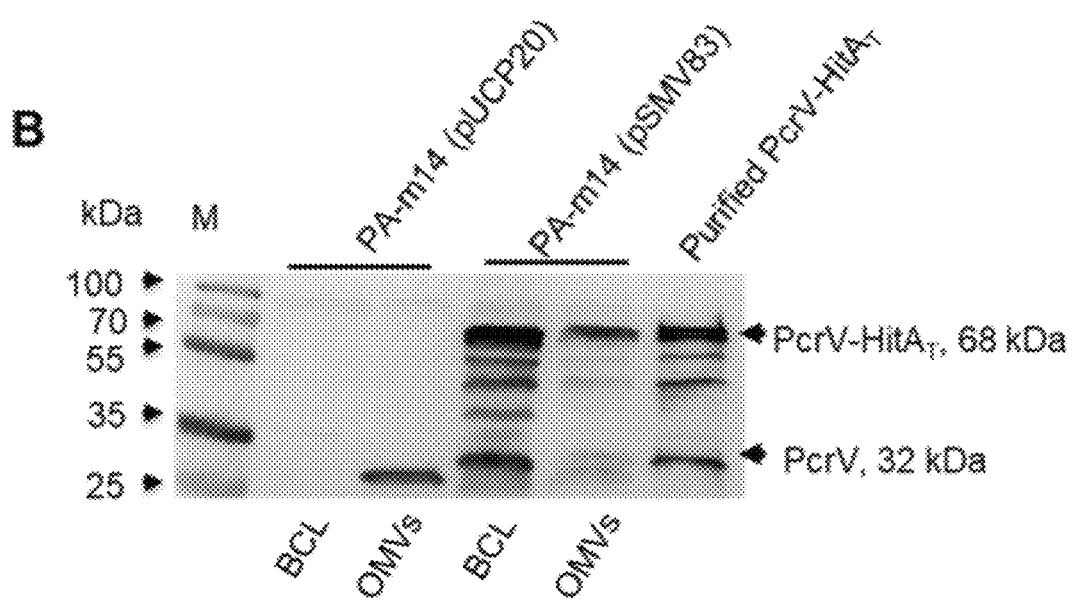
Figure 24C:
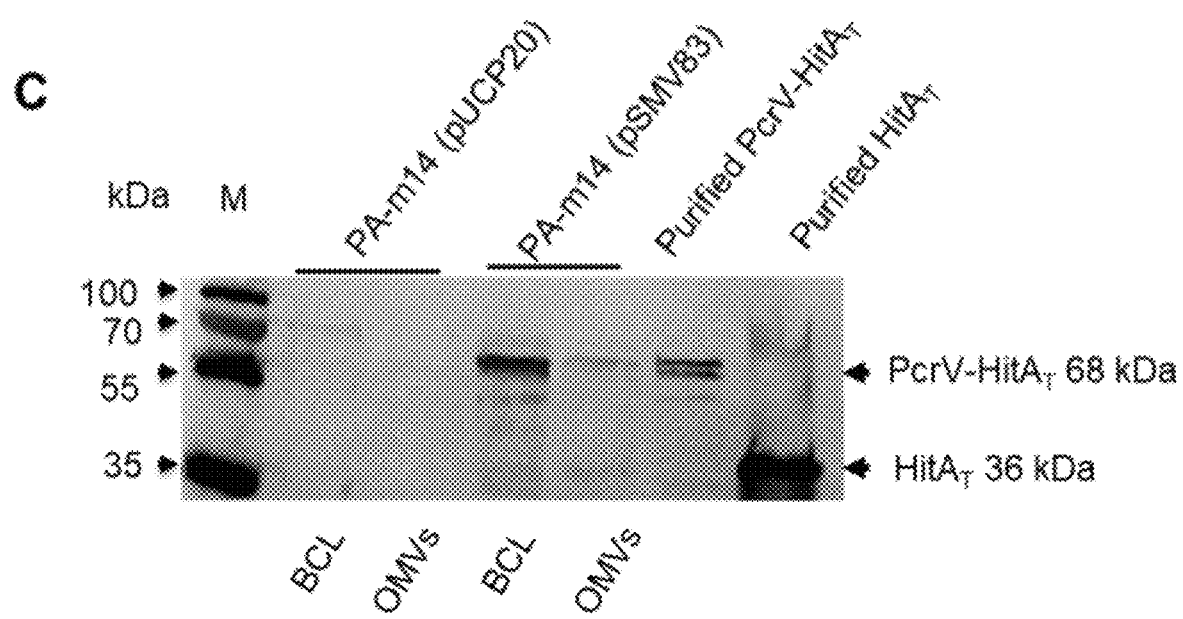

FIGS. 24A through 24C are a series of graphs of Enhancement of the PcrV-HitAT fusion antigen (PH) in *P. aeruginosa* OMVs. FIG. 24A—Physic map of pSMV83 plasmid containing a fusion gene encoding PH fusion antigen; FIG. 24B—Western blot analyzed the PH fusion antigen synthesis in BCL and OMVs of wild-type PA103 or mutant PA104-m14 by mouse anti-PcrV antibody using western blot; FIG. 24C—Western blot analyzed the PH fusion antigen synthesis in BCL and OMVs of wild-type PA103 or mutant PA104-m14 by mouse anti-HitAT antibody.

Figure 25A:
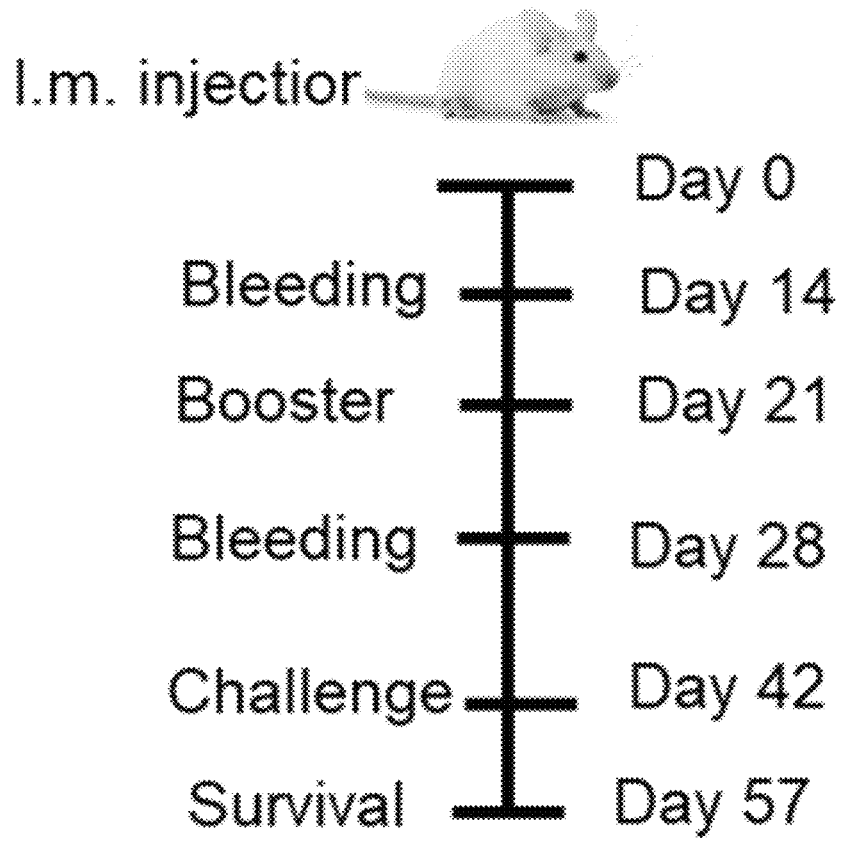
Figure 25B:
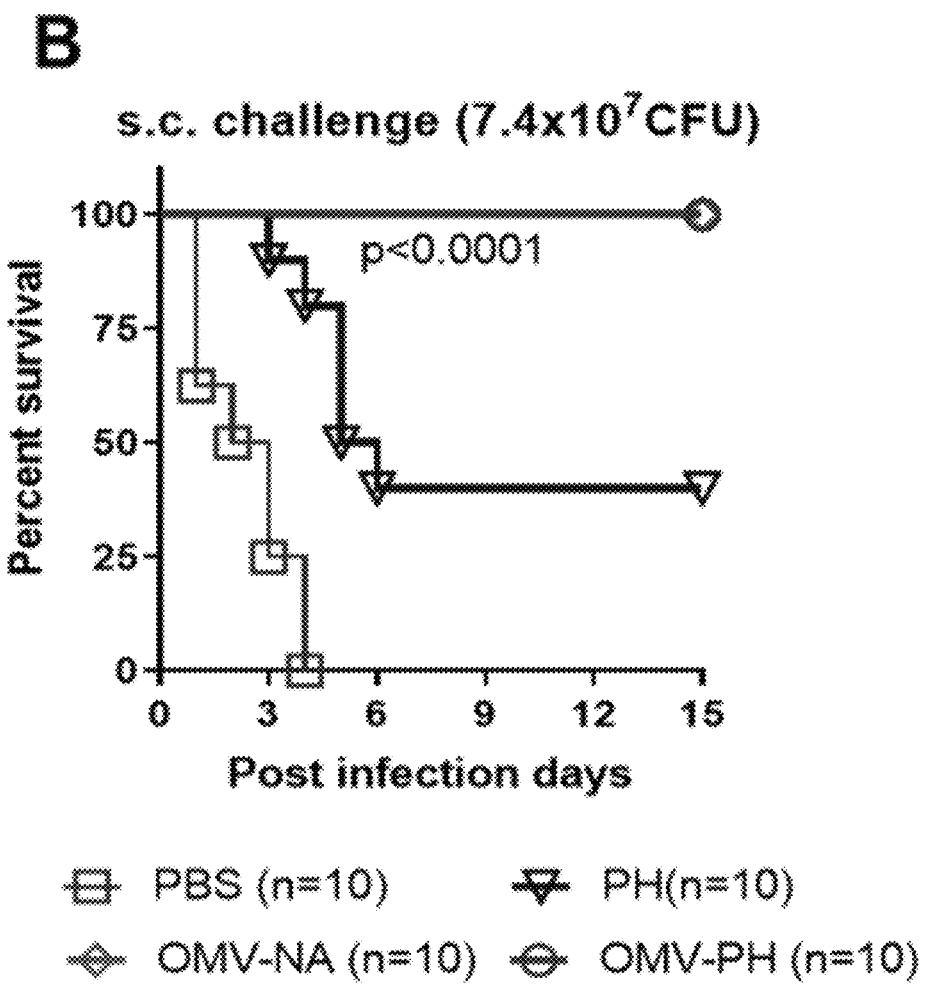
Figure 25C:
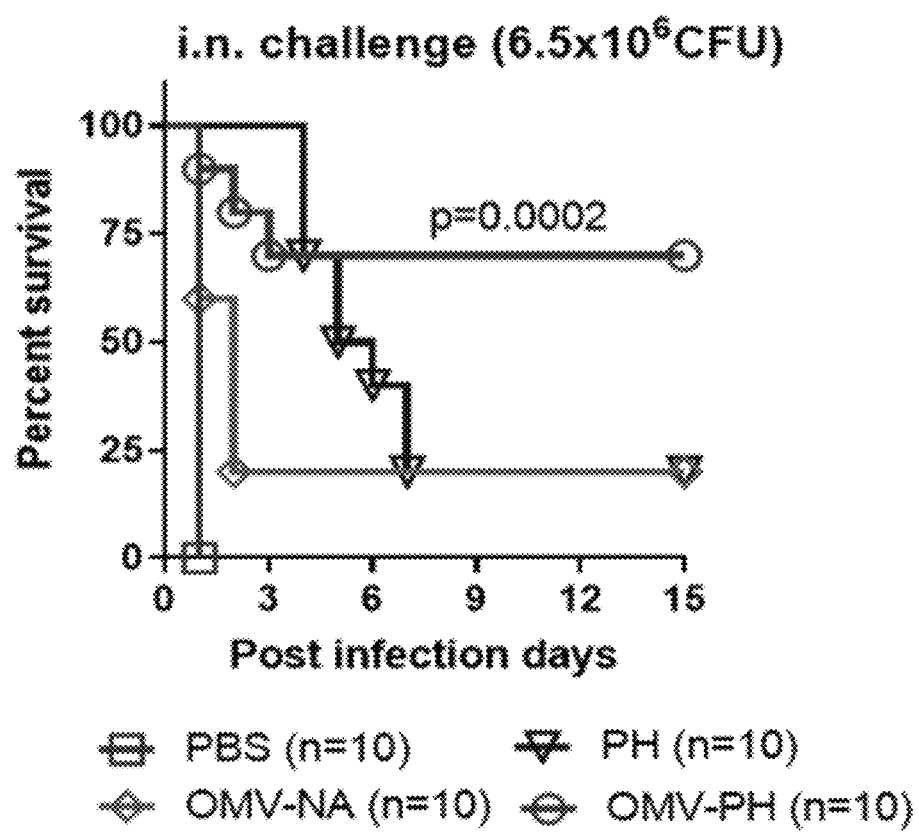
Figure 25D:
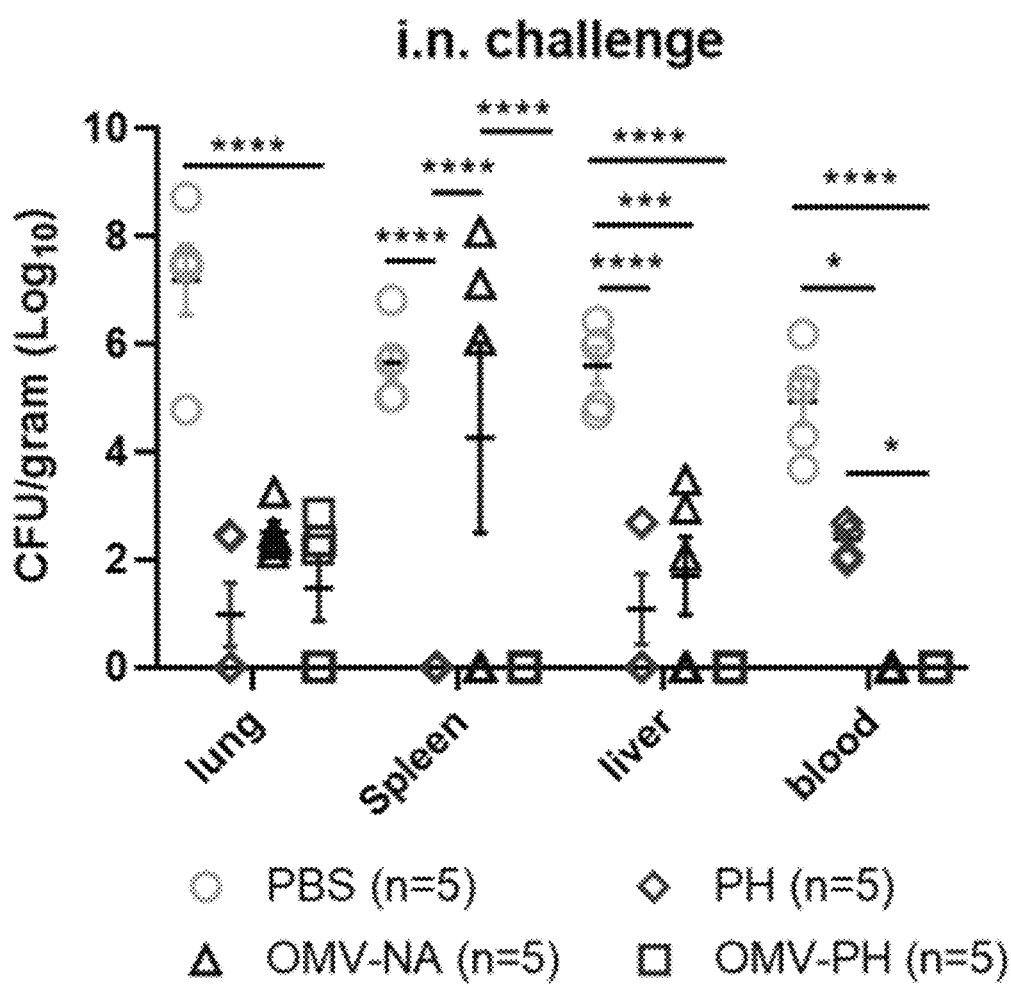
Figure 25E:
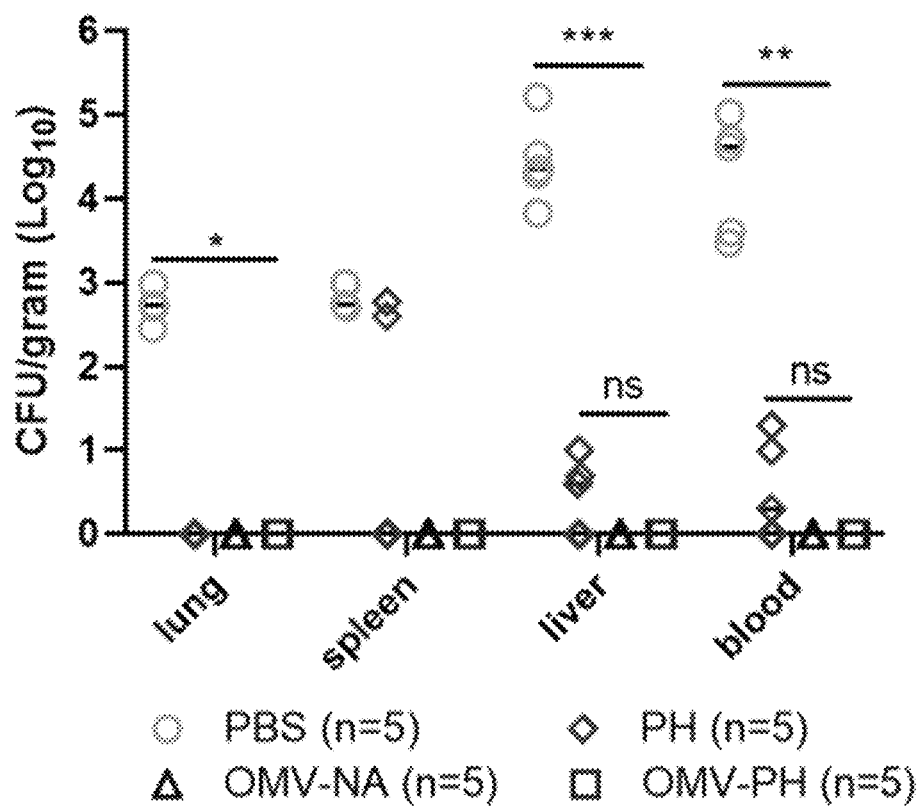

FIGS. 25A through 25E are a series of graphs of Protective efficacy of PA OMVs against *P. aeruginosa* infection and Comparison of bacterial burden in mice after *P. aeruginosa* infection. FIG. 25A—Immunization regimen used for the mouse study; BALB/c mice (n =10) were immunized with PBS/Alhydrogel, 10 μg PH/Alhydrogel, 50 μg OMV-NA or 50 μg OMV-PH by i.m. injection and boosted on 21 days after initial immunization. Mouse weight was monitored and recorded for 6 weeks; FIG. 25B—On 42 days after initial immunization, mice were challenged with 7.4×107 CFUs of wild-type PA103 (10 LD50) by s.c. administration, and animal survival was recorded for 15 days; FIG. 25C—On 42 days after initial immunization, mice were challenged with 6.5×106 CFUs of wild-type PA103 (~30 LD50) by i.n. administration, and animal survival was recorded for 15 days. The experiments were performed twice, and data were combined for analysis. Statistical significance was analyzed by Log-rank (Mantel-Cox) test: ns, no significance; *, p<0.05; , p<0.01, **, p<0.0001. BALB/c mice were immunized with PBS/Alhydrogel, 10 μg PH/Alhydrogel, 50 μg OMV-NA or 50 μg OMV-PH by i.m. administration, and them boosted on day 21 after prime immunization. FIG. 25D—On day 42 after initial immunization, BALB/c mice (n=5) were infected i.n. with a sublethal dose (5×105 CFU) of PA103. On 36-h post challenge, different tissues (lung, liver spleen and blood) were collected from euthanized mice. FIG. 25E—On day 42 after initial immunization, BALB/c mice (n=5) were infected s.c. with a sublethal dose (1.0×107 CFU) of PA103. On 36-h post challenge, different tissues (lung, liver spleen and blood) were collected from euthanized mice. Data were shown as the mean±SEM. The experiments were performed twice, and data were combined for analysis. The statistical significance among the groups were analyzed by two-way multivariant ANOVA with a Tukey post hoc test: ns, no significance; *, p<0.05; , p<0.01; *, p<0.001, ****, p<0.0001.

DETAILED DESCRIPTION OF THE INVENTION

The present invention is directed to the use of an outer membrane vehicle as a new plague vaccine. More specifically, a vaccine platform according to the present invention was developed and tested using a *Yersinia pestis* mutant synthesizing an adjuvant form lipid A (monophosphoryl lipid A, MPLA) that largely increased biogenesis of bacterial outer membrane vesicles (OMVs). To enhance the immunogenicity of the OMVs, an Asd-based balanced-lethal host-vector system was constructed to oversynthesize the LcrV antigen of *Y. pestis*, raise the amounts of LcrV enclosed in OMVs by Type II secretion system, and eliminate harmful factors like plasminogen activator (Pla) and murine toxin from the OMVs. As described herein, vaccination with OMVs containing MPLA and increased amounts of LcrV with diminished toxicity afforded complete protection in mice against subcutaneous challenge and intranasal challenge and was significantly superior to that resulting from vaccination with LcrV/alhydrogel. Self-adjuvanting *Y. pestis* OMVs are therefore a new plague vaccine candidate and that the design of OMVs according to the present invention could serve as a robust approach for vaccine development. For instance, OMVs may be used to induce an immune response to one or more of the pathogens *Y. pestis*, *Y. pseudotuberculosis*, and *Y. enterocolitica*. Advantageously, OMVs can deliver heterologous antigens of other pathogens (such as *B. anthracis*) and may be used to prevent corresponding diseases in animals and humans.

The present invention comprises certain recombinant *Y. pestis* strains. Typically, the bacterium is derived from *Y. pestis* KIM6+. Alternatively, a bacterium of the invention may be a strain listed in Table 1.

Several *Yersinia* species are amenable for use in the present invention. In one embodiment, a recombinant *Yersinia* bacterium of the invention may be a *Y. pestis* bacterium. In another embodiment, a recombinant *Yersinia* bacterium of the invention may be a *Y. pseudotuberculosis* or *Y. enterocolitica* bacterium. The Δasd, ΔyrbE, ΔtolB, Δlpp, ΔnlpI, ΔlacZ::caf1R-caf1M-caf1A-caf1 may be introduced into *Y. pseudotuberculosis* or *Y. enterocolitica* to achieve hyper-vesiculation in bacteria and produce high amounts of OMVs. In addition, the Δyops (cure of pYV plasmid that is similar to pCD1) would be introduced into *Y. pseudotuberculosis* or *Y. enterocolitica* to eliminate potential immune suppression caused by these virulence factors and enhance protective immune response of OMVs against pathogens. In yet another embodiment, a recombinant *Yersinia* bacterium may be a *Y. pestis* or *Y. pseudotuberculosis* bacterium, such as YPS or YPtbS listed in Table 1 and Table 4.

The present invention encompasses a recombinant *Yersinia* bacterium capable of adapted an Asd+ plasmid using a balance-lethal system to over-synthesize protective antigens and generate OMVs containing these antigens. "OMVs" as used herein, Bacterial outer membrane vesicles (OMVs) are vesicles of lipids released from the outer membranes of bacteria. These vesicles may be involved in trafficking bacterial cell signaling biochemicals, which may include DNA, RNA, proteins, endotoxins and allied virulence molecules. OMVs have multiple mechanisms whereby they interact with and regulate innate immune responses to facilitate the onset of bacterial pathogenesis in the host, also OMVs can modulate adaptive immune responses to bacterial pathogens via multiple mechanisms.

A bacterium capable of vesiculation, Vesiculation is a ubiquitous secretion process of Gram-negative bacteria, where outer membrane vesicles (OMVs) are small spherical particles on the order of 30 to 300 nm composed of outer membrane (OM) and lumenal periplasmic content. In one embodiment of the invention, LpxE, a 1-dephosphase from *Francisella novicida*, is able to remove 1-phosphate of lipid A. The bacterium with the lpxE expression can produce monophosphate lipid A (MPLA) and significantly increase bacterial vesiculation, resulting high OMV production. In a preferred embodiment of the invention, such hyper-vesiculation can be achieved by disrupting certain genes ΔyrbE, ΔtolR, Δlpp, and ΔnlpI, that are associated with maintenance of bacterial membrane integrity.

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as *Bacillus anthracis*, may induce an immune response that helps to ameliorate symptoms associated with *B. anthracis* infection or reduce the morbidity and mortality associated with infection with the pathogen. The use of the term "protective" in this invention does not necessarily require that the host is completely protected from the effects of the pathogen.

Some examples of microorganisms useful as a source for antigen are listed below. These may include microorganisms for the control of plague caused by *Yersinia pestis* and other *Yersinia* species such as *Y. pseudotuberculosis* and *Y. enterocolitica*, for the control of gonorrhea caused by *Neisseria gonorrhoea*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Erysipelothrix rhusiopathiae, Neisseria meningitidis, Mycoplasma pneumoniae* and other *Mycoplasma*-species, *Hemophilus influenza, Bordetella pertussis, Mycobacterium tuberculosis, Mycobacterium leprae*, other *Bordetella* species, *Bacillus anthracis, Clostridium difficile, Clostridium perfringens, Staphylococcus aureus, Pseudomonas aeruginosa, Klebsiella pneumoniae, Acinetobacter baumannii, Escherichia coli, Salmonella typhimurium, Salmonella typhi, Salmonella paratyphi, Streptococcus equi, Streptococcus pneumoniae, Brucella abortus, Pasteurella hemolytica* and *P. multocida, Vibrio cholera, Shigella.*, RNA viruses, for example from the classes, influenza viruses Papovavirus, Adenovirus, Herpesvirus, Poxvirus, Parvovirus, Reovirus, Picornavirus, Myxovirus, Paramyxovirus, Flavivirus or Retrovirus (including HIV). Antigens may also be derived from pathogenic fungi, protozoa, parasites and human cancers.

A suitable antigen derived from *Yersinia* and designed to induce an immune response against *Yersinia* may include LcrV, F1, Psn and Ail. LcrV of *Yersinia* is a 37-kDa multifunctional protein that has been shown to act at the level of secretion control by binding the Ysc inner-gate protein LcrG and to modulate the host immune response by altering cytokine production. LcrV also is essential for the unidirectional targeting of Yops to the cytosol of infected eukaryotic cells. A promising subunit vaccine is based on LcrV. Active immunization with purified V antigen or passive immunization with antiserum against V antigen provides protection against plague in mice. CD8+ T-cell immune responses primed to LcrV appear to confer protection against *Y. pestis* in mice. In one embodiment, a live attenuated *Y. pseudotuberculosis* used as a vector to inject the LcrV antigen from *Y. pestis* via T3SS elicits both antibody responses and specific T-cell responses to LcrV of *Y. pestis*, resulting in enhanced protective immunity against plague.

In another embodiment, *Yersinia pestis* uses its F1 capsule to enhance survival and cause virulence to mammalian hosts. *Y. pestis* expresses the caf operon (encoding the F1 capsule) in a temperature-dependent manner. Since F1 is produced in large quantities and secreted into the host tissues, it also serves as a major immune target. Immunity to infection has been correlated with the presence of antibody to the capsular F1 antigen, and immunization with the F1 antigen induces protection against the disease in animal models. A live attenuated *Y. pseudotuberculosis* strain with the caf operon inserted into its chromosome to synthesize F1 in a temperature-dependent manner, can enhance its immunogenicity.

In another embodiment, Pesticin receptor (Psn), an outer membrane protein that is chromosomally in the high pathogenicity island which is present only in highly pathogenic strains of *Yersinia* such as *Y. enterocolitica* 1B, *Y. pseudotuberculosis* and *Y. pestis*. Psn is part of an inorganic iron transport system. Psn as an antigen can stimulate protective immune response against *Y. pestis* infection.

In an exemplary embodiment, a bacterium of the invention may comprise one or more mutations selected from the group comprising Δasd, ΔlacZ::caf1R-caf1M-caf1Δ-caf1, ΔyrbE, ΔtolR, Δlpp, and ΔnlpI.

In another embodiment, a bacterium of the invention harboring a plasmid may comprise multiple antigens from *Yersinia*, such as LcrV, Psn, YopD, and *Bacillus anthracis*, such as PA, LF, EF, and exosporium antigen BxpB.

A recombinant bacterium of the invention may be administered to a host as a vaccine composition. As used herein, a vaccine composition may be a composition designed to elicit an immune response against *Yersinia*. Additionally, a vaccine composition may be a composition designed to elicit an immune response against *Yersinia* and against one or more additional pathogens, such as, *Brucella, B. anthracis, Clostridium, Francisella, Burkholderia, Borrelia, E. coli, Salmonella, Staphylococcus, pseudomonas* or *Klebsiella*. In an exemplary embodiment, the immune response is protective, as described above.

Vaccine compositions of the present invention may be administered to any host capable of mounting an immune response. Such hosts may include all vertebrates, for example, mammals, including domestic animals, agricultural animals, laboratory animals, humans, and rarely in cold-blood animals.

In exemplary embodiments, OMVs from the recombinant bacterium is alive when administered to a host in a vaccine composition of the invention. Suitable vaccine composition formulations and methods of administration are detailed below.

A vaccine composition comprising a recombinant bacterium of the invention may optionally comprise one or more possible additives, such as carriers, preservatives, stabilizers, adjuvants (CpG, polyI:C, c-di-GMP, or Curdlan), and other substances.

The dosages of a vaccine composition of the invention can and will vary depending on the antigen amounts in OMVs, the intended host, and immunization route, as will be appreciated by one of skill in the art. Generally, the dosage need only be sufficient to elicit a protective immune response in a majority of hosts. Routine experimentation may readily establish the required dosage. Typical initial dosages of vaccine for intramuscular injection could be about 50 to 100 µl depending upon the preparation of OMVs. Administering multiple dosages may also be used as needed to provide the desired level of protective immunity.

A vaccine of the invention may be administered via any suitable route, such as by intradermal, intramuscular, subcutaneous or intranasal administration. Additionally, other methods of administering the OMVs, such as, oral administration or other parenteral routes, are possible.

A further aspect of the invention encompasses methods of using an OMV of the invention. For instance, in one embodiment the invention provides a method for modulating a host's immune system. The method comprises administering to the host an effective amount of a composition comprising an OMV of the invention. One of skill in the art will appreciate that an effective amount of a composition is an amount that will generate the desired immune response (e.g., innate, mucosal, humoral or cellular). The monitoring of the response can be by quantitating the titers of antibodies or lymphocytes recognizing the selected antigens or by demonstrating and measuring the level of protective immunity.

In still another embodiment, an OMV of the invention may be used in a method for eliciting an immune response against *Yersinia* and one or more additional pathogens in an individual in need thereof. The method comprises administrating to the host an effective amount of a composition comprising an OMV as described herein.

In a further embodiment, an OMV described herein may be used in a method for ameliorating one or more symptoms of bubonic plague, pneumonic plague, yersiniosis, or anthrax in a host in need thereof. The method comprises administering an effective amount of a composition comprising an OMV as described herein.

EXAMPLE 1

Materials and Methods

Bacterial strains, plasmids, culture conditions, and molecular operations. All bacterial strains and plasmids used in this study are listed in Table 1 and Table 2 below. All bacterial cultures and molecular procedures as in the Supplementary Information below.

TABLE 1

Strains and plasmids used in this study

| Strain or Plasmid | Genotype or relevant characteristics |
|---|---|
| Strains | |
| *E. coli* $\chi$6212 | F-λ- φ80 Δ(lacZYA-argF) endA1 recA1 hsdR17 deoR thi-1 glnV44 gyrA96 relA1 ΔasdA4 |
| *E. coli* $\chi$7213 | thi-1 thr-1 leuB6 fhuA21 lacY1 glnV44 ΔasdA4 recA1 RP4 2-Tc::Mu [λpir]; Km$^r$ |
| *Y. pestis* | |
| KIM6+ (pCD1Ap) | pCD1Ap, pMT1, pPCP1, Pgm$^+$ |
| KIM6+ | pCD1$^-$ pMT1, pPCP1, Pgm$^+$ |
| $\chi$10015 | ΔlpxP:: P$_{lpxL}$lpxL |
| $\chi$10027 | ΔlpxP:: P$_{lpxL}$lpxL ΔlacZ:: P$_{lpp}$lpxE |
| YPS1 | Δasd12 KIM6+ |
| YPS2 | Δasd12 $\chi$10015 |
| YPS3 | Δasd12 $\chi$10027 |
| YPS4 | Δasd12 Δymt50 KIM6+ |
| YPS5 | Δasd12 Δ ymt50 $\chi$10015 |
| YPS6 | Δasd12Δ ymt50 $\chi$10027 |
| YPS7 | Δasd12 Δymt50 KIM6+ pPCP1$^-$ |
| YPS8 | Δasd12 Δymt50 $\chi$10015 pPCP1$^-$ |
| YPS9 | Δasd12 Δymt50 $\chi$10027 pPCP1$^-$ |
| Plasmids | |
| pRE112 | Suicide vector, Cm$^r$, mob$^-$ (RP4)R6K ori, sacB |
| pYA3342 | Asd$^+$; pBR ori |
| pYA3493 | Asd$^+$; β-lactamase signal sequence-based periplasmic secretion, pBR ori |
| pYA4373 | The cat-sacB cassette in sites of PstI and SacI pUC18 |
| pSMV12 | The full-length *Y. pestis* lcrV was cloned into pYA3342 |
| pSMV13 | The full-length *Y. pestis* lcrV was cloned into pYA3620 |
| pSMV25 | The flanking regions of Δasd of *Y. pestis* into XmaI and KpnI sites of pRE112 |
| pSMV26 | The replication origin of pPCP1 cloned into pYA4373 |

TABLE 2

Primers used in this work

| Name | Sequence |
|---|---|
| lcrV-1 | cgggaattcatgattagagcctacgaaca (EcoRI) (SEQ ID NO: 1) |
| lcrV-2 | atgattagagcctacgaaca (SEQ ID NO: 2) |
| lcrV-3 | cggaagctttcatttaccagacgtgtcatctag (HindIII) (SEQ ID NO: 3) |
| Asd-1 | cggggtaccggaaatgggcgatgccgtagtcgcg (KpnI) (SEQ ID NO: 4) |
| Asd-2 | acgctatgcgccgctaaaaaatagtgtttactgc cctgccttggaagg (SEQ ID NO: 5) |
| Asd-3 | cagggcagtaaacactattttttagcggcgcata gcgtgtcatatcgt (SEQ ID NO: 6) |
| Asd-4 | cggcccgggtcgaggagaccgaccagagcctcg (XmaI) (SEQ ID NO: 7) |
| pPCP1-F | attaggatccatcactgacggagcacaacgg (EcoRI) (SEQ ID NO: 8) |
| pPCP1-R | gccgaagctttgttaccgcagcaatacccat (HindIII) (SEQ ID NO: 9) |

OMV isolation. OMVs were isolated from *Y. pestis* strains as previously described with minor modifications. Briefly, the strains were grown at 28° C. in heart Infusion broth (Difco) for 14 h and then incubated at 37° C. for 4 h. The bacterial cultures were supplemented with EDTA (pH 8.0) at 100 mM and kept on ice for 1 h. Then, the bacterial cells were pelleted by centrifugation at 10,000×g at 4° C. for 20 min. The culture supernatant was filtered using a 0.45 μm pore membrane (Millipore) to remove the residual bacterial cells and concentrated with a 100 kDa filter using a Vivaflow 200 system (Sartorius). The OMVs were harvested by ultracentrifugation (120,000×g) for 2 h at 4° C. The vesicle pellet was washed and resuspended in 0.1× sterilized PBS (pH 7.4), and the ultracentrifugation step was repeated. The final vesicle pellet was resuspended in 0.1× sterilized PBS, filtered with a 0.22 μm pore membrane (Millipore) and stored at −80° C. for subsequent experiments. The bacteria and OMV were viewed by Transmission electron microscopy (SI Appendix).

OMV analysis. A Bradford assay was performed as described previously for quantifying the total protein abundance associated with OMVs. The relative lipid contents of the OMVs were determined via a FM4-64 fluorescence dye binding assay measured by a SpectraMax® iD3 Multi-Mode Microplate Reader (Molecular Devices). The values of the protein amounts and lipid contents were normalized according to the total bacterial number (×1011 CFU). The major outer membrane proteins present in the OMV preparations were detected by immunoblotting. Proteomic analysis of OMVs (SI Appendix).

Animal experiments. All animal studies were conducted in accordance with the NIH "Guide for the Care and Use of the laboratory Animals" and approved by the Institutional Animal Care and Use Committee at Albany Medical College (IACUC protocol #18-02004). Six-week-old male and female Swiss Webster mice were purchased from Charles River Laboratories (Wilmington, MA) and acclimated for one week after arrival. The groups of mice were intramuscularly (i.m.) immunized with 400 μg OMVs in 100 μl PBS buffer, 100 μl of a mixture containing 10 μg LcrV/alhydrogel, as a positive control, or 100 μl PBS/alhydrogel, as a negative control. Booster vaccinations were then administered 3 weeks after the initial vaccination. Blood was collected via submandibular veins every 2 weeks to harvest sera for antibody analysis. At 42 days after the initial vaccination, animals were challenged s.c. with *Y. pestis* KIM6+(pCD1Ap) in 100 μl PBS to mimic bubonic plague. For mimicking pneumonic plague, animals were anesthetized with a 1:5 xylazine/ketamine mixture and were challenged i.n. with virulent *Y. pestis* in 40 μl PBS. The LD50 values of *Y. pestis* KIM6+(pCD1Ap) administered by s.c. and i.n. challenge in mice were 10 CFU and 100 CFU, respectively. All infected animals were observed over a 15-day period. For the determination of the bacterial burden, the animals were euthanized with an overdose of sodium pentobarbital. Lungs, livers and spleens were removed at the indicated times and homogenized in ice-cold PBS (pH 7.4) using a bullet blender (Bullet Blender Blue; N.Y., USA) at power 7 for 2 min. Serial dilutions of each organ homogenate were plated on HIB agar, and each count was confirmed with duplicate plates with a minimum of 2 dilutions to determine the titers of bacteria per gram of tissue. The experiments were performed twice, and the data were combined for analysis.

Measurement of antibody responses and cytokines. An enzyme-linked immunosorbent assay (ELISA) was used to assay antibody titers against LcrV, F1 or *Y. pestis* whole cell lysates (YPL) in serum as described in our previous report. A mouse multiplex cytokine assay kit (Bio-Plex) was used to detect the cytokines and chemokines in the BALF and sera collected from the mice according to the manufacturer's instructions.

Analysis of cellular immune responses. Lungs and spleens were obtained aseptically from euthanized animals and dissociated with 70 μm strainers to obtain single cells. The RBC-lysed individual cell populations ($2\times10^6$) were seeded in 12-well cell culture plates and stimulated in vitro for 72 h with 20 μg/ml rLcrV. Four hours before the collection of the cells, the culture media in each well was supplemented with brefeldin-A and a monensin cocktail (1:1 ratio) to block Golgi-mediated cytokine secretion. For the flow cytometric analysis of the T-cell populations and their corresponding cytokines, the induced cells were harvested and resuspended in FACS staining buffer containing CD16/32 antibodies (1:200) for 10 min on ice. The T-cell-specific markers were stained using anti-mouse antibodies as in Table 3 according to the manufacturer's protocol. The samples were acquired on BD flow cytometers (LSRII) and were analyzed using FlowJo v.10.

TABLE 3

Antibodies used in flow cytometry experiments are listed below

| Antibody | Flurophore | Dilution | Company | Clone |
|---|---|---|---|---|
| CD3 | FITC | 1:200 | BioLegend | 17A2 |
| CD4 | PE | 1:200 | BioLegend | GK1.5 |
| CD8 | APC | 1:200 | BioLegend | YTS156.7.7 |
| IFN-γ | PerCP Cy5.5 | 1:200 | BioLegend | XMG1.2 |
| TNF-α | HV510 | 1:200 | BioLegend | MP6-XT22 |
| IL-2 | PECy7 | 1:200 | BioLegend | JES6-5H4 |
| IL17A | APC-Cy7 | 1:200 | BioLegend | TC11-18H10.1 |
| CD45 | FITC | 1:200 | BioLegend | 30-F11 |
| CD11b | HV510 | 1:200 | BioLegend | M1/70 |
| CD11c | APC/Cy7 | 1:200 | BioLegend | N418 |
| Ly6G | PE-Cy7 | 1:200 | BioLegend | 1A8 |

TABLE 3-continued Antibodies used in flow cytometry experiments are listed below

| Antibody | Flurophore | Dilution | Company | Clone |
|---|---|---|---|---|
| Siglec-F | APC | 1:200 | BioLegend | S170072 |
| F4/80 | Pacific Blue | 1:200 | BioLegend | BM8 |

Cells from the BALF and lungs of mice were resuspended in 30 μL of FACS straining solution containing Fc block (CD16/32) at a 1:100 dilution and incubated at room temperature for 15 min to block macrophage Fc receptors. The cell suspensions were then pelleted at 650×g for five min at 4° C. The cells were resuspended and incubated for 30 min at 4° C. with the following fluorescently labeled antibodies (SI Appendix, Table 3) in flow cytometry buffer (1% BSA in PBS) for the staining of cell surface markers. The stained cells were analyzed based on fluorescence staining patterns to identify the alveolar macrophages (Siglec-F+F4/80+CD11bmid/low+CD11chigh+Ly6G−), monocytes (CD11bhigh+CD11clow+Ly-6G−) and neutrophils (CD45+Ly-6G+).

Statistical analysis. Each experiment included a significant number (minimum of 3) of biological replicates, with 2-3 replicates performed in a synchronized fashion to establish reproducibility. The statistical analyses of the data among the groups were performed with one-way ANOVA/univariate or two-way ANOVA with Tukey post hoc tests. The log-rank (Mantel-Cox) test was used for the survival analysis. All data were analyzed using GraphPad PRISM 8.0 software. The data are represented as the mean±standard deviation; ns, no significance, * $p<0.05$,  $p<0.01$, * $p<0.001$, **** $p<0.0001$.

Results

Lipid A 1-dephosphorylation of $Y.$ $pestis$ affects bacterial morphology and increases OMV biogenesis. Previously, $Y.$ $pestis$ KIM6+ isogenic mutants: χ10015 (ΔlpxP::PlpxLlpxL) and χ10027 (ΔlpxP:: PlpxL lpxL ΔlacZ:: Plpp lpxE) (Table 1), produced conventional hexa-acylated lipid A and 1-dephosphorylated hexa-acylated lipid A at 28° C. and 37° C., respectively. χ10027 was more susceptible to polymyxin B than KIM6+ and χ10015, suggesting that lipid A 1-dephosphorylation might influence bacterial membrane stability and morphology. Thus, transmission electron microscopy was employed to visualize all three strains when they were cultured in heart infusion broth (HIB) at 28° C. for 14 h and then incubated at 37° C. for 4 h. The morphologies of KIM6+ and χ10015 were observed as a mixture of coccus and bacillus shapes (FIGS. 1A and B), while the χ10027 strain had been completely altered into cocci (FIG. 1C). The χ10027 strain had a higher percentage of cell wall bulges that were localized to the bacterial surface than the other two strains (FIG. 1).

To determine the effect of lipid A remodeling on $Y.$ $pestis$ OMV biogenesis, it was initially confirmed that OMV biogenesis occurred in each $Y.$ $pestis$ strain cultured at 28° C. for 14 h and then incubated at 37° C. for 4 h. The results showed that KIM6+, ×10015 and χ10027 all produced OMVs, but the sizes of the OMVs from χ10027 were much smaller than those from $Y.$ $pestis$ KIM6+ and χ10015 (FIG. 2A and FIG. 9). Proteomic analysis by mass spectrometry showed that 293 proteins were detectable in OMVs from all three strains (Table 1) and included 12.3% outer membrane proteins, 4.1% periplasmic proteins and 83.6% cytoplasmic proteins (FIG. 2B). OMVs from all three strains contained specific major outer membrane proteins, such as Pla, Ymt, Ail (OmpX), OmpA, F1 and Psn (Table 1). The total protein amounts and lipid contents in OMVs from χ10027 were ~16- and ~150-fold increase in comparison to those from KIM6+ and χ10015, respectively (FIG. 2C). OMVs from KIM6+ and χ10015 showed comparable total protein amounts and lipid contents (FIG. 2C). The amounts of several outer membrane proteins (Psn, OmpA, Pla and F1) were comparable among OMVs isolated from KIM6+, ×10015 and χ10027 (FIG. 2D), but the total protein amounts in OMVs from χ10027 were clearly higher than those from KIM6+ and χ10015 (FIG. 2E). Thus, the results suggested that lipid A 1-dephosphorylation in χ10027 increased OMV biogenesis, while lipid A acylation in χ10015 did not.

A balanced-lethal system for oversynthesizing LcrV antigen in $Y.$ $pestis$. The three above-described strains harboring the virulence plasmid pCD1 are Select agents and must be studied in a Biosafety Level 3 (BSL3) lab. Growing large cultures of these bacteria in BSL3 for OMV isolation is inconvenient and prohibited. A suite of virulence effectors, Yops (YopE, YopJ, YopH, YopM and YopT), that are encoded on the virulence plasmid pCD1 (~70 kb) suppress innate immunity to favor $Y.$ $pestis$ infection upon translocation into host mammalian cells by the T3SS. As a vaccine, OMVs derived from pCD1+ $Y.$ $pestis$ that package Yops may result in potential immune suppression. To avoid these concerns, pCD1-deficient $Y.$ $pestis$ strains were used to produce OMVs in a BSL2 lab. However, OMVs from pCD1-deficient $Y.$ $pestis$ lack the indispensable protective antigen LcrV, which is encoded on the pCD1 plasmid. To overcome this deficiency, a balanced lethal system was constructed to introduce an asd mutation into each $Y.$ $pestis$ strain to generate YPS1, YPS2 and YPS3, respectively (Table 1), which can adopt an Asd+ plasmid for the oversynthesis of LcrV.

Two Asd+ plasmids were constructed: pSMV12 (V), containing the native lcrV gene of $Y.$ $pestis$ and pSMV13 (Bla-V), containing the N-terminal β-lactamase signal sequence (bla ss) fused with $Y.$ $pestis$ lcrV to facilitate LcrV secretion into the periplasm by the Type II secretion system (T2SS) (FIG. 3A and Table 1). Subsequently, both plasmids were introduced individually into the YPS1, YPS2 and YPS3 strains to compare the amounts of LcrV in the bacterial cell fractions, including the whole cell lysate, cytoplasm, periplasm, and OMV fractions. The results showed that all mutant strains harboring the Bla-V plasmid secreted more LcrV into the periplasmic fractions than those harboring the V plasmid, indicating that the β-lactamase secretion signal peptide can facilitate LcrV secretion into the periplasmic space in $Y.$ $pestis$ mutants (FIG. 3B). The amounts of LcrV in the cytoplasm and whole cell lysates of each strain harboring the V or Bla-V plasmid were comparable (FIG. 3B). Moreover, OMVs isolated from all strains harboring Bla-V enclosed higher amounts of LcrV than those harboring the V plasmid (FIG. 3C). Therefore, the pSMV13 (Bla-V) plasmid was chosen for the following studies.

Elimination of potential virulence factors from $Y.$ $pestis$ OMVs. $Y.$ $pestis$ harbors two additional plasmids, pPCP1 (9.6 kb), encoding the plasminogen activator (Pla), and pMT1 (102 kb), encoding murine toxin (Ymt) and the protective antigen F1. Pla is necessary for $Y.$ $pestis$ dissemination and the inhibition of immune cell recruitment and induces fibrinolysis. Murine toxin, which is encoded by ymt, is highly toxic in mice and rats but is less toxic in larger animals. Pla and Ymt are clearly present in $Y.$ $pestis$ OMVs (FIG. 2D and Table 1). To eliminate the potential adverse effects of Pla and Ymt on hosts, the pPCP1 plasmid was cured and the ymt gene deleted from strains YPS1, YPS2 and YPS3 individually by using sequential steps to generate mutant strains designated YPS7, YPS8 and YPS9, respectively (Table 1, FIG. 10). Then, the Bla-V plasmid was individually introduced into the YPS7, YPS8 and YPS9 strains and compared the OMV production of these mutant strains. The results showed that YPS9(Bla-V) with 1-phosphorylated lipid A still generated higher numbers of OMVs (FIG. 3D) and enclosed substantially higher levels of LcrV and Psn antigens than YPS7(Bla-V) or YPS8(Bla-V). The amounts of F1 antigen in OMVs derived from each strain were comparable (FIG. 3E). Additionally, the total protein amounts in OMVs from YPS9(Bla-V) were clearly higher than those in OMVs from the other two strains (FIG. 3F).

The stimulation and cytotoxicity of OMVs from YPS7 (Bla-V), YPS8(Bla-V) or YPS9(Bla-V) cultured with different cell lines was compared in vitro and found that OMVs from YPS9(Bla-V) could activate the TLR4-mediated NF-κB signaling pathway but showed less stimulatory activity than OMVs from the other two strains (FIG. 11). OMVs from YPS7(Bla-V) or YPS8(Bla-V) at a concentration of 25 μg/ml generated significantly higher amounts of TNF-α and cytotoxicity in RAW 264.7 cells than OMVs from YPS9 (Bla-V) at the same concentration, but a low concentration (10 μg/ml) of all three types of OMVs produce decreased amounts of TNF-α without any difference and showed diminished cytotoxicity in cells (FIG. 11B). Given the above results, the YPS9(Bla-V) strain was used to produce the greatest amounts of OMVs decorated with MPLA, presenting low toxicity and enclosing high amounts of protective antigens for vaccine evaluation.

Immunization with self-adjuvanting OMVs afforded complete protection against *Y. pestis* challenge. Groups of mice (n=10) were intramuscularly immunized with OMVs purified from YPS9(Bla-V), LcrV/alhydrogel or PBS/alhydrogel (sham) and boosted at 21 days after the prime immunization (FIG. 4A). None of the vaccinations affected body weight increases in mice (FIG. 12A) or caused observable health issues. The measurement of serum antibody responses showed that the total anti-LcrV IgG titers were primed at higher levels in LcrV-immunized mice than in OMV-immunized mice at week 2 post vaccination but were boosted to the same levels in both immunized groups by week 4 post vaccination (FIG. 4B). The anti-YPL IgG titers (*Y. pestis* whole cell lysate) in OMV-immunized animals at weeks 2 and 4 post vaccination were substantially higher than those in LcrV-immunized animals (FIG. 4B), also high anti-F1 IgG titers were primed at week 2 post vaccination and boosted at week 4 post vaccination in the OMV-immunized mice (FIG. 4B). Additionally, significant anti-LcrV, YPL and F1 IgM titers were primed in OMV-immunized mice at week 2 post vaccination, which were substantially increased at week 4 post vaccination after the booster. The LcrV and YPL IgM titers in the LcrV-immunized mice were not substantially different, but they were significantly lower than those in the OMV-immunized mice at weeks 2 and 4 post vaccination (FIG. 12B).

On day 42 after the initial vaccination, the mice were challenged by the subcutaneous (s.c.) or intranasal (i.n.) route to mimic bubonic or pneumonic plague, respectively. All OMV-immunized mice survived s.c. challenge with 8×105 CFU ($8\times10^4$ LD50) of *Y. pestis* KIM6+(pCD1Ap), while 80% of the LcrV-immunized mice survived the same challenge (FIG. 4C). The OMV vaccination afforded 100% and 50% protection in mice against i.n. challenge with a median dose of 5×103 (50 LD50) and a high dose of 5×104 (500 LD50) of *Y. pestis* KIM6+(pCD1Ap), respectively. The LcrV vaccination conferred decreased protection (FIG. 4D), and none of the sham mice survived both challenges (FIGS. 4C and D).

Vaccination with self-adjuvanting OMVs elicited Th1/Th2-balanced immune responses. In mice, IgG1 is associated with a Th2-like response, while a Th1 response is associated with the production of IgG2a, IgG2b, and IgG3 antibodies. Therefore, the IgG subtypes produced in response to each antigen were analyzed to distinguish between Th1/Th2 immune responses in immunized mice. The anti-LcrV IgG1 titers were high and showed similar profiles as the anti-LcrV total IgG titers in both LcrV- and OMV-immunized mice (FIG. 4B and FIG. 5A). In FIG. 5A, it is shown that both LcrV- and OMV-immunized animals were primed with moderate titers of anti-LcrV IgG2a and IgG2b and did not show a substantial difference at week 2 post vaccination. After the booster, the titers of anti-LcrV IgG2a and IgG2b were slightly increased in the LcrV-immunized groups at week 4 post-initial vaccination but rapidly increased in the OMV-immunized groups, and they were significantly higher than those in the LcrV-immunized groups. At week 4 post vaccination, the ratios of anti-LcrV IgG1/IgG2a and IgG1/IgG2b were 1.5 and 1.4 in LcrV-immunized mice, respectively, while the ratios of anti-LcrV IgG1/IgG2a and IgG1/IgG2b were 1.0 and 0.99 in OMV-immunized mice, respectively (FIG. 5A). As shown in FIG. 5B, the OMV-immunized mice were primed with high titers of anti-YPL IgG1, IgG2a and IgG2b at week 2 post vaccination, which were substantially increased at week 4 post vaccination after the booster. However, the titers of anti-YPL IgG1, IgG2a and IgG2b remained steady in the LcrV-immunized groups at weeks 2 and 4 post vaccination. At week 4 post vaccination, the ratios of anti-YPL IgG1/IgG2a and IgG1/IgG2b were 1.6 and 1.4 in the LcrV-immunized groups, respectively, whereas the ratios of anti-YPL IgG1/IgG2a and IgG1/IgG2b were 1.0 and 1.1 in the OMV-immunized groups, respectively (FIG. 5B). Additionally, the OMV-immunized mice were primed with high titers of anti-F1 IgG1, IgG2a and IgG2b at week 2 post vaccination, which were substantially increased at week 4 post vaccination after the booster (FIG. 5C). The ratios of anti-F1 IgG1/IgG2a and IgG1/IgG2b were 1.2 and 1.0 at week 4 post-initial vaccination, respectively. Collectively, the OMV-immunized mice generated more broad antibody responses against multiple antigens and more balanced Th1/Th2 responses than the LcrV-immunized mice.

Vaccination with self-adjuvanting OMVs induced potent cellular immune responses. After 72 h of in vitro induction with LcrV or PBS, lung lymphocytes from OMV-immunized mice showed substantial increases in both the CD4 and CD8 T cell populations (FIGS. 6A&B). Lung CD4+ T-cells from OMV-immunized mice displayed significantly higher production of IFN-γ, IL-2 and TNF-α than those from LcrV-immunized and sham mice (FIG. 6A). Lung CD8+ T-cells from OMV-immunized mice stimulated with LcrV protein showed higher production of TNF-α than those from LcrV-immunized and sham mice, but did not show increased production of IFN-γ, IL-2 and IL-17 in comparison to that in sham- or LcrV-immunized animals (FIG. 6B). Both lung CD4+ and CD8+ T-cells from LcrV-immunized mice demonstrated higher production of IL-4 than those from OMV-immunized mice after in vitro stimulation with LcrV (FIGS. 6A & B).

Similarly, splenocytes from both OMV- and LcrV-immunized mice also showed increased production of CD4+ and CD8+ T cells in comparison to those from sham mice after in vitro stimulation with LcrV (FIG. 13). Spleen CD4+

T-cells from OMV-immunized mice demonstrated significantly higher production of IL-2 and IL-17 than those from LcrV-immunized and sham mice. Significantly higher production of IFN-γ and IL-4 were observed in spleen CD4+ T-cells from both OMV- and LcrV-immunized mice in comparison to those from sham mice. (FIG. 13). Spleen CD8+ T-cells from OMV-immunized mice showed higher production of TNF-α than those from LcrV-immunized and sham mice (SI Appendix, FIG. S5B). However, both spleen CD4+ and CD8+ T-cells from LcrV-immunized mice also produced higher levels of IL-4 than those from OMV-immunized mice (FIG. 13). These results suggested that OMV vaccination elicited more potent LcrV-specific cellular immune responses in mice than LcrV vaccination.

In vivo responses after $Y.$ pestis pulmonary challenge. Furthermore, bacterial burdens were specifically monitored in different tissues, variations of different cells in lung and bronchoalveolar lavage fluid (BALF), and cytokine production in BALF on day 2 after pulmonary $Y.$ pestis challenge to determine the correlation between animal survival and host responses. On day 2 postinfection, the sham mice were found to have strikingly increased $Y.$ pestis titers (mean 7.8 log 10 CFU/g tissue) in lung and moderate bacterial titers in liver (mean 3.8 log 10 CFU/g tissue) and spleen (mean 2.0 log 10 CFU/g tissue). In the LcrV-immunized mice, the bacterial titers reached moderate levels (mean 3.6 log 10 CFU/g tissue) in the lungs, but the bacteria could not disseminate into the liver and spleen (FIG. 7A). No $Y.$ pestis titers were observed in the lungs, livers and spleens of OMV-immunized mice (FIG. 7A).

Upon the comparison of immunized mice with or without infection, significant increases in CD4+CD44+ cells were observed in the lungs of LcrV- or OMV-immunized mice after infection (FIG. 7B). Moreover, the number of CD4$^+$CD44$^+$ cells in the lungs of OMV-immunized mice was significantly higher than that in the lungs of sham or LcrV-immunized mice at day 2 post infection (FIG. 7B). There were no substantial differences in CD4+CD44+ cell numbers in sham mice pre infection and post infection (FIG. 7B). Slight decreases in CD8+CD44+ cells but no significant differences were observed in the lungs of sham, LcrV- and OMV-immunized mice pre infection and post infection (FIG. 14). In the BALF, the numbers of alveolar macrophages (AMφ) in sham mice with or without $Y.$ pestis infection were comparable (FIG. 7C), but the numbers of neutrophils were dramatically elevated in sham mice after $Y.$ pestis infection in comparison to those in noninfected mice (FIG. 7D). In contrast, the numbers of AMφ were significantly increased in LcrV- or OMV-immunized mice on day 2 post infection in comparison to those in immunized mice without infection (FIG. 7C), while the numbers of neutrophils did not show substantial differences in LcrV- or OMV-immunized mice pre infection and post infection (FIG. 7D). In lung tissues, no obvious alterations in AMφ numbers were observed in mice with or without $Y.$ pestis infection (FIG. 7E), but the numbers of lung neutrophils were dramatically increased in sham mice compared with LcrV- or OMV-immunized mice on day 2 post infection (FIG. 7F). Slight increases in monocytes but no substantial differences were observed in sham, LcrV or OMV-immunized mice pre infection and post infection (FIGS. 14B & 14C). Additionally, dramatically increased levels of proinflammatory cytokines (IL-1α IL-1β, IL-6, IL-17 and IFN-γ) and chemokines (G-CSF KC, and MIP-1α) associated with the recruitment of neutrophils were secreted into the BALF of sham mice on day 2 post infection in comparison to the levels in sham mice without infection. However, there were no differences in these cytokines and chemokines in the BALF from LcrV- or OMV-immunized mice between pre infection and post infection (FIG. 8). These data showed that LcrV or OMV vaccination rapidly activated CD4+ T memory cells, increased the number of AMφ in BALF and reduced neutrophil recruitment after $Y.$ pestis pulmonary infection, which effectively controlled $Y.$ pestis dissemination and cytokine storms that typically lead to the rapid death of mice.

Discussion

Generally, the removal of phosphate groups decreases the overall negative charge of a bacterium, thus reducing the electrostatic interactions of the phosphates in lipid A with cationic antimicrobial peptides and decreasing the susceptibility to polymyxin B, which is a cationic antimicrobial peptide that binds negatively charged phosphate groups in lipid A units in LPS on the bacterial membrane and inserts its hydrophobic tail into the outer membranes of bacteria, causing membrane damage and bacteria killing. The removal of 1-phosphate from the conventional biphosphorylated lipid A in $E.$ coli and Salmonella decreased their susceptibility to polymyxin B, but the opposite was observed in $Y.$ pestis. The possible reasons for this are as follows: 1) $Y.$ pestis masked the phosphate groups with 4-amino-4-deoxy-1-arabinose (1-Ara4N) to reduce the negative charge at its surface using different regulatory strategies that those used by Salmonella; 2) $Y.$ pestis naturally lacks O-antigen because bacteria with the full O-antigen are more resistant to polymyxin B than O-antigen isogenic mutants; 3) lipid A 1-dephosphorylation in $Y.$ pestis may cause cation displacement in the outer membrane (OM), resulting in a reduction in OM integrity and an increase in OM permeability and thereby changing $Y.$ pestis morphology by increasing the OM curvature (FIG. 1C) and OMV formation (FIG. 2C). The replacement of acylated fatty acid chains (palmitoleate, C16) in $Y.$ pestis KIM6+ with laurate (C12) in the χ10015 (ΔlpxP::$P_{lpxL}$ lpxL) strain did not substantially affect bacterial morphology or OMV production (FIGS. 1 and 2C). However, lipid A alteration via the constitutive expression pagL in $S.$ Typhimurium to remove the β-hydroxymyristoyl group at position 3 in lipid A significantly increased vesiculation and induced OMV production. Thus, alterations in lipid A acylation at different positions in Kdo2 lipid IVA may produce different outcomes during bacterial membrane vesiculation. Further investigations are needed to dissect this process.

Vaccination with OMVs derived from a wild-type $Y.$ pestis strain containing very low amounts of LcrV provided very limited protection against plague (unpublished data). An Asd+-based balanced lethal Salmonella system was adopted with the $Y.$ pestis system that was successful in overcoming this limitation by oversynthesizing LcrV (FIG. 3B). The data demonstrated that the localization of the LcrV protein that was secreted into the $Y.$ pestis periplasm by the T2SS led to the enclosure of high amounts of LcrV by OMVs (FIG. 3C); Thus, this strategy would be applicable to the delivery of antigens from other pathogens.

In addition to the production of high titers of IgGs against LcrV, YPL and F1 antigen (FIG. 4B) that can synergize with cellular immune responses to defend against $Y.$ pestis infection, vaccination with OMVs also elicited significantly increased titers of IgM against LcrV, YPL and F1 in mice than vaccination with LcrV (SI Appendix, FIG. 12B). IgM has been demonstrated to play a protective role in extracellular and intracellular bacterial infections and to facilitate the removal of foreign pathogens due to its efficient agglutination. In mice, B-1a cells spontaneously maintain steadystate levels of natural IgM, while B-1b cells secrete IgM in response to pathogen encounters or heterologous antigens. Recently, it was shown that the capsular F1 antigen of *Y. pestis* was recognized by B1b cells and generated high levels of anti-F1 IgM, which played a significant role in responses to plague challenge. It is speculated that high levels of IgM induced by vaccination with self-adjuvanting OMVs containing capsular F1, LcrV or other antigens from *Y. pestis* may produce better protection against plague than vaccination with LcrV antigen. Further investigations are needed to fully understand the role of IgM secreted from B1b cells in preventing *Y. pestis* infection.

Previous studies showed that recombinant, bacterially derived OMVs induced a more balanced Th1/Th2 response. Both LcrV and OMV vaccination elicited the production of significant levels of IgG against LcrV and YPL in mice (FIG. 4B), but OMV vaccination induced a more balanced Th1/Th2 immune response than LcrV vaccination (FIGS. 5A and B). Consistent with the antibody responses, both lung and spleen CD4+ T-cells from OMV-immunized mice produced higher levels of Th1 cytokines (IFN-γ, IL-2, IL-17 or TNF-α) and significantly lower amounts of Th2 cytokines (IL-4) than those from LcrV-immunized mice after LcrV stimulation in vitro (FIG. 6A and FIG. 12A). Studies have shown that protection against plague is known to require humoral immunity and cell-mediated immunity induced by IFN-γ and TNF-α. IL-17 also contributes to cell-mediated defense against pulmonary *Y. pestis* infection. The induction of potent Th1 and Th17 cell responses by self-adjuvanting OMV vaccination might be one of the primary reasons it offers better protection against lethal infection by *Y. pestis* than LcrV vaccination (FIGS. 4C&D). The detailed mechanisms underlying protective immunity need to be studied further.

The disease progression of primary pneumonic plague in several animal models is biphasic and consists of a preinflammatory and a pro-inflammatory phase. The early 'pre-inflammatory' phase of the disease (initial 36 h post infection) is characterized by rapid *Y. pestis* replication in the lungs of mice but an absence of measurable host immune responses or obvious disease symptoms. In contrast, the proinflammatory phase (48 h post infection) is characterized by continuous increases in bacterial titers and dramatic increases in the levels of cytokines (IL-1α IL-1β, IL-6, IFN-γ and IL-17) and chemokines (KC, G-CSF, MIP-1α) accompanied by massive neutrophil influx in the lungs and alveolar spaces, resulting in acute lethal pneumonia. The data showed that the responses in the sham group mice on day 2 post infection (FIG. 7) were consistent with previous observations. In contrast, both LcrV and OMV vaccination subverted the progression of *Y. pestis* pulmonary infection in mice, resulting in low or absent bacterial titers in the lungs, spleens and livers (FIG. 7A) and significant increases in CD4+CD44+ memory T cells (FIG. 7B) and AMq in BALF (FIG. 7C), which was not observed in sham mice. The results suggested that the presence of memory CD4+ T cells, along with high titers of specific anti-*Y. pestis* antibodies, might activate AMΦ and enhance their phagocytosis, leading to the rapid elimination of inhaled *Y. pestis*.

In *Y. pestis* pulmonary infection, the massive recruitment of mature and immature neutrophils in response to an increasing bacterial burden leads to highly necrotic, lethal pneumonia. This phenomenon occurred in sham mice on day 2 post infection and was characterized by dramatic increases in neutrophils in the BALF and lung (FIGS. 7D&F) and high amounts of proinflammatory cytokines and chemokines in the BALF and sera (FIGS. 8 and 13). However, the recruitment of neutrophils (FIGS. 7D and F) and the production of proinflammatory cytokines and chemokines (FIGS. 8 and 13) in both OMV- and LcrV-immunized mice were well controlled. Increasingly, evidence has shown that "trained immunity" mediated by innate immune cells primed by encounters with certain pathogens or molecular patterns associated with pathogens (PAMPs) could achieve broad protection. It is speculated that OMV or LcrV vaccination might endow macrophages, neutrophils and other innate cells in the lung with high expression rates of activation markers that allow these cells to form an organized and protective inflammatory response to *Y. pestis* infection. Therefore, it is worthwhile to further investigate whether the potent "trained immunity" induced by self-adjuvanting OMVs derived from *Y. pestis* engineered with an array of PAMPs plays an important protective role against *Y. pestis* infection.

The studies showed that protective immunity elicited by self-adjuvanting OMVs derived from engineered *Y. pestis* was greater than that elicited by LcrV/alhydrogel, suggesting that OMVs could be utilized as antigen carriers for delivering antigens and adjuvants as part of a promising and effective next generation plague vaccine.

Supplemental Information

Bacterial Culture Conditions

All *E. coli* strains were grown routinely at 37° C. in LB broth or LB Agar (Difco). *E. coli* strain, χ7213, was used to construct suicide vectors and conjugate with *Y. pestis* for generating mutations. *Y. pestis* grown in heart infusion broth (HIB) and Tryptose blood agar (TBA) plates was described previously. Strain construction was performed using *Y. pestis* KIM6+ derivatives that lack the 70 kb pCD1 plasmid and exempt from Select Agent status and can be handled at BSL-2. Ampicillin at 100 μg/ml or chloramphenicol at 25 μg/ml was supplemented to media, when necessary. Fully virulent strain *Y. pestis* KIM6+ (pCD1Ap) was used for animal challenge under BSL-3/ABSL3 containment.

Molecular and Genetic Procedures

Plasmids and primers used in this study were listed in supplemental Table 1 and Table 2, respectively. The lcrV gene was amplified by a lcrV-1/lcrV-3 primer set from genome of *Y. pestis* KIM6+(pCD1Ap) and cloned into NcoI and HindIII sites of pYA3342 to generate pSMV12. The lcrV gene was amplified by a lcrV-2/lcrV-3 primer set from genome of *Y. pestis* KIM6+(pCD1Ap) and cloned into EcoRI and HindIII sites of pYA3493 to generate pSMV13. The Δasd flanking region of *Y. pestis* KIM6+ was assembled by overlapping PCR using Asd-1/Asd-2 and Asd-3/Asd-4 primer sets and cloned into a suicide vector pRE112 to generate pSMV25. To cure pPCP1 plasmid, the replication origin was amplified by the pPCP1-F/pPCP1-R primer set and cloned into pYA4373 to generate pSMV26. All the plasmids were confirmed by PCR screening and DNA sequencing. The procedures for the sacB-based sucrose counter-selectable suicide vectors used to construct unmarked deletion and/or insertion mutations in *Y. pestis* were described in a previous report. Successful gene mutations were confirmed by PCR screening.

Bacterial Subcellular Fractionation Analysis

*Y. pestis* strains were grown in HIB broth at 28° C. for 14 h and then incubated at 37° C. for 4 h The bacterial cells were collected by centrifugation (10,000×g) for 10 minutes. Periplasmic and cytoplasmic fractions were prepared by a lysozyme-osmotic shock method. Equal volumes of periplasmic, cytoplasmic, and supernatant fractions and total lysate samples was analyzed using Western blotting.

Transmission electron microscopy (TEM). Bacterial cultures were absorbed onto freshly glow-discharged Formvar/carbon-coated copper grids for 10 min. The grids were washed in ddH2O and stained with 1% aqueous uranyl acetate (Ted Pella, Inc., CA) for 1 min. The excess liquid was gently wicked off, and the grids were allowed to air dry. The samples were viewed with a JEOL 1200EX transmission electron microscope (JEOL Peabody, MA) equipped with an AMT 8-megapixel digital camera (Advanced Microscopy Techniques, Woburn, MA). The OMVs were analyzed by TEM as described in previous reports.

Stimulation and Cytotoxicity Assay in Cell Lines

To determine stimulatory activity of OMVs via TLR4, HEK-Blue™ hTLR4 and HEK-Blue™ Null1-v cells (InvivoGen, CA, USA) were maintained at 37° C. with 5% CO2 in DMEM (Gibco BRL, Grand Island, NY, USA) containing 10% FBS supplemented with 100 μg/ml penicillin, 100 μg/ml streptomycin and 100 μg/ml Normocin. Cells were seeded at a density of 5×104 cells per well in 96-well tissue culture plates (Costar, Washington, DC) and were stimulated with 20 μl OMVs isolated from different strains (final concentration 10 μg/ml or 25 μg/ml) for 8 h. HEK-Blue™ Null1-v cell and PBS as negative controls. Relative NF-κB activity was determined by measuring the embryonic alkaline phosphatase (SEAP) activity that accumulated the culture media according to the manufacturer's instructions.

Murine macrophage RAW264.7 cells were maintained at 37° C. with 5% CO2 in DMEM (Gibco BRL, Grand Island, NY, USA) containing 10% FBS supplemented with 100 μg/ml penicillin and streptomycin. Cells were seeded at a density of 5×104 cells per well in 96-well tissue culture plates (Costar, Washington, DC) and cultured for 12h, and then were stimulated with OMVs isolated from different strains (final concentration 10 μg/ml or 25 μg/ml). 20 ng/ml of LPS as a positive control. After 24 h, the supernatants from each well were collected for measuring TNF-α secretion using Mouse TNF alpha ELISA Ready-SET-Go! kit (Thermo scientific) and lactate dehydrogenase (LDH) release using a Multitox-Fluor Multiplex Cytotoxicity Assay kit (Promega, Madison, USA) following the manufacturer's instructions. Statistical significance among groups were analyzed by two-way multivariant ANOVA with a Tukey post hoc test. ns, no significance, *, $P<0.05$; , $P<0.01$; *, $P<0.001$, ****, $P<0.0001$.

EXAMPLE 2

Construction of an Asd+ Plasmid Containing Genes Encoding Protective Antigens from Both Y. pestis and B. anthracis.

Delivering antigens by T2SS into the periplasm space of bacteria could increase the antigens in lumen of OMVs, significantly increasing antibody responses and protective immunity. As mentioned above, protective antigen (PA) of anthrax toxin encoded by pagA is the primary component of human anthrax vaccine. So, the same strategy was applied to construct an Asd+ plasmid to synthesize and secrete PA of B. anthracis in the heterologous Yptb strain. The pagA gene fragment removing the N-terminal signal sequence is codon-optimized to favor for expression in Y. pseudotuberculosis. In addition, the codon-optimized pagA gene ($PA_{op}$ gene) has mutations to eliminate proteolytic cleavage sites, such as a furin site by replacing $RKKR^{167}$ with $SNKE^{167}$ and a chymotrypsin site via deletion of $FF^{314}$ and a substitution at position 308 (E308D), which enhances the stability of the PA protein in the mammalian host. So, the $PA_{op}$ gene fused with N-terminal β-lactamase signal sequence (bla ss) is cloned downstream from $P_{lpp}$ promoter of an Asd+ plasmid (pSMV59) to facilitate PA secretion into the bacterial periplasmic space, resulting in high amounts of PA encased in OMVs. So, pSMV59 was introduced into YPS9 to determine PA synthesis in whole cell lysate and OMV fractions, result showed that OMVs from YPS9 (pSMV59) encased high amounts of PA antigen (FIG. 15A).

Based on results shown in FIGS. 3 and 11A, it is possible to construct a new Asd+ plasmid (designated as pSMV60) (FIG. 15B) containing both lcrV of Y. pestis and codon-optimized pagA of B. anthracis and introduce pSMV60 into YPS9 to allow the mutant strain to synthesize both LcrV and PA. Results showed that OMVs isolated from YPS9 (pSMV60) contained huge amounts of PA and LcrV antigen (FIG. 15B).

An Y. pseudotuberculosis (Yptb) mutant strain was constructed which robustly produces self-adjuvating and highly immunogenic OMVs to deliver protective antigens from different pathogens. Yptb PB1+ (serotype O:1b) is the closest ancestor of Y. pestis, But Yptb is much less virulent than Y. pestis, can be operated in BSL2 lab, and typically causes enteric diseases in humans and animals. With the exception of two additional plasmids carried by Y. pestis (pPCP1 and pMT1), the two species share >95% genetic identity and a

TABLE 4

Y. psedotuberculosis strains and plasmids used in this study

| Strain or Plasmid | Genotype or relevant characteristics |
|---|---|
| | Y. pseudotuberculosis |
| Yptb PB1+ | Y. pseudotuberculosis PB1+, serotype O:1B |
| YptbS32 | Cure pYV plasmid |
| YptbS40 | ΔhmsHFRS425 pYV− |
| YptbS41 | ΔhmsHFRS425 pYV− ΔlacZ044::cafR-cafM-cafA-caf1 |
| YptbS42 | ΔhmsHFRS425pYV−ΔlacI :: $P_{lpp}$ lpxE ΔlacZ::caf1R-caf1M-caf1A-caf1 |
| YptbS43 | Δasd ΔhmsHFRS425ΔlacI :: $P_{lpp}$ lpxE pYV− ΔlacZ::caf1R-caf1M-caf1A-caf1 |
| YptbS44 | Δasd ΔtolR ΔhmsHFRS425ΔlacI :: $P_{lpp}$ lpxE pYV− ΔlacZ::caf1R-caf1M-caf1A-caf1 |
| Plasmids | |
| pRE112 | Suicide vector, $Cm^r$, $mob^-$ (RP4)R6K ori, sacB |
| pSMV13 | The full-length lcrV was cloned into pYA3620 |
| pSMV59 | $P_{lpp}$- bla ss- $pagA_{op}$ in the pYA3342 |
| pSMV60 | $P_{lpp}$- bla ss- $pagA_{op}$ into pSMV13 | common virulence plasmid (pCD1/pYV) with a conserved colinear backbone. Yptb grows much faster than *Y. pestis* at both 28° C. and 37° C. in HIB media, produces higher amounts of OMVs than *Y. pestis* in the same culture volumes and is much easier to be genetically manipulated than *Y. pestis*. Therefore, the Yptb PB1+ strain as an alternative to generate high immunogenic and minimal reactogenic OMVs should be an ideal option to achieve similar OMVs but greatly reduce labor-intensive process. To do so, an Yptb mutant strain was constructed, YPtbS41 (Table 4) that produces MPLA, an adjuvant form Lipid A, cures the virulence plasmid pYV to remove all possible immuno-modulation factors (Yops) and incorporates the caf1 operon into chromosome to synthesis F1 antigen as an initial strain.
Increasing Production of OMVs.

It is well established that defects in a range of proteins involved in maintaining the structural integrity of the membrane result in increased vesiculation. In *E. coli*, the five proteins of the Tol-Pal system is comprised of three inner membrane proteins (TolA, TolQ, and TolR) and a periplasmic protein (TolB), which interact with an outer membrane protein, peptidoglycan-associated lipoprotein (Pal). Disruption of tolR in *E. coli* and *Salmonella* did not significantly compromise the cell envelope and growth, but resulted in high levels of OMVs formation. Also individual disruption of vacJ and yrbE resulted in excessive OMV production in *Haemophilus influenza*, *Vibrio cholera* or *E. coli*. NlpI, a lipoprotein, participates in the balance of peptidoglycan breakdown and synthesis. *E. coli* ΔnlpI exhibits hypervesiculation and an increased OMVs production compared to the otherwise isogenic parental strain, without evident leakage of cytoplasmic proteins. *Actinobacillus pleuropneumoniae* ΔnlpI has similar occurrences. Homologous genes of tolR, vacJ, yrbE and nlpI in *Y. pseudotuberculosis* strain are YPTS_1234 (83% amino acid identity), YPTS_2737 (75% amino acid identity), YPTS_3704 (83% amino acid identity), and YPTS_0515 (87% amino acid identity) respectively. Therefore, tolR, vacJ, yrbE and nlpI were deleted from wild-type Yptb PB1+ individually and compare OMVs production of each mutant strain with Yptb PB1+. Results have shown that only the tolR mutant largely increases OMVs production, while the vacJ, yrbE or nlpI mutant dose not heighten OMVs production in comparison with Yptb PB1+ (FIG. 16). Taken together, the tolR mutation was introduced on top of YPtbS44 (Table 4) to increase OMVs production.

Construction of a Recombinant Yptb Strain Heterologously Expressing the Gene Cluster for β-(1-3)-Glucan Synthesis.

More and more evidences indicate that plague vaccines aiming to induce mixed Th1 and Th17 cellular responses would provide more powerful and comprehensive protection. Curdlan acts as an adjuvant for the activation of Th1 and, in particular, Th17 immunity. Curdlan is a high-molecular-weight water insoluble β-(1-3)-D-glucan (glucose homo-polymer) without any substituents that has been approved as a food additive by the U. S. FDA. Curdlan is produced by an *Agrobacterium* sp. (formerly known as *Rhizobium lupini*) and some other bacteria. Four genes are involved in curdlan biosynthesis (crdA, crdS, crdC and crdR). The curdlan synthase (CrdS), is the key enzyme of curdlan biosynthesis. The UDP-glucose is also a critical block for the curdlan synthesis. So far, there are no reports about exact UDP-glucose synthesis in Yptb. Protein blast shows that Yptb has a galUF operon governing UDP-glucose synthesis. Therefore, introducing the curdlan synthesis operon (crdASCR) into a certain site of chromosome in YPtbS39 (Table 4) that would synthesize β-(1-3)-glucan will be explored. In addition, studies have shown that production of curdlan is activated by the second messenger c-di-GMP binding to glucan synthase, CrdS. So, the mutant strain combining elevation of c-di-GMP and curdlan synthesis operon would increase curdlan synthesis.

EXAMPLE 3

The PcrV forms a ring structure at the tip of the needle of Type three secretion system (T3SS) in PA and is essential for translocation of the effectors and bacterial pathogenicity. PcrV is a conserved protein among different serotypes of PA isolates and a promising antigen candidate. Immunization with recombinant PcrV or adaptive transfer of anti-PcrV antibodies offered significant protection against lethal PA infections. In addition, iron is an indispensable nutrient for replication of almost all bacteria. Several iron acquisition systems are used by PA to obtain iron from mammalian hosts during infection and play an important role in bacterial virulence. The hitA (PA4687), hitB (PA4688), and others in PA are involved in iron transportation and associated with bacterial virulence. A study showed immunization with ferric iron-binding periplasmic protein HitA afforded protection against PA infection in mice. Therefore, immunization with OMVs delivering heterologous PcrV and HitA antigens as a bivalent vaccine might potentiate protective immunity against PA infection.

Here, an Asd (Aspartate-semialdehyde dehydrogenase)-based balanced-lethal recombinant *Yersinia pseudotuberculosis* system tailored with an Asd+ plasmid was used to over-synthesize the heterologous PcrV-HitAT fusion antigen (referred to PH), as well as produce high amounts of OMVs encasing the PH antigen. Intramuscular (i.m.) immunization with the rOMV-PH stimulated robust B and T-cell responses and offered great protection against lethal subcutaneous (s.c.) or intranasal (i.n.) challenge with PA103 strain.
Materials And Methods Bacterial strains, plasmids, culture conditions, and molecular operations. All bacterial strains and plasmids used in this study were listed in the Table 1. All bacterial cultures and molecular and genetic procedures used in this study were described in the Supplementary information (SI).

OMV isolation and analysis. Isolation of OMVs from *Y. pseudotuberculosis* strains was similar as described previously. A brief procedure was described in SI. The OMVs were analyzed by Transmission electron microscopy (TEM), a Bradford assay was performed for quantifying the total protein abundance associated with OMVs as described previously. The heterologous antigen present in the OMV preparations were detected by immunoblotting.

Animal experiments. Animal protocols were in accordance with the NIH "Guide for the Care and Use of the laboratory Animals" and were approved by the Institutional Animal Care and Use Committee at Albany Medical College (IACUC protocol #20-02001). Six-week-old male and female BALB/c mice were purchased from Taconic (Germantown, NY) and acclimated for one week after arrival. Mice were primed by intramuscular (i.m.) vaccination, then boosted at 3 weeks after the initial vaccination. Blood samples were collected via submandibular veins at 2-week intervals to harvest sera for antibody analysis. On 42 days after the initial vaccination, animals were challenged subcutaneously (s.c.) with a lethal dose of PA103 strain in 100 μl PBS to mimic surgical infection. For mimicking acute pneumonic infection, animals were anesthetized with a 1:5 xylazine/ketamine mixture and were challenged intranasally (i.n.) with a lethal dose of PA103 in 40 µl PBS. All infected animals were observed over a 15-day period. The actual numbers of bacterial CFUs were determined by plating serial dilutions of the inoculum on LB agar plates.

For the determination of the bacterial burden, infected animals were euthanized with an overdose of sodium pentobarbital. Lungs, livers, spleens and blood were taken at the indicated times and homogenized in ice-cold PBS (pH 7.4) using a bullet blender at power 7 for 2 min. Serial dilutions of each organ homogenate were plated on LB agar plates, and each count was confirmed with duplicate plates with different dilutions to determine the titers of bacteria per gram of tissue. A mouse multiplex cytokine assay kit (Bio-Plex, Bio-rad) was used to detect cytokines and chemokines in the serum and bronchoalveolar lavage fluid (BALF) collected from the mice according to the manufacturer's instructions.

Antibody responses and opsonophagocytic killing assay. Antibody titers were measured using an enzyme-linked immunosorbent assay (ELISA) described in SI. The opsonophagocytic killing assay were performed as described previously. Briefly, HL-60 cells (ATCC, CCL-240) were differentiated into granulocyte-like cells in the Iscove's Modified Dulbecco's Medium (IMDM) (ATCC) containing 100 mM N',N-dimethylformamide (Sigma) for 5 days. Sera samples from immunized mice containing opsonic antibodies were heat-inactivated (56° C., 30 min) and serially diluted with opsonization buffer (mixture of 80 ml of sterile water, 10 ml of 10× Hank's balanced solution, 10 ml of 1% gelatin, and 5.3 ml of fetal bovine serum). Each well in a 96-well plate contains: 40 µl of $4 \times 10^5$ HL60 cells, $10^3$ CFUs of PA103 in 10 µl of opsonophagocytic buffer, 20 µl of serum, and 10 µl of 1% infant rabbit serum as a complement source (Sigma). Blank wells with the same system in absence of mouse serum were used as negative controls. After 2 h incubation, 10 µl of each sample was plated on LB agar medium. Each sample was performed in triplicate. The opsonophagocytic killing ability was defined as a reduction in CFUs compared with the CFUs in the sera from unimmunized mice.

Analysis of cellular immune responses. Lungs and spleens were obtained aseptically from euthanized animals and lungs were minced and digested with 400 µg/ml of Liberase and 30 µg/ml of DNase (Sigma) at 37° C. for 30 min. Then, tissues were dissociated with 70 µm strainers to obtain single cells. The RBC-lysed individual cell populations ($2 \times 10^6$) were seeded in 12-well cell culture plates and stimulated in vitro for 72 h with 20 µg/ml PH. Four hours before the collection of the cells, Cells in each well were supplemented with brefeldin-A and a monensin cocktail (1:1 ratio) to block Golgi-mediated cytokine secretion. For the flow cytometric analysis of the T-cell populations and their corresponding cytokines, the induced cells were harvested and resuspended in FACS staining buffer containing CD16/32 antibodies (1:200) for 10 min on ice. The T-cell-specific markers were stained using anti-mouse CD3 (FITC), CD4 (PE) and CD8 (APC) antibodies (BioLegend, CA), followed by intracellular cytokine (IFN-γ, PerCP Cy5.5; TNF-α, BV510; IL17A, APC-Cy7) staining using BioLegend Permfix solution and buffer according to the manufacturer's protocol. The entire staining process was performed on ice with 30 min incubation at each step. The events were acquired on BD flow cytometers (FACSymphony A3) and analyzed using FlowJo v.10.

Statistical analysis. The statistical analyses of the data among the groups were performed with one-way ANOVA/univariate or two-way ANOVA with Tukey post hoc tests. The log-rank (Mantel-Cox) test was used for the survival analysis. All data were analyzed using GraphPad PRISM 8.0 software. The data were represented as the mean±standard deviation (SD); ns, no significance, * $p<0.05$,  $p<0.01$, * $p<0.001$, **** $p<0.0001$.

Results

OMVs displaying the heterologous PcrV-HitAT fusion antigen of *P. aeruginosa*. A hypervesiculating and Δasd *Y. pseudotuberculosis* mutant strain, YptbS44 [Table 1 and Supplementary information (SI)] producing adjuvant monophosphoryl lipid A (MPLA) was used here. YptbS44 adapted an Asd+ plasmid, pSMV81 (Table 1, FIG. 17A and SI), in which the perV-hitAT fusion DNA fragment was ligated with the N-terminal β-lactamase signal sequence (bla ss) to facilitate secretion of PcrV-HitAT (PH) into the bacterial periplasm by Type II secretion system. Determination of the PH synthesis showed that YptbS44 harboring pSMV81 synthesized high amounts of PH (MW, 68 kDa) in bacterial cell lysates (BCL) and produced high amounts of OMVs carrying considerable amounts of PH fusion antigen (FIGS. 17B and C). The 10 μg of OMVs from YptbS44(pSMV81) contained around 1 μg PH in comparison to the standard amounts of PH-His fusion protein. No PH was present in YptbS44 harboring an empty plasmid pYA3493 (FIGS. 17B and C).

Immunization with OMVs enclosing PH antigen afforded significant protection against *P. aeruginosa* infection. Prior to challenge study, it was determined that LD50s (50% of lethal dose) of WT PA103 in BALB/c mice by s.c. and i.n. administration were 7.1×106 colony-forming unit (CFU) and 2×105 CFU, respectively. The LD50s of PA103 were similar to previous report. Groups of mice (n=10-15, nearly equal males and females) were immunized intramuscularly with 100 μl PBS containing 50 μg of OMVs from YptbS44 (pSMV81) designated as rOMV-PH, 50 μg of OMVs from YptbS44(pYA3493) designated as rOMV-N, PH (10 μg)/alhydrogel or PBS/alhydrogel, then boosted at 21 days after the prime immunization (FIG. 18A). The rOMV-PH immunization slightly slowed down mouse weight gaining in the first week after immunization in comparison to other immunization groups (FIG. 18B), but did not cause any observable health issues in mice. On day 42 after the initial vaccination, mice were challenged by s.c. or i.n. route, respectively. All rOMV-PH-immunized mice survived s.c. challenge with 6.7×107 CFU (10 LD50) of PA103, while 50% of the rOMV-N-immunized mice and 40% of PH-immunized mice survived the same challenge (FIG. 18C). The rOMV-PH vaccination afforded 73% protection for mice against i.n. challenge with 5×106 (25 LD50) of PA103, only 20% of PH-immunized mice and no rOMV-N-immunized mice survived the same challenge (FIG. 18D). None of the PBS-immunized mice survived both challenges (FIGS. 18C and D).

rOMV-PH vaccination elicited strong antibody responses with significant opsonophagocytic killing capability. Serum antibody responses showed that both PH- and rOMV-PH prime immunization generated similarly high anti-PH IgG titers in mice at week 2 post vaccination, and both boost immunization substantially increased anti-PH IgG titers at week 4 post vaccination (FIG. 19A). Low unspecific anti-PH IgG titers in rOMV-N-immunized mice were stimulated at both weeks 2 and 4 post vaccination (FIG. 19A). Generally, IgG1 is associated with a Th2-like response, while IgG2a is associated with a Th1-like response in mice. Therefore, IgG subtypes to the specific antigen produced in immunized mice can distinguish Th1 and Th2 immune responses. In FIG. 19B, both ratios of anti-PH IgG2a/IgG1 in the rOMV-PH-immunized group (0.998 and 0.891) and the rOMV-N- immunized group (1.031 and 1.046) at weeks 2 and 4 post immunization were substantially higher than those in the PH-immunized group (0.673 and 0.668). Our results demonstrated that the rOMV immunization generated a balanced Th1/Th2 responses, while the PH-immunization skewed to Th2-biased response. In addition, compared with the PH or rOMV-N-immunization, the rOMV-PH immunization primed significantly high anti-PH IgM titers in mice at week 2 post vaccination and remained consistent levels at week 4 post vaccination (FIG. 19C). Anti-PH IgM titers in the PH-immunized mice were substantially higher than those in the rOMV-N-immunized mice at week 2 post vaccination, but declined to the same levels as those in the rOMV-N-immunized mice at week 4 post vaccination (FIG. 19C).

Opsonophagocytic killing (OPK) assay has been used to evaluate correlation of functional antibody levels in serum samples with protection. Thus, whether the PH-specific antibodies were protective was measured using OPK assay. Results showed that only undiluted anti-sera from rOMV-PH-immunized mice exhibited significant OPK activity compared with those from PBS-, PH- or rOMV-N-immunized mice. While, all diluted anti-sera (1:10 or 1:100) from three immunized groups displayed no OPK activity (FIG. 19D).

Vaccination with rOMV-PH induced potent cellular immune responses. Following, T-cell responses were evaluated in the lung and spleen after immunization. Lung cells from rOMV-immunized mice showed increased number of CD4+ and CD8+ T cells in comparison to those from PBS- or PH-immunized mice after in vitro stimulation with PH (FIGS. 20E and F). Further, cytokine producing T cells were analyzed by Flow cytometry. Lung CD4+ T-cells from rOMV-PH-immunized mice displayed significantly higher production of IFN-γ, IL-17A or TNF-α than those from PH- and PBS-immunized mice after in vitro induction with PH (FIG. 20B). Production of IFN-γ, IL-17A or TNF-α in lung CD4+ T-cells from PH-immunized mice was low in comparison to that from rOMV-PH-immunized mice, but was significantly higher than that from PBS-immunized mice (FIG. 20B). Lung CD8+ T cells from rOMV-PH-immunized mice showed comparable IFN-γ production to those from PH-immunized mice, but higher IFN-γ production than those from PBS-immunized mice after stimulation. Comparable levels of IL-17 and TNF-α were produced in rOMV-PH-, PH- or PBS-immunized animals (FIG. 20D).

In similar fashion, splenic CD4+ T cells from rOMV-PH-immunized mice significantly increased after in vitro stimulation with the PH antigen in comparison to cells from PBS- or PH-immunized mice. There was no significant increase in splenic CD4+ T cells from PH-immunized mice compared to cells from PBS-immunized mice (FIGS. 21E and F). Splenic CD8+ T cells from rOMV-PH-immunized mice after stimulation were substantially higher than those from PBS- or PH-immunized mice. Also, splenic CD8+ T cells from PH-immunized mice showed increased induction in comparison to those from PBS-immunized mice (FIGS. 21E and F). Specifically, splenic CD4+ T-cells from rOMV-PH-immunized mice demonstrated significantly higher production of IFN-γ, IL-17A or TNF-α than those from PH- and PBS-immunized mice (FIG. 21B). Also, higher production of TNF-α was observed in spleen CD4+ T-cells from PH-immunized mice in comparison to those from PBS-immunized mice. (FIG. 21B). Spleen CD8+ T cells from rOMV-PH-immunized mice showed higher production of IFN-γ and TNF-α than those from PH- and PBS-immunized mice. Production of IL-17A in splenic CD8+ T cells was low and no significant difference among three immunized groups (FIG. 21D). In addition, lung and spleen lymphocytes and their cytokine production were comparable without antigen stimulation in each immunized group (data not shown). Altogether, these results indicated that rOMV-PH vaccination elicited more potent antigen-specific T-cell responses in mice than PH vaccination.

The rOMV-PH vaccination effectively controlled bacteria and host inflammation. Further, in vivo responses of immunized mice challenged with a sub-lethal dose of PA103 were evaluated. Mice were challenged with 5×106 CFU PA103 by s.c. administration and monitored bacterial burdens in different tissues and cytokine/chemokine production in serum on 36 h post infection. Results showed that striking increases of PA titers in lungs (mean 5.5 log 10 CFU/g tissue) and livers (mean 6.2 log 10 CFU/g tissue), and moderate bacterial titers in spleens (mean 4.8 log 10 CFU/g tissue) and blood (mean 3.8 log 10 CFU/g tissue) in the PBS-immunized mice. Bacterial titers within all four organs in PH-immunized mice substantially decreased in comparison to PBS-immunized mice, but still retained significantly higher in lungs and spleens than those in rOMV-PH-immunized mice. No bacteria disseminated to those organs in rOMV-PH-immunized mice (FIG. 22A). Analysis of serum cytokine/chemokine in mice on 36 h post s.c. infection showed that dramatically increased levels of cytokines (IL-1β and IL-6) and chemokine (KC) were secreted into the sera of PBS-immunized mice in comparison to those in PH- or rOMV-PH-immunized mice. Levels of serum IL-10 in both PBS- and PH-immunized mice were substantially higher than those in rOMV-PH-immunized mice, but levels of serum IL-10 in PH-immunized mice were even higher than those in PBS-immunized mice (FIG. 22B). The rOMV-PH-immunized mice produce the greatest amounts of serum IL-17A among all three immunized groups. In comparison to PBS-immunized mice, PH-immunized mice also produced significantly high amounts of IL-17A. while, levels of TNF-α were comparable in three immunization groups after infection (FIG. 22B).

Similarly, groups of immunized mice were evaluated by i.n. challenge with 5×105 CFU PA103. On 36 h post pulmonary infection, PBS-immunized mice were found to have strikingly increased bacterial titers in lungs (mean 7.0 log 10 CFU/g tissue), and rapidly disseminated to livers (mean 6.0 log 10 CFU/g tissue), spleens (mean 5.8 log 10 CFU/g tissue) and blood (mean 4.8 log 10 CFU/g tissue). In comparison to the PBS immunization, the PH- or OMV-PH immunization substantially decreased bacterial burdens within lungs, livers and spleens of mice. However, the OMV-PH immunization had more efficiency to clear bacteria from mouse blood than the PH-immunization (FIG. 23A). Analysis of BALF cytokine/chemokine in mice after i.n. infection showed that dramatically high levels of cytokines IL-6, IL-10, IFN-γ and TNF-α) and chemokine (KC) were secreted into the BALF of PBS-immunized mice on 36 h post infection in comparison to those in PH- or rOMV-PH-immunized mice (FIG. 23B). The rOMV-PH-immunized mice produced even less amounts of IL-10 and IL-6 than the PH-immunized mice did. Like serum cytokine responses, the rOMV-PH-immunized mice produced significantly higher amounts of IL-17A in BALFs than PBS- or PH-immunized mice did (FIG. 23B).

Discussion

The increasing prevalence of multidrug-resistant *P. aeruginosa* (PA) infections in healthcare settings justifies the urgent need for an effective vaccine against this organism. Barriers to PA vaccine development include the presence of phenotypically diverse PA strains, the diverse virulence mechanisms, and lack of reliable animal models to mimic CF patients. A number of PA vaccine candidates are being tested in clinical trials, but so far no licensed vaccines are available for human use. Among them, a PA subunit vaccine (IC43) composed of OprI and a fragment of the outer membrane protein OprF was evaluated in a phase III clinical trial (NCT01563263). Immunization with 100 µg of IC43 was well tolerated in a large group of mechanically ventilated patients as well as achieved high immunogenicity, but did not present significant clinical benefit over placebo in terms of overall mortality. Human clinical trials showed that anti-PcrV antibody or its fragment could reduce inflammation and damage of the airway of CF patients, but directly using PcrV antigen as a vaccine component seemed to never be evaluated in human clinical trials probably due to protein purity or other unmentioned issues. In addition, Holder et al reported that immunization with PcrV alone did not provide long-term protection to burned mice infected with the highly toxigenic strain 1071. Moreover, purified antigens as subunit vaccines administered alone have limited immunogenicity and vaccination with subunit vaccines prefers to generate humoral response. Many studies reach consistent points that an excellent PA vaccine should stimulate antibodies combined with both Th1- and Th17-type CD4+ T cell responses to provide effective protection against pulmonary and systemic PA infection. Currently, this dilemma for subunit vaccines is being addressed with different improved vaccine carriers. Among them, using self-adjuvanting OMVs as a carrier not only circumvents the requirements of antigen-purification for traditional subunit vaccines, but also stimulates potent specific humoral and cellular responses to the delivered antigens.

Our studies showed that i.m. immunization with rOMV-PH afforded complete protection against s.c. challenge and 73% protection against i.n. challenge with the virulent PA103 strain (FIGS. 18C and D), providing evidence that using rOMVs from a recombinant *Y. pseudotuberculosis* strain to deliver a heterologous PH fusion antigen of *P. aeruginosa* was feasible. Less protection against pneumonic infection might be owing to the immunization route. Usually, systemic immunization like i.m, or s.c. is less effective in generation of high-avidity natural antibodies or cellular responses at mucosal sites and results in inferior protection from mucosal challenge. Thus, combining prime-boost immunization with systemic and mucosal rOMV-PH might achieve complete protection against both systemic and respiratory PA infection. In addition, combination of triple- or tetra-antigen may further enhance protection against PA infection.

Generally, antigen-specific antibodies induced by a vaccine candidate are able to correlate with protection and assist killing of host target cells infected by bacteria. However, our results showed that immunization with the PH/alhydrogel generated comparable high titers of PH-specific antibody in mice to the rOMV-PH immunization (FIG. 19A) but failed to provide effective protection against s.c. or i.n. PA103 challenge (FIGS. 18C and D). A possible reason is the PH immunization stimulated Th2-biased immune response (IgG2a/IgG1=0.67), while rOMV-PH vaccination induced more balanced Th1/Th2 immune response (IgG2a/IgG1=0.9) (FIG. 19B). In addition, the rOMV-PH immunization primed significantly higher anti-PH IgM titers in mice than the PH-immunization at weeks 2 and 4 post vaccination (FIG. 19C). A growing evidence indicates that IgM provides a first line of defense during microbial infections, prior to the generation of high affinity IgG responses. However, whether the antigen-specific IgM is involved in the protection needs to be further investigated in the future. Interestingly, in vitro OPK assay showed that anti-sera from rOMV-PH immunized mice could effectively kill PA, instead of anti-sera from PH-immunized mice (FIG. 19D). Our results were not consistent with several previous studies, in which anti-PcrVNH sera from the PcrVNH-immunized mice or POH-specific antibodies from the trivalent subunit (PcrV-OprI-Hcp1, POH) vaccinated mice exhibited significant OPK activity to PA. Regarding these, it is speculated that distinct antigen combination or probably different antibody compositions in sera from immunized mice may lead to the inconsistency.

Based upon antibody analysis (FIG. 19), humoral response alone could not provide optimal protection against PA infection, while cellular immune responses are required to achieve comprehensive protection. Measurement of T cell responses in lungs and spleens showed that the rOMV-PH immunization stimulated substantially higher T cell responses than the PH immunization (FIGS. 20 and 21), which is well correlated with animal survival after challenge (FIGS. 18C and D). In addition, consistent with the immune protection and responses, rOMV-PH-immunized mice had more efficiency to clear PA after s.c. or i.n. challenge than the PH- or PBS-immunized mice (FIGS. 22A and 23A). Measurement of cytokines/chemokines in the sera and BALFs of mice on 36 h post PA103 infection indicated that the rOMV-PH immunization more effectively coordinated cytokines/chemokines production in mice than the PH or PBS immunization (FIGS. 22B and 23B). Studies have implicated that overproduction of IL-10, IL-6 and IL-10 in mice and human are associated with sepsis and IFN-γ expression was enhanced persistently in patients who died of sepsis. In consistence to mouse survival after s.c. PA103 challenge, the amounts of serum IL-1β, IL-6 IL-10, and IFN-γ in PH-immunized mice were significantly higher than those in rOMV-PH-immunized mice on 36 h post infection (FIG. 22B). Jin et al showed that CXCL1 (KC) contributed to host defense in polymicrobial sepsis. However, our data showed that rOMV-PH-immunized mice produce less amounts of KC in sera than PH-immunized mice after infection (FIG. 22B). In addition, KC is essential for neutrophil migration and expression of proinflammatory mediators, thus overmounts of KC in sera recruiting excessive neutrophils may cause tissue damage and organ failure. In similar manner, higher amounts of IL-1β and IL-6 secreted into BALFs of PH-immunized mice after i.n. PA103 challenge than those of rOMV-PH-immunized mice, which can reflect animal survival after infection (FIG. 23B). However, rOMV-PH-immunized mice produced substantially higher IL-17 in both sera and BALFs than PH-immunized mice after both s.c. and i.n. challenge (FIGS. 22B and 23B), suggesting that IL-17 plays a protective role against PA infection. Our results were consistent to several previous studies, but the detailed role of IL-17 induced by the rOMV-PH immunization for protection needs to be pursued further. Altogether, our studies showed that self-adjuvating OMVs from recombinant *Y. pseudotuberculosis* could be as a carrier for delivering a heterologous fusion antigen (PH) and vaccination with rOMV-PH induced robust humoral, Th1 and Th17 cell responses, resulting in comprehensive protection against lethal PA infection. Thus, OMVs delivering PA antigens would be a novel promising vaccine preventing unrestrained spread of PA in healthcare settings.

EXAMPLE 4

TABLE 5

*P. aeruginosa* strains and plasmids used in this study

| Strain or Plasmid | Genotype or relevant characteristics |
|---|---|
| Strains | |
| *E. coli* | |
| Top 10 | F⁻ mcrA Δ(mrr-hsdRMS-mcrBC) φ80lacZΔM15 ΔlacX74 recA1 araD139 Δ(ara-leu)7697 galU galK rpsL endA1 nupG |
| χ6212 | F- λ- φ80 Δ(lacZYA-argF) endA1 recA1 hsdR17 deoR thi-1 glnV44 gyrA96 relA1 ΔasdA4 |
| SM10(λpir) | Km$^r$; thi-1 thr-1 leuB26 tonA21 lacY1 supE44 recA integrated RP4-2 Tc$^r$::Mu aphA⁺ (RP4-2 is RP4 ΔTn1) |
| RH03 | Km$^s$; Δasd::FRT ΔaphA::FRT SM10(λpir) |
| *P. aeruginosa* | |
| *P. aeruginosa* PA103 | Wild-type strain |
| ΔexoU PA103 | ΔexoU |
| PA-m1 | ΔlpxL1 |
| PA-m2 | ΔexoU ΔwbjA |
| PA-m3 | ΔexoU ΔwbjA ΔexoA |
| PA-m4 | ΔexoU ΔwbjA ΔexoA ΔexoT |
| PA-m5 | ΔexoU ΔwbjA ΔexoA ΔexoT ΔlasA |
| PA-m6 | ΔexoUΔwbjAΔexoAΔexoTΔlasAΔlasB |
| PA-m7 | ΔexoUΔwbjAΔexoAΔexoTΔlasAΔlasB ΔpchA |
| PA-m8 | ΔexoUΔwbjAΔexoAΔexoTΔlasAΔlasB ΔpchAΔphzM |
| PA-m9 | ΔexoUΔwbjAΔexoAΔexoTΔlasAΔlasB ΔpchAΔphzMΔalg |
| PA-m10 | ΔexoUΔwbjAΔexoAΔexoTΔlasAΔlasB ΔpchAΔphzMΔalgΔRhlAB |
| PA-m11 | ΔexoUΔwbjAΔexoAΔexoTΔlasAΔlasB ΔpchAΔphzMΔalgΔRhlABΔpvdA |
| PA-m12 | ΔexoUΔwbjAΔexoAΔexoTΔlasAΔlasB ΔpchAΔphzMΔalgΔRhlABΔpvdAΔplcH |
| PA-m13 | ΔexoUΔwbjAΔexoAΔexoTΔlasAΔlasB ΔpchAΔphzMΔalgΔRhlABΔpvdAΔplcHΔlpxL |
| PA-m14 | ΔexoUΔwbjAΔexoAΔexoTΔlasAΔlasBΔpchAΔphzMΔalgΔRhlABΔpvdAΔplcHΔlpxLΔphoA |
| Plasmids | |
| pYA3342 | Asd⁺ vector, P$_{trc}$, pBR ori |
| pYA3493 | Asd⁺ vector with β-lactamase N-terminal signal sequence, P$_{trc}$, pBR ori |
| pDMS197 | Suicide vector, Tet$^r$, mob⁻ (RP4)R6K ori, sacB |
| pUCP20 | *E. coli-Pseudomonas* shuttle vector; Ap$^r$ Cb$^r$ |
| pSMV81 | The pcrV-hitA$_T$ DNA fragment was cloned into sites of EcoRI and HindIII in the pYA3494 |
| pSMV82 | The pcrV-hitA$_T$-6xhis fragment was cloned into sites of NcoI and HindIII in the pYA3342 |
| pSMV83 | The P$_{trc}$-bla ss-pcrV-hitA$_T$ DNA fragment was cloned into the pUCP20 |

TABLE 6

Primers used in the *P. aeruginosa* study.

| Primer name | Sequence $^a$ (5' to 3') |
|---|---|
| exoT-UF | cgggagctctatccatcgggttctccgccccgg (SEQ ID NO: 10) |
| exoT-UR | tggcaacgccggggtcccgggaggggcaggcggcgcgtcctgacggga (SEQ ID NO: 11) |
| exoT-DF | tcccgtcaggacgcgccgcctgcccctcccgggaccccggcgttgcca (SEQ ID NO: 12) |
| exoT-DR | cggtctagatgactgcgtctcgttcg (SEQ ID NO: 13) |
| exoA-UF | cgggagctcgacagctcggcgtagaccagc (SEQ ID NO: 14) |
| exoA-UR | acccatcacaggagccatcgcggtggtgattccctcggcgatc (SEQ ID NO: 15) |
| exoA-DF | gatcgccgagggaatcaccaccgcgatggctcctgtgatgggt (SEQ ID NO: 16) |
| exoA-DR | cggtctagagcgacgctcgacaatgctct (SEQ ID NO: 17) |
| lasA-UF | cgggagctcgtcggcggcttcttcgggccgc (SEQ ID NO: 18) |
| lasA-UR | ttcgatgaccaggagctaccgtcggcgcggggcccgctcca (SEQ ID NO: 19) |

TABLE 6-continued

Primers used in the *P. aeruginosa* study.

| Primer name | Sequence<sup>a</sup> (5' to 3') |
|---|---|
| lasA-DF | tggagccgggccccgcgccgacgggtagctcctggtcatcgaa (SEQ ID NO: 20) |
| lasA-DR | cggtctagaagccggacgaggacgacggtta (SEQ ID NO: 21) |
| lasB-UF | cgggagctcgatgttccacggggtgttcca (SEQ ID NO: 22) |
| lasB-UR | tgctggccggggccaccgagcttacttgttcagttctcctggtttttc (SEQ ID NO: 23) |
| lasB-DF | gaaaaaaccaggagaactgaacaagtaagctcggtggcccggccagca (SEQ ID NO: 24) |
| lasB-DR | cggtctagaggtcgtgtgctggggatcgaa (SEQ ID NO: 25) |
| wbjA-UF | cgggagctcgctgctacttcacccatagctagcg (SEQ ID NO: 26) |
| wbjA-UR | ctttctatcgagaaccccttccagactgcgctacaaggccggccagga (SEQ ID NO: 27) |
| wbjA-DF | tcctggccggccttgtagcgcagtctggaagggggttctcgatagaaag (SEQ ID NO: 28) |
| wbjA-DR | cggtctagacccaccataacaccatatgcggtca (SEQ ID NO: 29) |
| pchA-UF | cgggagctccacctgttcgtctccgcccatc (SEQ ID NO: 30) |
| pchA-UR | ggccgcagggggtcttcgtttgcggcaccccgtgtctgcgc (SEQ ID NO: 31) |
| pchA-DF | gcgccagacacggggtgccgcaaacgaagaccccctgcggcc (SEQ ID NO: 32) |
| pchA-DR | cggtctagaaactaatcgccatgaatgaaaa (SEQ ID NO: 33) |
| phzM-UF | cgggagctcgctgccggaggacgtggagaac (SEQ ID NO: 34) |
| phzM-UR | tggccttcgagatctttcagggatcggaactctcaacggttggc (SEQ ID NO: 35) |
| phzM-DF | gccaaccgttgagagttccgatcctgaaagatctgaaggcca (SEQ ID NO: 36) |
| phzM-DR | cggtctagaaaggcaataggagtttcatccag (SEQ ID NO: 37) |
| alg-UF | cgggagctcgacgtgctgctcaacctggcttcc (SEQ ID NO: 38) |
| alg-UR | catcttcatggtcgggtaccggtaggatgttttctctgcgaggg (SEQ ID NO: 39) |
| alg-DF | ccctcgcagagaaaacatcctaccggtacccgaccatgaagatg (SEQ ID NO: 40) |
| alg-DR | cggtctagacgccctggtcgggatagtcgta (SEQ ID NO: 41) |
| rhlAB-UF | cgggagctcctgcctgggcaagagcacctac (SEQ ID NO: 42) |
| rhlAB-UR | tatctgttatgccagcaccgtttcacacctcccaaaaatttt (SEQ ID NO: 43) |
| rhlAB-DF | aaaatttttgggaggtgtgaaacggtgctggcataacagata (SEQ ID NO: 44) |
| rhlAB-DR | cggtctagaggcgatttccccggaactcttg (SEQ ID NO: 45) |
| pvdA-UF | cgggagctctggaacgcctgctcgccgctca (SEQ ID NO: 46) |
| pvdA-UR | gccaatccagaggaactggaatcggcgccacgccgccacgc (SEQ ID NO: 47) |
| pvdA-DF | gcgtggcggcgtggcgccgattccagttcctctggattggc (SEQ ID NO: 48) |
| pvdA-DR | cggtctagatgtcttcatcgagggttccagtta (SEQ ID NO: 49) |
| plcH-UF | cgggagctcttgacttccggtgggtaggtttcg (SEQ ID NO: 50) |
| plcH-UR | accacccgggaaataaaacgagcgaggagtccatcgcatga (SEQ ID NO: 51) |
| plcH-DF | tcatgcgatggactcctcgctcgtttattcccgggggt (SEQ ID NO: 52) |
| plcH-DR | cggtctagaggagtagtggccgatgatccct (SEQ ID NO: 53) |
| htrB2-UF | cgggagctcgcgcaccggagtcttcaccaccttt (SEQ ID NO: 54) |
| htrB2-UR | cgcgtccggaatgcccgtccggacggttccgacgacgatca (SEQ ID NO: 55) |
| htrB2-DF | tgatcgtcgtcggaaccgtccggacgggcattccggacgcg (SEQ ID NO: 56) |
| htrB2-DR | cggtctagatcgccgaagtactcgcggttga (SEQ ID NO: 57) |
| phoA-UF | cgggagctcctgtgcaaattgttgcgcacat (SEQ ID NO: 58) |
| phoA-UR | cctttttcgttctggtccgagacgcatttccctatgttgag (SEQ ID NO: 59) |
| phoA-DF | ctcaacatagggaaatgcgtctcggaccagaacgaaaagg (SEQ ID NO: 60) |
| phoA-DR | cggtctagagcgccctgcaacgactgctgtt (SEQ ID NO: 61) |
| PcrV1 | gaattcgaacaggaagaactgctg (SEQ ID NO: 62) |
| PcrV2 | cggaagcttggatccaatggcactcagaatatca (SEQ ID NO: 63) |
| HitA1 | ggatccggtggcggcggtagcg (SEQ ID NO: 64) |
| HitA2 | aagcttttaatggtgatgatgatg (SEQ ID NO: 65) |

<sup>a</sup> Underlining indicates restriction endonuclease recognition sequences.

Trimming *P. aeruginosa* to mitigate toxicity of outer membrane vesicles. A multitude of virulence factors produced by PA are involving in acute and chronic infections. Studies have illustrated that OMVs from WT PA can package numerous virulence factors, such as virulence effectors of the type III secretion system (T3SS) and toxins, and deliver them into host cells, impairing immune response and cytotoxicity. The toxins (ExoU, ExoT or ExoS) secreted by T3SS facilitated PA to breach in the epithelial barrier by antagonizing wound healing during colonization and promoting cell injury causing pneumonia. Also, several toxic effectors (Exotoxin A, LasA and LasB) of Type II secretion system (T2SS) contribute to bacterial pathogenicity. In addition, high levels of antibodies against alginate or elastases are induced upon PA infection, but these antibodies have poor opsonic activities, especially in CF individuals, fail to clear the infection effectively, and even exacerbate lung infection. Siderophores (pyochelin and pyoverdine), rhamnolipids, LPS, and alkaline phosphatases also facilitate PA infection. To mitigate toxicity caused by those factors, 14 genes (FIG. 1A) were consecutively deleted to generate the PA-m14 mutant strain (Table 1). Mutations did not obviously alter morphology of PA-m14 in comparison to WT PA103 (FIG. S1), but the size of OMVs from PA-m14 was much smaller than that from WT PA103 (FIG. 1B). Western blot showed that OMVs isolated from WT PA103 enclosed considerable amounts of the known toxins (ExoA and ExoU) (FIG. 1C) that potentiate toxicity of OMVs to mammalian hosts. Following, in vivo toxicity testing of different OMVs showed that mice injected intramuscularly (i.m.) with 50 μg OMVs from WT PA103 succumbed within 3 days, but 80% mice survived by i.m. injection with 50 μg OMVs from PA-m1 strain with a single mutation of PA103_1714 (designated lpxL1) encoding lauroyltransferase that is response for the addition of laurate to lipid A. The PA103_1714 had 99.038% identity with PA3242 (designated HtrB2) in PAO1 strain. No mice succumbed by i.m. injection with 50 μg OMVs from PA-m6, PA-m11 or PA-m14, or even with 100 μg OMVs from PA-m14 (FIG. 1D), implying that deletion of virulence factors and/or deduction of the fatty acid chain of lipid A significantly diminished the toxicity of PA OMVs. Regarding above results, the PA-m14 was chosen for the following studies.

Increasing PcrV-Hit$A_T$ fusion antigen enclosed by *P. aeruginosa* OMVs. Studies showed that active and passive immunization with the PcrV antigen or its protective antibody decreased lung inflammation and injury in a murine infection model and a burn mouse model. The components in PA iron acquisition systems, such as PA4359, PA4514, HitA (PA4687), and HitB (PA4688) are involved in iron transportation and associated with bacterial virulence, rendering them as potential vaccine candidates. Immunization with the ferric iron-binding periplasmic protein HitA provided protection for mice against systemic PA infection. PcrV and HitA antigen among different serotypes of PA has 98~100% identity, respectively. However, OMVs directly isolated from PA-m14 strain contained low amounts of PcrV and HitA, which may limit OMV immunogenicity. In order to increase protective antigens enclosed in OMVs, PcrV (E28-I294, removing signal peptide) was fused with truncated HitA (D28-N355) from PA103 strain together designated as PcrV-HitAT (68 kDa, referred to PH) for the proof of concept. Therefore, the pSMV83 plasmid (Table 5 and FIG. 24A) was constructed, in which the bla ss-pcrV-hit$A_T$ is driven by strong $P_{trc}$ promoter for high expression of the pcrV-hit$A_T$ fusion gene in PA, and the bla ss encodes N-terminal β-lactamase signal peptide to facilitate secretion of the PH fusion antigen into periplasm of PA. Subsequently, the pSMV83 plasmid was introduced into PA-m14 strain to determine synthesis of PH antigen in bacteria and OMVs. Results showed that the PA-m14(pSMV83) strain synthesized significant amounts of PH and OMVs from this strain trapped decent amounts of PH antigen in comparison to PA-m14 harboring the empty plasmid pUCP20 (FIGS. 24B & C)

Immunization with recombinant PA OMVs induces protection against *P. aeruginosa* infection. Groups of mice (n=10, 5 males and 5 females) were intramuscularly (i.m.) immunized with 50 μg OMVs purified from PA-m14 (pSMV83) (referred to OMV-PH) in 100 μl PBS, in which contains ~10 μg PcrV-HitAT, and boosted at 21 days after prime immunization (FIG. 25A). Immunization with 50 μg OMVs from PA-m14(pUCP20) (referred to OMV-NA), PH (10 μg)/alhydrogel or PBS/alhydrogel (PBS) as experimental controls. On day 42 after the initial vaccination, mice were challenged with PA by s.c. administration to mimic surgical infection or by i.n. route to mimic acute pneumonic infection. All OMV-immunized mice survived s.c. challenge with $7.4\times10^7$ CFU (10 $LD_{50}$) of PA103, while 40% of the PH-immunized mice survived the same challenge (FIG. 25B). For i.n. challenge, vaccination with OMV-PH afforded 70% protection for mice infected with $6.5\times10^6$ CFU (~30 $LD_{50}$) of PA103, but only 20% mice immunized with PH or OMV-NA survived the same challenge (FIG. 25C). None of PBS-immunized mice survived both challenges (FIGS. 25B and C).

Mice with OMV-PH immunization rapidly halt *P. aeruginosa* infection. On day 2 post infection, PBS-immunized mice had substantially higher PA titers (mean 7.2 $\log_{10}$ CFU/g tissue) in lungs, spleens (mean 5.7 $\log_{10}$ CFU/g tissue), livers (mean 5.6 $\log_{10}$ CFU/g tissue) and bloods (mean 5.2 $\log_{10}$ CFU/g tissue) than PH-, OMV-NA or OMV-PH immunized mice. In the PH-immunized mice, bacteria reached moderate levels in livers (mean 1.2 $\log_{10}$ CFU/g tissue) and blood (mean 2.5 $\log_{10}$ CFU/g tissue), but no bacteria were detected in spleens (FIG. 25D). In the OMV-NA-immunized mice, bacteria reached moderate levels in spleens (mean 4.3 $\log_{10}$ CFU/g tissue) and livers (mean 1.2 $\log_{10}$ CFU/g tissue), but no bacteria were detected in blood (FIG. 25D). No PA were disseminated to spleens, livers, and blood in OMV-PH-immunized mice (FIG. 25D).

Mice with OMV-PH immunization rapidly halt *P. aeruginosa* infection. At 48 h after s.c. challenge with PA103, significant high bacteria titers were detected in livers (mean 4.2 $\log_{10}$ CFU/g tissue) and blood (mean 4.6 $\log_{10}$ CFU/g tissue) of PBS-immunized mice, moderate bacterial titers were observed in spleens (mean 2.7 $\log_{10}$ CFU/g tissue) and lungs (mean 2.8 $\log_{10}$ CFU/g tissue) of PBS-immunized mice. PH immunization could significantly reduce bacterial titers in livers, spleens, lungs, and blood, but not completely clear PA from livers, spleens, and blood at 48 h post infection. No bacteria were detected in OMV-NA or OMV-PH-immunized groups in all of tissues at 48 h post infection (FIG. 25E). Data of bacteria burdens in mice organs after PA103 challenge could well correlate with animal survivals and host responses

What is claimed is:

1. A vaccine platform, comprising a plurality of non-naturally occurring outer membrane vesicles produced from a *Yersinia* bacterium, wherein the outer membrane vesicles enclose monophosphoryl lipid A and an amount of a heterologous PcrV-HitAT fusion antigen of *Pseudomonas aeruginosa*.

2. The vaccine platform of claim 1, wherein the bacterium comprises *Yersinia pestis*.

3. The vaccine platform of claim 1, wherein the bacterium comprises *Yersinia pseudotuberculosis*.

4. The vaccine platform of claim 1, wherein the outer membrane vesicles are free of any plasminogen activator (Pla).

5. The vaccine platform of claim 1, wherein the outer membrane vesicles are free of any murine toxin.

6. A system for producing vaccines, comprising:
a *Yersinia* bacterium that has been modified to synthesize outer membrane vesicles that enclose monophosphoryl lipid A and an amount of a heterologous PcrV-HitAT fusion antigen of *Pseudomonas aeruginosa*.

7. The system of claim 6, wherein the bacterium comprises *Yersinia pestis*.

8. The system of claim 6, wherein the bacterium comprises *Yersinia pseudotuberculosis*.

9. The system of claim 6, wherein the outer membrane vesicles are free of any plasminogen activator (Pla).

10. The system of claim 6, wherein the outer membrane vesicles are free of any murine toxin.

11. A method of producing vaccines, comprising:
   modifying a *Yersinia* bacterium to synthesize outer membrane vesicles that enclose monophosphoryl lipid A and an amount of a heterologous PcrV-HitAT fusion antigen of *Pseudomonas aeruginosa*;
   culturing the *Yersinia* bacterium; and
   isolating the outer membrane vesicles that include monophosphoryl lipid A and the amount of the heterologous PcrV-HitAT fusion antigen of *Pseudomonas aeruginosa*.

12. The method of claim 11, wherein the bacterium comprises *Yersinia pestis* and *Yersinia pseudotuberculosis*.

13. The method of claim 11, wherein the outer membrane vesicles are free of any plasminogen activator (Pla).

14. The method of claim 11, wherein the outer membrane vesicles are free of any murine toxin.

* * * * *